United States Patent
Govek et al.

(10) Patent No.: US 9,475,798 B2
(45) Date of Patent: *Oct. 25, 2016

(54) AZETIDINE ESTROGEN RECEPTOR MODULATORS AND USES THEREOF

(71) Applicant: Genentech, Inc., South San Francisco, CA (US)

(72) Inventors: Steven P. Govek, San Diego, CA (US); Mehmet Kahraman, La Jolla, CA (US); Nicholas D. Smith, San Diego, CA (US); Jeffrey H. Hager, San Diego, CA (US); Edna Chow Maneval, Del Mar, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/963,653

(22) Filed: Dec. 9, 2015

(65) Prior Publication Data

US 2016/0090377 A1   Mar. 31, 2016

Related U.S. Application Data

(63) Continuation of application No. PCT/US2014/043038, filed on Jun. 18, 2014.

(60) Provisional application No. 61/837,091, filed on Jun. 19, 2013, provisional application No. 61/952,651, filed on Mar. 13, 2014.

(51) Int. Cl.
   *C07D 405/12*   (2006.01)
   *A61K 45/06*    (2006.01)
   *A61K 31/397*   (2006.01)

(52) U.S. Cl.
   CPC ........... *C07D 405/12* (2013.01); *A61K 31/397* (2013.01); *A61K 45/06* (2013.01)

(58) Field of Classification Search
   None
   See application file for complete search history.

(56) References Cited

U.S. PATENT DOCUMENTS

| | | | |
|---|---|---|---|
| 5,407,947 A | 4/1995 | Bryant | |
| 6,262,270 B1 | 7/2001 | Draper | |
| 8,299,112 B2 | 10/2012 | Smith et al. | |
| 8,455,534 B2 | 6/2013 | Smith et al. | |
| 8,703,810 B2 | 4/2014 | Kahraman et al. | |
| 9,078,871 B2 | 7/2015 | Kahraman et al. | |
| 9,187,460 B2 | 11/2015 | Smith et al. | |
| 9,193,714 B2 | 11/2015 | Smith | |
| 2003/0207380 A1 | 11/2003 | Saito et al. | |
| 2004/0034017 A1 | 2/2004 | Kuenzer | |
| 2004/0259915 A1 | 12/2004 | Kanojia | |
| 2012/0071535 A1 | 3/2012 | Smith et al. | |
| 2013/0116232 A1 | 5/2013 | Kahraman | |
| 2013/0231333 A1 | 9/2013 | Smith et al. | |
| 2015/0105403 A1 | 4/2015 | Smith et al. | |
| 2015/0258080 A1 | 9/2015 | Hager | |
| 2015/0258099 A1 | 9/2015 | Hager | |

FOREIGN PATENT DOCUMENTS

| | | |
|---|---|---|
| WO | 2015/082990 A1 | 6/2011 |
| WO | 2011/156518 A2 | 12/2011 |
| WO | 2012/037410 A2 | 3/2012 |
| WO | 2012/037411 A2 | 3/2012 |
| WO | 2013/056178 | 4/2013 |
| WO | 2013/090829 | 6/2013 |
| WO | WO2013090836 * | 6/2013 |
| WO | 2013/142266 A1 | 9/2013 |
| WO | 2014/151899 A1 | 9/2014 |
| WO | 2014/205138 A1 | 12/2014 |
| WO | 2015/136016 A2 | 9/2015 |
| WO | 2015/136017 A1 | 9/2015 |

OTHER PUBLICATIONS

Rydzewski, Real World Drug Discovery 2008, 42-43.*
Pubmed printout of "Bush et al., SERM and cardiovascular disease in women. How do these agents affect risk? Postgraduate Medicine, 2001, Spec No: 17-24".*
Horig, H., Pullman, W. From bench to clinic and back: Perspective on the 1st IQPC Translational Research conference. Journal of Translational Medicine. Dec. 2004, 2, 44.*
Schafer, S., Kolkhof, P. Failure is an option: learning from unsuccessful proof-of-concept trials. Drug Discovery Today. Nov. 2008, 13, 913-916.*
Govek et al., "Optimization of an indazole series of selective estrogen receptor degraders: Tumor regression in a tamoxifen-resistant breast cancer xenograft" Bioorg Med Chem Lett. 25(22):5163-7 (2015).
ISR for PCT/US2014/043038, mailed on Oct. 23, 2014.
Lai et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts" Journal of Medicinal Chemistry 58(12):4888-4904 ( 2015).

* cited by examiner

*Primary Examiner* — Rebecca Anderson
*Assistant Examiner* — Po-Chih Chen
(74) *Attorney, Agent, or Firm* — Alex Andrus

(57) ABSTRACT

Described herein are compounds that are estrogen receptor modulators. Also described are pharmaceutical compositions and medicaments that include the compounds described herein, as well as methods of using such estrogen receptor modulators, alone and in combination with other compounds, for treating diseases or conditions that are mediated or dependent upon estrogen receptors.

14 Claims, No Drawings

AZETIDINE ESTROGEN RECEPTOR MODULATORS AND USES THEREOF

RELATED APPLICATIONS

This application is a continuation of International Application No. PCT/US2014/043038 having an International Filing Date of 18 Jun. 2014, and which claims the benefit of priority to U.S. provisional patent application No. 61/837,091, filed on Jun. 19, 2013; and U.S. provisional patent application No. 61/952,651, filed on Mar. 13, 2014; all of which are incorporated by reference in their entirety.

FIELD OF THE INVENTION

Described herein are compounds, including pharmaceutically acceptable salts, solvates, metabolites, prodrugs thereof, methods of making such compounds, pharmaceutical compositions comprising such compounds, and methods of using such compounds to treat, prevent or diagnose diseases or conditions that are estrogen sensitive, estrogen receptor dependent or estrogen receptor mediated.

BACKGROUND OF THE INVENTION

The estrogen receptor ("ER") is a ligand-activated transcriptional regulatory protein that mediates induction of a variety of biological effects through its interaction with endogenous estrogens. Endogenous estrogens include 17β-estradiol and estrones. ER has been found to have two isoforms, ER-α and ER-β.

Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions.

SUMMARY OF THE INVENTION

In one aspect, presented herein are compounds of Formulas (I), (II), and (III), or a pharmaceutically acceptable salt, solvate or prodrug thereof, that diminish the effects of estrogens with estrogen receptors and/or lower the concentrations of estrogen receptors, and therefore, are useful as agents for the treatment or prevention of diseases or conditions in which the actions of estrogens and/or estrogen receptors are involved in the etiology or pathology of the disease or condition or contribute to at least one symptom of the disease or condition and wherein such actions of estrogens and/or estrogen receptors are undesirable. In some embodiments, compounds disclosed herein are estrogen receptor degrader compounds.

In one aspect, a compound of Formula (I), (II), or (III), or a pharmaceutically acceptable salt, solvate or prodrug thereof, is useful for the treatment of ER-related diseases or conditions including, but not limited to, ER-α dysfunction associated with cancer (bone cancer, breast cancer, lung cancer, colorectal cancer, endometrial cancer, prostate cancer, ovarian and uterine cancer), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficity hyperactivity disorder (ADHD), dementia, major depressive disorder, psychosis), uterine diseases (e.g. leiomyoma, uterine leiomyoma, endometrial hyperplasia, endometriosis), and reproductive defects (age of menarche, endometriosis, infertility).

In one aspect, described herein are compounds of Formula (I), (II), and (III), pharmaceutically acceptable salts, solvates, metabolites and prodrugs thereof. Compounds described herein are estrogen receptor modulators. In some embodiments, the compound of Formula (I), (II), or (III) is an estrogen receptor antagonist. In some embodiments, the compound of Formula (I), (II), or (III) is an estrogen receptor degrader. In some embodiments, the compound of Formula (I), (II), or (III) is an estrogen receptor antagonist as well as an estrogen receptor degrader. In some embodiments, the compound of Formula (I), (II), or (III) displays minimal or no estrogen receptor agonist activity. In some embodiments, in the context of treating cancers, the compound of Formula (I), (II), or (III) may offer improved therapeutic activity characterized by complete or longer-lasting tumor regression, a lower incidence or rate of development of resistance to treatment, and/or a reduction in tumor invasiveness.

In some embodiments, compounds disclosed herein have high specificity for the estrogen receptor and have desirable, tissue-selective pharmacological activities. Desirable, tissue-selective pharmacological activities include, but are not limited to, ER antagonist activity in breast cells and no ER agonist activity in uterine cells. In some embodiments, compounds disclosed herein are estrogen receptor degraders that display full estrogen receptor antagonist activity with negligible or minimal estrogen receptor agonist activity.

In some embodiments, compounds disclosed herein are estrogen receptor degraders. In some embodiments, compounds disclosed herein are estrogen receptor antagonists. In some embodiments, compounds disclosed herein have minimal or negligible estrogen receptor agonist activity.

In some embodiments, presented herein are compounds selected from active metabolites, tautomers, pharmaceutically acceptable solvates, pharmaceutically acceptable salts or prodrugs of a compound of Formula (I), (II), or (III).

In one aspect, described herein is a compound of Formula (I):

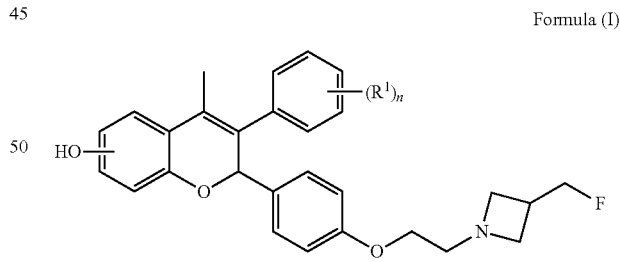

Formula (I)

wherein,
each $R^1$ is independently selected from the group consisting of halogen, —CN, —SO$_2$R$^2$, —OR$^2$, C$_1$-C$_4$alkyl, and C$_1$-C$_4$fluoroalkyl;
each $R^2$ is independently selected from the group consisting of C$_1$-C$_4$alkyl, and C$_1$-C$_4$fluoroalkyl;
n is 0, 1, 2, or 3;
or a pharmaceutically acceptable salt, solvate or prodrug thereof.

In some embodiments, each $R^1$ is independently selected from the group consisting of F, Cl, —CN, —SO$_2$R$^2$, —OR$^2$, —CH$_3$, —CH$_2$CH$_3$, —CF$_3$, and —CH$_2$CF$_3$; each $R^2$ is independently selected from the group consisting of —CH₃, —CH₂CH₃, —CF₃, and —CH₂CF₃.

In some embodiments, each $R^1$ is independently selected from the group consisting of F, Cl, —CN, —CF₃, —OCH₃, and —OCF₃.

In some embodiments, the compound of Formula (I) has the following structure:

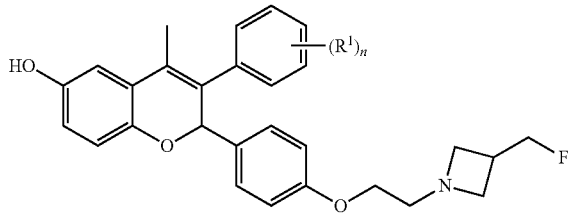

or a pharmaceutically acceptable salt, solvate or prodrug thereof.

In some embodiments, the compound of Formula (I) has the following structure:

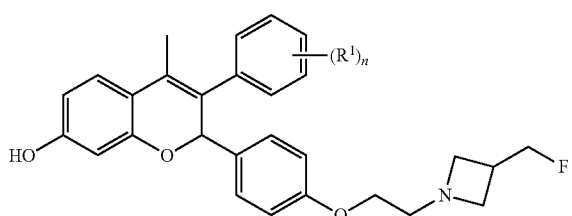

or a pharmaceutically acceptable salt, solvate or prodrug thereof.

In some embodiments, n is 1.

In some embodiments, the compound of Formula (I) has the following structure:

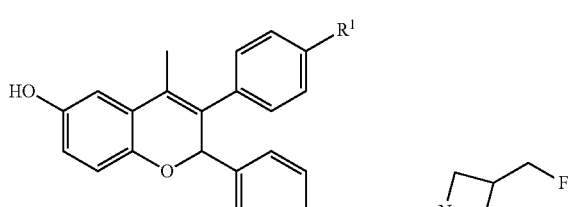

or a pharmaceutically acceptable salt, solvate or prodrug thereof.

In some embodiments, the compound of Formula (I) has the following structure:

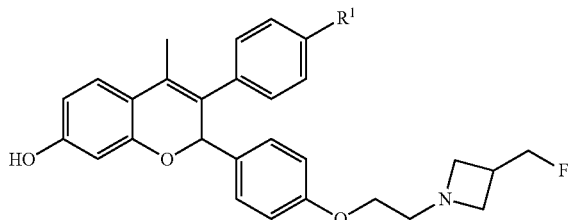

or a pharmaceutically acceptable salt, solvate or prodrug thereof.

In some embodiments, $R^1$ is F. In some embodiments, $R^1$ is CN.

In some embodiments, n is 2.

In some embodiments, the compound of Formula (I) has the following structure:

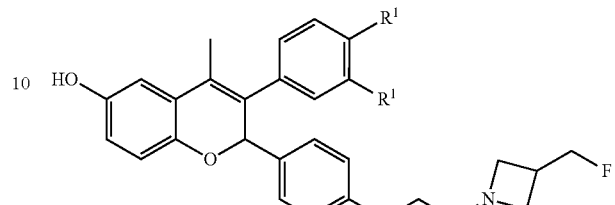

or a pharmaceutically acceptable salt, solvate or prodrug thereof.

In some embodiments, the compound of Formula (I) has the following structure:

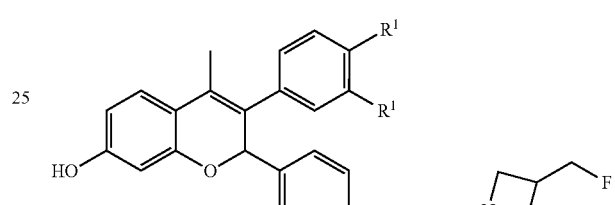

or a pharmaceutically acceptable salt, solvate or prodrug thereof.

In some embodiments, n is 3.

In some embodiments, the compound of Formula (I) has the following structure:

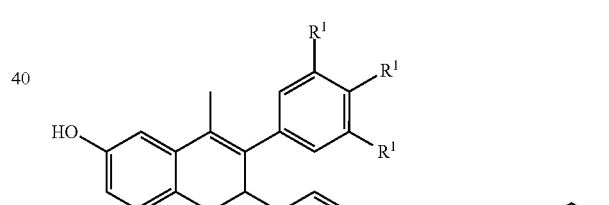

or a pharmaceutically acceptable salt, solvate or prodrug thereof.

In some embodiments, the compound of Formula (I) has the following structure:

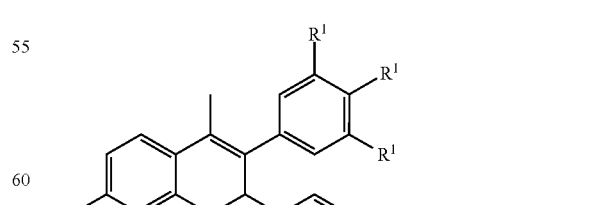

or a pharmaceutically acceptable salt, solvate or prodrug thereof.

In another aspect, described herein is a pharmaceutically acceptable salt of a compound of Formula (I). In some embodiments, the pharmaceutically acceptable salt of the compound is an acid addition salt. In some embodiments, the pharmaceutically acceptable salt of the compound is a hydrochloric acid salt, a hydrobromic acid salt, a sulfuric acid salt, a phosphoric acid salt, a metaphosphoric acid salt, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a L-malic acid salt, a maleic acid salt, an oxalic acid salt, a fumaric acid salt, a trifluoroacetic acid salt, a tartaric acid salt, a L-tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, or a valproic acid salt. In some embodiments, the pharmaceutically acceptable salt of the compound is a hydrochloric acid salt. In some embodiments, the pharmaceutically acceptable salt of the compound is formed by reacting the compound with an inorganic acid. In some embodiments, the pharmaceutically acceptable salt of the compound is formed by reacting the compound with an inorganic acid, wherein the inorganic acid is hydrochloric acid, hydrobromic acid, sulfuric acid, phosphoric acid, or metaphosphoric acid. In some embodiments, the pharmaceutically acceptable salt of the compound is formed by reacting the compound with an organic acid. In some embodiments, the pharmaceutically acceptable salt of the compound is formed by reacting the compound with an organic acid, wherein the organic acid is acetic acid, propionic acid, hexanoic acid, cyclopentanepropionic acid, glycolic acid, pyruvic acid, lactic acid, malonic acid, succinic acid, malic acid, L-malic acid, maleic acid, oxalic acid, fumaric acid, trifluoroacetic acid, tartaric acid, L-tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, or valproic acid. In some embodiments, described herein is a hydrochloride salt of a compound that has the structure of Formula (I).

In another aspect, described herein is a prodrug of a compound of Formula (I). In yet another aspect, described herein is a pharmaceutically acceptable salt of a prodrug of a compound of Formula (I). In some embodiments, the pharmaceutically acceptable salt of the prodrug of a compound of Formula (I) is a hydrochloride salt.

In yet another aspect, described herein is a pharmaceutical composition comprising a compound of Formula (I) or a pharmaceutically acceptable salt or prodrug thereof. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a solution, an emulsion, an ointment, or a lotion.

In another aspect, described herein is a compound that has the following structure of Formula (II):

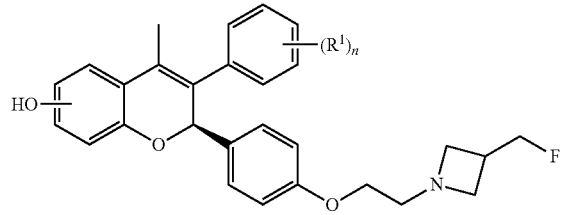

Formula (II)

wherein,
each $R^1$ is independently selected from the group consisting of halogen, —CN, —SO$_2$R$^2$, —OR$^2$, C$_1$-C$_4$alkyl, and C$_1$-C$_4$fluoroalkyl;
each $R^2$ is independently selected from the group consisting of C$_1$-C$_4$alkyl, and C$_1$-C$_4$fluoroalkyl;
n is 0, 1, 2, or 3;
or a pharmaceutically acceptable salt, solvate or prodrug thereof.

In some embodiments, each $R^1$ is independently selected from the group consisting of F, Cl, —CN, —SO$_2$R$^2$, —OR$^2$, —CH$_3$, —CH$_2$CH$_3$, —CF$_3$, and —CH$_2$CF$_3$; each $R^2$ is independently selected from the group consisting of —CH$_3$, —CH$_2$CH$_3$, —CF$_3$, and —CH$_2$CF$_3$.

In some embodiments, each $R^1$ is independently selected from the group consisting of F, Cl, —CN, —CF$_3$, —OCH$_3$, and —OCF$_3$.

In some embodiments, the compound of Formula (II) has the following structure:

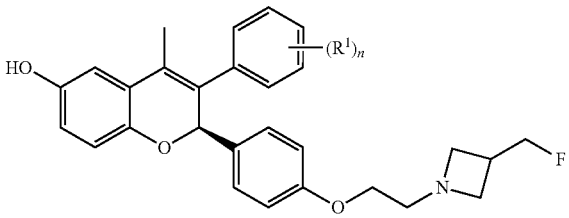

or a pharmaceutically acceptable salt, solvate or prodrug thereof.

In some embodiments, the compound of Formula (II) has the following structure:

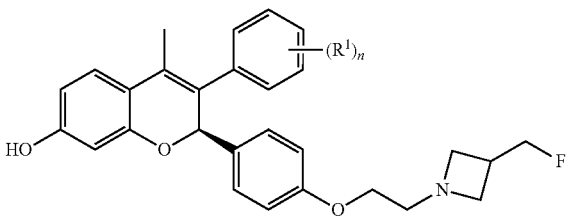

or a pharmaceutically acceptable salt, solvate or prodrug thereof.

In some embodiments, n is 1.

In some embodiments, the compound of Formula (II) has the following structure:

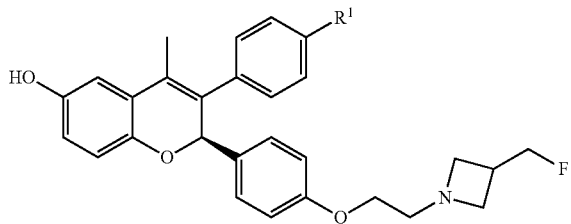

or a pharmaceutically acceptable salt, solvate or prodrug thereof.

In some embodiments, the compound of Formula (II) has the following structure:

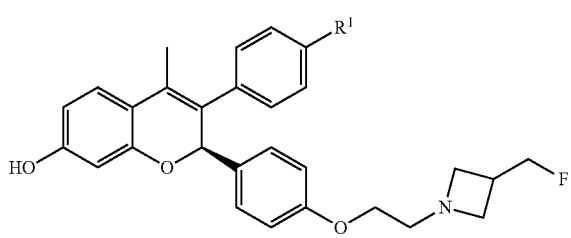

or a pharmaceutically acceptable salt, solvate or prodrug thereof.

In some embodiments, $R^1$ is F. In some embodiments, $R^1$ is CN.

In some embodiments, n is 2.

In some embodiments, the compound of Formula (II) has the following structure:

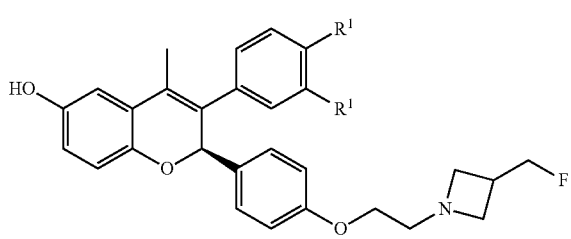

or a pharmaceutically acceptable salt, solvate or prodrug thereof.

In some embodiments, the compound of Formula (II) has the following structure:

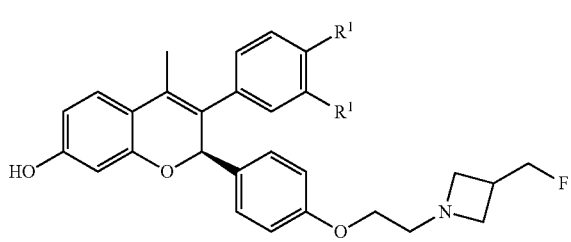

or a pharmaceutically acceptable salt, solvate or prodrug thereof.

In some embodiments, n is 3.

In some embodiments, the compound of Formula (II) has the following structure:

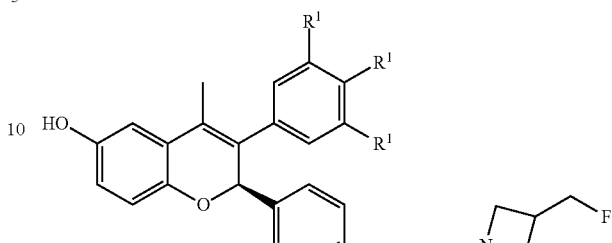

or a pharmaceutically acceptable salt, solvate or prodrug thereof.

In some embodiments, the compound of Formula (II) has the following structure:

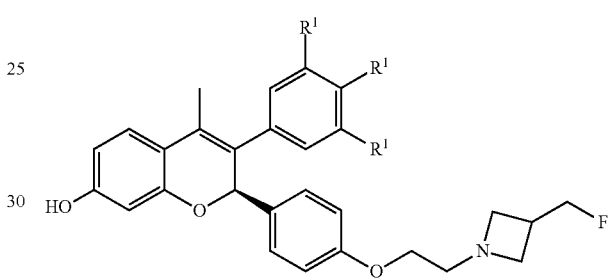

or a pharmaceutically acceptable salt, solvate or prodrug thereof.

Also described herein is a pharmaceutically acceptable salt of a compound of Formula (II). In some embodiments, the pharmaceutically acceptable salt of the compound is an acid addition salt. In some embodiments, the pharmaceutically acceptable salt of the compound is a hydrochloric acid salt, a hydrobromic acid salt, a sulfuric acid salt, a phosphoric acid salt, a metaphosphoric acid salt, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a L-malic acid salt, a maleic acid salt, an oxalic acid salt, a fumaric acid salt, a trifluoroacetic acid salt, a tartaric acid salt, a L-tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, or a valproic acid salt. In some embodiments, the pharmaceutically acceptable salt of the compound is a hydrochloric acid salt. In some embodiments, the pharmaceutically acceptable salt of the compound is formed by reacting the compound with an inorganic acid. In some embodiments, the pharmaceutically acceptable salt of the compound is formed by reacting the compound with an inorganic acid, wherein the inorganic acid is hydrochloric acid, hydrobromic acid, sulfuric acid, phosphoric acid, or metaphosphoric acid. In some embodiments, the pharmaceutically acceptable salt of the compound is formed by reacting the compound with an organic acid. In some embodiments, the pharmaceutically acceptable salt of the compound is formed by reacting the compound with an organic acid, wherein the organic acid is acetic acid, propionic acid, hexanoic acid, cyclopentanepropionic acid, glycolic acid, pyruvic acid, lactic acid, malonic acid, succinic acid, malic acid, L-malic acid, maleic acid, oxalic acid, fumaric acid, trifluoroacetic acid, tartaric acid, L-tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, or valproic acid. In some embodiments, described herein is a hydrochloride salt of a compound that has the structure of Formula (II).

Also described herein is a prodrug of a compound of Formula (II). Also described herein is a pharmaceutically acceptable salt of a prodrug of a compound of Formula (II). In some embodiments, the pharmaceutically acceptable salt of the prodrug of the compound of Formula (II) is a hydrochloride salt.

In another aspect, described herein is a pharmaceutical composition comprising a compound of Formula (II) or a pharmaceutically acceptable salt or prodrug thereof. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a solution, an emulsion, an ointment, or a lotion. In some embodiments, the enantiomeric ratio of the compound of Formula (II), or a pharmaceutically acceptable salt or prodrug thereof, is greater than 90:10. In some embodiments, the enantiomeric ratio of the compound of Formula (II), or a pharmaceutically acceptable salt or prodrug thereof, is greater than 95:5. In some embodiments, the enantiomeric ratio of the compound of Formula (II), or a pharmaceutically acceptable salt or prodrug thereof, is greater than 99:1.

In another aspect, described herein is a compound that has the following structure of Formula (III):

Formula (III)

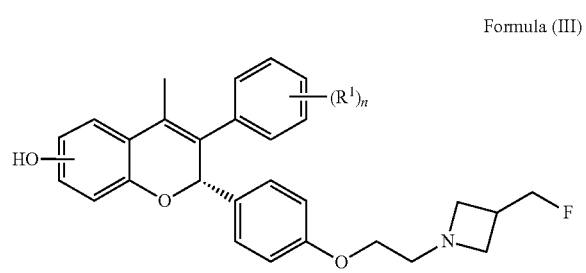

wherein,
each $R^1$ is independently selected from the group consisting of halogen, —CN, —SO$_2$R$^2$, —OR$^2$, C$_1$-C$_4$alkyl, and C$_1$-C$_4$fluoroalkyl;
each $R^2$ is independently selected from the group consisting of C$_1$-C$_4$alkyl, and C$_1$-C$_4$fluoroalkyl;
n is 0, 1, 2, or 3;
or a pharmaceutically acceptable salt, solvate or prodrug thereof.

In some embodiments, each $R^1$ is independently selected from the group consisting of F, Cl, —CN, —SO$_2$R$^2$, —OR$^2$, —CH$_3$, —CH$_2$CH$_3$, —CF$_3$, and —CH$_2$CF$_3$; each $R^2$ is independently selected from the group consisting of —CH$_3$, —CH$_2$CH$_3$, —CF$_3$, and —CH$_2$CF$_3$.

In some embodiments, each $R^1$ is independently selected from the group consisting of F, Cl, —CN, —CF$_3$, —OCH$_3$, and —OCF$_3$.

In some embodiments, the compound of Formula (III) has the following structure:

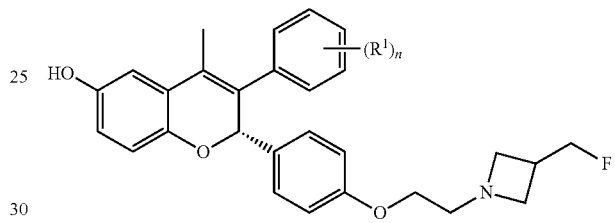

or a pharmaceutically acceptable salt, solvate or prodrug thereof.

In some embodiments, the compound of Formula (III) has the following structure:

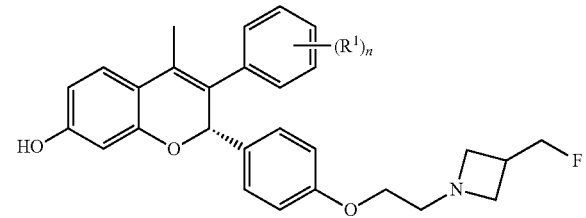

or a pharmaceutically acceptable salt, solvate or prodrug thereof.

In some embodiments, n is 1.

In some embodiments, the compound of Formula (III) has the following structure:

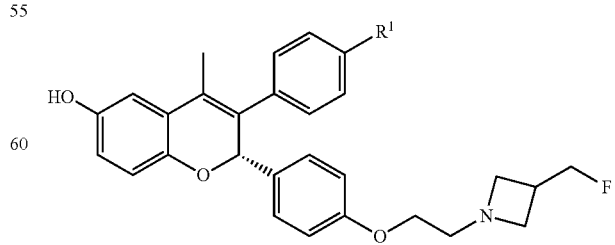

or a pharmaceutically acceptable salt, solvate or prodrug thereof.

In some embodiments, the compound of Formula (III) has the following structure:

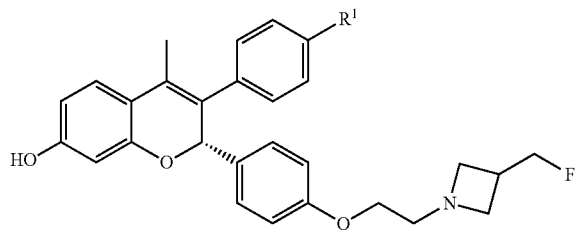

or a pharmaceutically acceptable salt, solvate or prodrug thereof.

In some embodiments, $R^1$ is F. In some embodiments, $R^1$ is CN.

In some embodiments, n is 2.

In some embodiments, the compound of Formula (III) has the following structure:

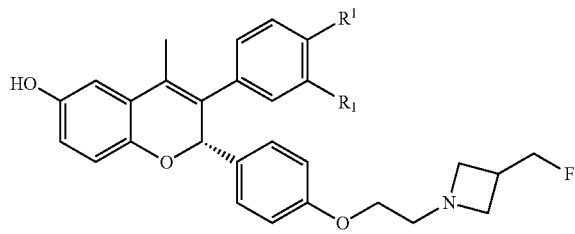

or a pharmaceutically acceptable salt, solvate or prodrug thereof.

In some embodiments, the compound of Formula (III) has the following structure:

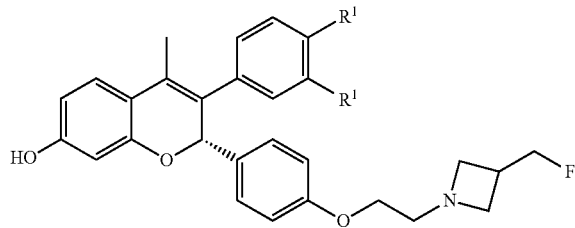

or a pharmaceutically acceptable salt, solvate or prodrug thereof.

In some embodiments, n is 3.

In some embodiments, the compound of Formula (III) has the following structure:

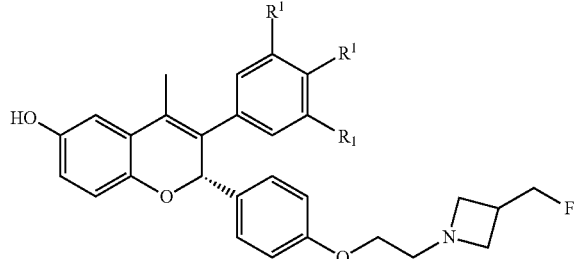

or a pharmaceutically acceptable salt, solvate or prodrug thereof.

In some embodiments, the compound of Formula (III) has the following structure:

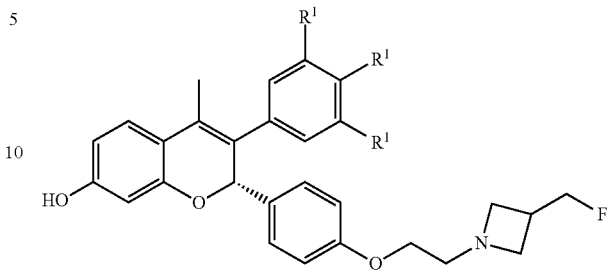

or a pharmaceutically acceptable salt, solvate or prodrug thereof.

Also described herein is a pharmaceutically acceptable salt of a compound of Formula (III). In some embodiments, the pharmaceutically acceptable salt of the compound is an acid addition salt. In some embodiments, the pharmaceutically acceptable salt of the compound is a hydrochloric acid salt, a hydrobromic acid salt, a sulfuric acid salt, a phosphoric acid salt, a metaphosphoric acid salt, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a L-malic acid salt, a maleic acid salt, an oxalic acid salt, a fumaric acid salt, a trifluoroacetic acid salt, a tartaric acid salt, a L-tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, or a valproic acid salt. In some embodiments, the pharmaceutically acceptable salt of the compound is a hydrochloric acid salt. In some embodiments, the pharmaceutically acceptable salt of the compound is formed by reacting the compound with an inorganic acid. In some embodiments, the pharmaceutically acceptable salt of the compound is formed by reacting the compound with an inorganic acid, wherein the inorganic acid is hydrochloric acid, hydrobromic acid, sulfuric acid, phosphoric acid, or metaphosphoric acid. In some embodiments, the pharmaceutically acceptable salt of the compound is formed by reacting the compound with an organic acid. In some embodiments, the pharmaceutically acceptable salt of the compound is formed by reacting the compound with an organic acid, wherein the organic acid is acetic acid, propionic acid, hexanoic acid, cyclopentanepropionic acid, glycolic acid, pyruvic acid, lactic acid, malonic acid, succinic acid, malic acid, L-malic acid, maleic acid, oxalic acid, fumaric acid, trifluoroacetic acid, tartaric acid, L-tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]

oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, or valproic acid. In some embodiments, described herein is a hydrochloride salt of a compound that has the structure of Formula (III).

Also described herein is a prodrug of a compound of Formula (III). Also described herein is a pharmaceutically acceptable salt of a prodrug of a compound of Formula (III). In some embodiments, the pharmaceutically acceptable salt of the prodrug of a compound of Formula (III) is a hydrochloride salt.

In another aspect, described herein is a pharmaceutical composition comprising a compound of Formula (III) or a pharmaceutically acceptable salt or prodrug thereof. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a solution, an emulsion, an ointment, or a lotion. In some embodiments, the enantiomeric ratio of the compound of Formula (III), or a pharmaceutically acceptable salt or prodrug thereof, is greater than 90:10. In some embodiments, the enantiomeric ratio of the compound of Formula (III), or a pharmaceutically acceptable salt or prodrug thereof, is greater than 95:5. In some embodiments, the enantiomeric ratio of the compound of Formula (III), or a pharmaceutically acceptable salt or prodrug thereof, is greater than 99:1.

In some embodiments, the pharmaceutical composition described herein further comprises, in addition to the compound of Formula (I), (II), or (III), one or more additional therapeutically active agents selected from: corticosteroids, anti-emetic agents, analgesics, anti-cancer agents, anti-inflammatories, kinase inhibitors, antibodies, HSP90 inhibitors, histone deacetylase (HDAC) inhibitors, poly ADP-ribose polymerase (PARP) inhibitors, and aromatase inhibitors.

In some embodiments, provided herein is a method comprising administering a compound of Formula (I), (II), or (III), or a pharmaceutically acceptable salt or prodrug thereof, to a human with a diseases or condition that is estrogen sensitive, estrogen receptor meditated or estrogen receptor dependent. In some embodiments, the human is already being administered one or more additional therapeutically active agents other than a compound of Formula (I), (II), or (III), or a pharmaceutically acceptable salt or prodrug thereof. In some embodiments, the method further comprises administering one or more additional therapeutically active agents other than a compound of Formula (I), (II), or (III), or a pharmaceutically acceptable salt or prodrug thereof.

In some embodiments, the one or more additional therapeutically active agents other than a compound of Formula (I), (II), or (III), or a pharmaceutically acceptable salt or prodrug thereof, are selected from: corticosteroids, anti-emetic agents, analgesics, anti-cancer agents, anti-inflammatories, kinase inhibitors, antibodies, HSP90 inhibitors, histone deacetylase (HDAC) inhibitors, and aromatase inhibitors.

Pharmaceutical formulations described herein are administered to a mammal in a variety of ways, including but not limited to, oral, parenteral (e.g., intravenous, subcutaneous, intramuscular), buccal, topical or transdermal administration routes. The pharmaceutical formulations described herein include, but are not limited to, aqueous liquid dispersions, self-emulsifying dispersions, solid solutions, liposomal dispersions, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compound of Formula (I), (II), or (III), or a pharmaceutically acceptable salt, solvate or prodrug thereof, is administered orally.

In some embodiments, the compound of Formula (I), (II), or (III), or a pharmaceutically acceptable salt, solvate or prodrug thereof, is administered systemically.

In some embodiments, the compound of Formula (I), (II), or (III), or a pharmaceutically acceptable salt, solvate or prodrug thereof, is administered intravenously.

In some embodiments, the compound of Formula (I), (II), or (III), or a pharmaceutically acceptable salt, solvate or prodrug thereof, is administered subcutaneously.

In some embodiments, the compound of Formula (I), (II), or (III), or a pharmaceutically acceptable salt, solvate or prodrug thereof, is administered topically. In such embodiments, the compound of Formula (I), (II), or (III), or a pharmaceutically acceptable salt, solvate or prodrug thereof, is formulated into a variety of topically administrable compositions, such as solutions, suspensions, lotions, gels, pastes, shampoos, scrubs, rubs, smears, medicated sticks, medicated bandages, balms, creams or ointments. In some embodiments, the compound of Formula (I), (II), or (III), or a pharmaceutically acceptable salt, solvate or prodrug thereof, is administered topically to the skin of mammal.

In another aspect is the use of a compound of Formula (I), (II), or (III), or a pharmaceutically acceptable salt, solvate or prodrug thereof, for treating a disease, disorder or conditions in which the activity of estrogen receptors contributes to the pathology and/or symptoms of the disease or condition. In one aspect, the disease or condition is any of the diseases or conditions specified herein.

In another aspect is the use of a compound of Formula (I), (II), or (III), or a pharmaceutically acceptable salt, solvate or prodrug thereof, in the manufacture of a medicament for treating a disease, disorder or conditions in which the activity of estrogen receptors contributes to the pathology and/or symptoms of the disease or condition. In one aspect, the disease or condition is any of the diseases or conditions specified herein.

In any of the aforementioned aspects are further embodiments in which the effective amount of the compound of Formula (I), (II), or (III), or a pharmaceutically acceptable salt thereof, solvate or prodrug thereof is: (a) systemically administered to the mammal; and/or (b) administered orally to the mammal; and/or (c) intravenously administered to the mammal; and/or (d) administered by injection to the mammal; and/or (e) administered topically to the mammal; and/or (f) adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of reducing ER activation in a mammal comprising administering to the mammal at least one compound having the structure of Formula (I), (II), or (III), or a pharmaceutically acceptable salt, solvate or prodrug thereof. In some embodiments, the method comprises reducing ER activation in breast cells, lung cells, ovarian cells, colon cells, prostate cells, endometrial cells, or uterine cells in the mammal. In some embodiments, the method comprises reducing ER activation in breast cells, ovarian cells, colon cells, prostate cells, endometrial cells, or uterine cells in the mammal. In some embodiments, the method of reducing ER activation in the mammal comprises reducing the binding of estrogens to estrogen receptors in the mammal. In some embodiments, the method of reducing ER activation in the mammal comprises reducing ER concentrations in the mammal.

In one aspect is the use of a compound of Formula (I), (II), or (III), or a pharmaceutically acceptable salt, solvate or prodrug thereof, in the treatment or prevention of diseases or conditions of the uterus in a mammal. In some embodiments, the disease or condition of the uterus is leiomyoma, uterine leiomyoma, endometrial hyperplasia, or endometriosis. In some embodiments, the disease or condition of the uterus is a cancerous disease or condition of the uterus. In some other embodiments, the disease or condition of the uterus is a non-cancerous disease or condition of the uterus.

In one aspect is the use of a compound of Formula (I), (II), or (III), or a pharmaceutically acceptable salt, solvate or prodrug thereof, in the manufacture of a medicament for the treatment of diseases or conditions that are estrogen sensitive, estrogen receptor dependent or estrogen receptor mediated. In some embodiments, the disease or condition is breast cancer, lung cancer, ovarian cancer, colon cancer, prostate cancer, endometrial cancer, or uterine cancer. In some embodiments, the disease or condition is described herein.

In some cases disclosed herein is the use of a compound of Formula (I), (II), or (III), or a pharmaceutically acceptable salt, solvate or prodrug thereof, in the treatment or prevention of diseases or conditions that are estrogen sensitive, estrogen receptor dependent or estrogen receptor mediated. In some embodiments, the disease or condition is described herein.

In any of the embodiments disclosed herein, the mammal is a human.

In some embodiments, compounds provided herein are used to diminish, reduce, or eliminate the activity of estrogen receptors.

Articles of manufacture, which include: packaging material; a compound of Formula (I), (II), or (III), or a pharmaceutically acceptable salt, active metabolite, prodrug, or pharmaceutically acceptable solvate thereof, or composition thereof, within the packaging material; and a label that indicates that the compound or pharmaceutically acceptable salt, active metabolite, prodrug, or pharmaceutically acceptable solvate thereof, or composition thereof, or composition thereof, is used for reducing, diminishing or eliminating the effects of estrogen receptors, or for the treatment, prevention or amelioration of one or more symptoms of a disease or condition that would benefit from a reduction or elimination of estrogen receptor activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

Estrogen receptor alpha (ER-α; NR3A1) and estrogen receptor beta (ER-β; NR3A2) are steroid hormone receptors, which are members of the large nuclear receptor superfamily. Nuclear receptors share a common modular structure, which minimally includes a DNA binding domain (DBD) and a ligand binding domain (LBD). Steroid hormone receptors are soluble, intracellular proteins that act as ligand-regulated transcription factors. Vertebrates contain five closely related steroid hormone receptors (estrogen receptor, androgen receptor, progesterone receptor, glucocorticoid receptor, mineralcorticoid receptor), which regulate a wide spectrum of reproductive, metabolic and developmental activities. The activities of ER are controlled by the binding of endogenous estrogens, including 17β-estradiol and estrones.

The ER-α gene is located on 6q25.1 and encodes a 595 AA protein. The ER-β gene resides on chromosome 14q23.3 and produces a 530 AA protein. However, due to alternative splicing and translation start sites, each of these genes can give rise to multiple isoforms. In addition to the DNA binding domain (called C domain) and ligand binding domain (E domain) these receptors contain an N-terminal (A/B) domain, a hinge (D) domain that links the C and E domains, and a C-terminal extension (F domain) (Gronemeyer and Laudet; Protein Profile 2: 1173-1308, 1995). While the C and E domains of ER-α and ER-β are quite conserved (95% and 55% amino acid identity, respectively), conservation of the A/B, D and F domains is poor (below 30% amino acid identity). Both receptors are involved in the regulation and development of the female reproductive tract but also play various roles in the central nervous system, cardiovascular systems and bone metabolism.

The ligand binding pocket of steroid hormone receptors is deeply buried within the ligand binding domain. Upon binding, the ligand becomes part of the hydrophobic core of this domain. Consequently most steroid hormone receptors are instable in the absence of hormone and require assistance from chaperones, such as Hsp90, in order to maintain hormone-binding competency. The interaction with Hsp90 also controls nuclear translocation of these receptors. Ligand-binding stabilizes the receptor and initiates sequential conformational changes that release the chaperones, alter the interactions between the various receptor domains and remodel protein interaction surfaces that allow these receptors to translocate into the nucleus, bind DNA and engage in interactions with chromatin remodeling complexes and the transcriptional machinery. Although ER can interact with Hsp90, this interaction is not required for hormone binding and, dependent on the cellular context, apo-ER can be both cytoplasmic and nuclear. Biophysical studies indicated that DNA binding rather than ligand binding contributes to the stability of the receptor (Greenfield et al., Biochemistry 40: 6646-6652, 2001).

ER can interact with DNA either directly by binding to a specific DNA sequence motif called estrogen response element (ERE) (classical pathway), or indirectly via protein-protein interactions (nonclassical pathway) (Welboren et al., Endocrine-Related Cancer 16: 1073-1089, 2009). In the nonclassical pathway, ER has been shown to tether to other transcription factors including SP-1, AP-1 and NF-κB. These interactions appear to play critical roles in the ability of ER to regulate cell proliferation and differentiation.

Both types of ER DNA interactions can result in gene activation or repression dependent on the transcriptional coregulators that are recruited by the respective ER-ERE complex (Klinge, Steroid 65: 227-251, 2000). The recruitment of coregulators is primarily mediated by two protein interaction surfaces, the AF2 and AF1. AF2 is located in the ER E-domain and its conformation is directly regulated by the ligand (Brzozowski et al., Nature 389: 753-758, 1997). Full agonists appear to promote the recruitment of co-activators, whereas weak agonists and antagonists facilitate the binding of co-repressors. The regulation of protein with the AF1 is less well understood but can be controlled by serine phosphorylation (Ward and Weigel, Biofactors 35: 528-536, 2009). One of the involved phosphorylation sites (S 118) appears to control the transcriptional activity of ER in the presence of antagonists such as tamoxifen, which plays an important role in the treatment of breast cancer. While full agonists appear to arrest ER in certain conformation, weak agonists tend to maintain ER in equilibrium between different conformations, allowing cell-dependent differences in co-regulator repertoires to modulate the activity of ER in a cell-dependent manner (Tamrazi et al., Mol. Endocrinol. 17: 2593-2602, 2003). Interactions of ER with DNA are dynamic and include, but are not limited to, the degradation of ER by the proteasome (Reid et al., Mol Cell 11: 695-707, 2003). The degradation of ER with ligands provides an attractive treatment strategy for disease or conditions that estrogen-senstitive and/or resistant to available anti-hormonal treatments.

ER signaling is crucial for the development and maintenance of female reproductive organs including breasts, ovulation and thickening of the endometrium. ER signaling also has a role in bone mass, lipid metabolism, cancers, etc. About 70% of breast cancers express ER-α (ER-α positive) and are dependent on estrogens for growth and survival. Other cancers also are thought to be dependent on ER-α signaling for growth and survival, such as for example ovarian and endometrial cancers. The ER-α antagonist tamoxifen has been used to treat early and advanced ER-α positive breast cancer in both pre- and post-menopausal women. Fulvestrant (Faslodex™) a steroid-based ER antagonist is used to treat breast cancer in women which have progressed despite therapy with tamoxifen. Steroidal and non-steroidal aromatase inhibitors are also used to treat cancers in humans. In some embodiments, the steroidal and non-steroidal aromatase inhibitors block the production of estrogen from androstenedione and testosterone in post-menopausal women, thereby blocking ER dependent growth in the cancers. In addition to these anti-hormonal agents, progressive ER positive breast cancer is treated in some cases with a variety of other chemotherapeutics, such as for example, the anthracylines, platins, taxanes. In some cases, ER positive breast cancers that harbor genetic amplication of the ERB-B/HER2 tyrosine kinase receptor are treated with the monoclonal antibody trastuzumab (Herceptin™) or the small molecule pan-ERB-B inhibitor lapatinib. Despite this battery of anti-hormonal, chemotherapeutic and small-molecule and antibody-based targeted therapies, many women with ER-α positive breast develop progressive metastatic disease and are in need of new therapies. Importantly, the majority of ER positive tumors that progress on existing anti-hormonal, as well as and other therapies, are thought to remain dependent on ER-α for growth and survival. Thus, there is a need for new ER-α targeting agents that have activity in the setting of metastatic disease and acquired resistance. In one aspect, described herein are compounds that are selective estrogen receptor modulators (SERMs). In specific embodiments, the SERMs described herein are selective estrogen receptor degraders (SERDs). In some embodiments, in cell-based assays the compounds described herein result in a reduction in steady state ER-α levels (i.e. ER degradation) and are useful in the treatment of estrogen sensitive diseases or conditions and/or diseases or conditions that have developed resistant to anti-hormonal therapies.

Given the central role of ER-α in breast cancer development and progression, compounds disclosed herein are useful in the treatment of breast cancer, either alone or in combination with other agent agents that can modulate other critical pathways in breast cancer, including but not limited to those that target IGF1R, EGFR, erB-B2 and 3 the PI3K/AKT/mTOR axis, HSP90, PARP or histone deacetylases.

Given the central role of ER-α in breast cancer development and progression, compounds disclosed herein are useful in the treatment of breast cancer, either alone or in combination with other agent used to treat breast cancer, including but not limited to aromatase inhibitors, anthracylines, platins, nitrogen mustard alkylating agents, taxanes. Illustrative agent used to treat breast cancer, include, but are not limited to, paclitaxel, anastrozole, exemestane, cyclophosphamide, epirubicin, fulvestrant, letrozole, gemcitabine, trastuzumab, pegfilgrastim, filgrastim, tamoxifen, docetaxel, toremifene, vinorelbine, capecitabine, ixabepilone, as well as others described herein.

ER-related diseases or conditions include ER-α dysfunction is associated with cancer (bone cancer, breast cancer, lung cancer, colorectal cancer, endometrial cancer, prostate cancer, ovarian and uterine cancer), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis) and reproductive defects (age of menarche, endometriosis, infertility.

In some embodiments, compounds disclosed herein are used in the treatment of an estrogen receptor dependent or estrogen receptor mediated disease or condition in mammal.

In some embodiments, the estrogen receptor dependent or estrogen receptor mediated disease or condition is selected from cancer, central nervous system (CNS) defects, cardiovascular system defects, hematological system defects, immune and inflammation diseases, susceptibility to infection, metabolic defects, neurological defects, psychiatric defects and reproductive defects.

In some embodiments, the estrogen receptor dependent or estrogen receptor mediated disease or condition is selected from bone cancer, breast cancer, lung cancer, colorectal cancer, endometrial cancer, prostate cancer, ovarian cancer, uterine cancer, alcoholism, migraine, aortic aneurysm, susceptibility to myocardial infarction, aortic valve sclerosis, cardiovascular disease, coronary artery disease, hypertension, deep vein thrombosis, Graves' Disease, arthritis, multiple sclerosis, cirrhosis, hepatitis B, chronic liver disease, bone density, cholestasis, hypospadias, obesity, osteoarthritis, osteopenia, osteoporosis, Alzheimer's disease, Parkinson's disease, migraine, vertigo, anorexia nervosa, attention deficity hyperactivity disorder (ADHD), dementia, major depressive disorder, psychosis, age of menarche, endometriosis, and infertility.

In some embodiments, compounds disclosed herein are used to treat cancer in a mammal. In some embodiments, the cancer is breast cancer, lung cancer, ovarian cancer, endometrial cancer, prostate cancer, or uterine cancer. In some embodiments, the cancer is breast cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In some embodiments, the compound used in any of the methods described herein is an estrogen receptor degrader; is an estrogen receptor antagonist; has minimal or negligible estrogen receptor agonist activity; or combinations thereof.

In some embodiments, methods of treatment with compounds described herein include a treatment regimen that includes administering radiation therapy to the mammal.

In some embodiments, methods of treatment with compounds described herein include administering the compound prior to or following surgery.

In some embodiments, methods of treatment with compounds described herein include administering to the mammal at least one additional anti-cancer agent.

In some embodiments, compounds disclosed herein are used to treat cancer in a mammal, wherein the mammal is chemotherapy-naïve.

In some embodiments, compounds disclosed herein are used in the treatment of cancer in a mammal. In some embodiments, compounds disclosed herein are used to treat cancer in a mammal, wherein the mammal is being treated for cancer with at least one anti-cancer agent. In one embodiment, the cancer is a hormone refractory cancer.

In some embodiments, compounds disclosed herein are used in the treatment or prevention of diseases or conditions of the uterus in a mammal. In some embodiments, the disease or condition of the uterus is leiomyoma, uterine leiomyoma, endometrial hyperplasia, or endometriosis. In some embodiments, the disease or condition of the uterus is a cancerous disease or condition of the uterus. In some other embodiments, the disease or condition of the uterus is a non-cancerous disease or condition of the uterus.

In some embodiments, compounds disclosed herein are used in the treatment of endometriosis in a mammal.

In some embodiments, compounds disclosed herein are used in the treatment of leiomyoma in a mammal. In some embodiments, the leiomyoma is a uterine leiomyoma, esophageal leiomyoma, cutaneous leiomyoma, or small bowel leiomyoma. In some embodiments, compounds disclosed herein are used in the treatment of fibroids in a mammal. In some embodiments, compounds disclosed herein are used in the treatment of uterine fibroids in a mammal.

Compounds

The compounds of Formula (I), (II), and (III), including pharmaceutically acceptable salts, prodrugs, active metabolites and pharmaceutically acceptable solvates thereof, are estrogen receptor modulators. In specific embodiments, the compound is estrogen receptor degrader. In specific embodiments, the compound is an estrogen receptor antagonist. In specific embodiments, the compound is an estrogen receptor degrader and estrogen receptor antagonist with minimal or no estrogen receptor agonist activity.

In some embodiments, compounds disclosed herein are estrogen receptor degraders and estrogen receptor antagonists that exhibit: no estrogen receptor agonism; and/or anti-proliferative activity against breast cancer, ovarian cancer, endometrial cancer, cervical cancer cell lines; and/or maximal anti-proliferative efficacy against breast cancer, ovarian cancer, endometrial cancer, cervical cell lines in-vitro; and/or minimal agonism in the human endometrial (Ishikawa) cell line; and/or no agonism in the human endometrial (Ishikawa) cell line; and/or no agonism in the immature rat uterine assay in-vivo; and/or inverse agonism in the immature rat uterine assay in-vivo; and/or anti-tumor activity in breast cancer, ovarian cancer, endometrial cancer, cervical cancer cell lines in xenograft assays in-vivo or other rodent models of these cancers.

In some embodiments, compounds described herein have reduced or minimal interaction with the hERG (the human Ether-à-go-go-Related Gene) channel and/or show a reduced potential for QT prolongation and/or a reduced risk of ventricular tachyarrhythmias like torsades de pointes.

In some embodiments, the compound of Formula (I), (II), or (III), has reduced or minimal potential to access the hypothalamus and/or have reduced or minimal potential to modulate the Hypothalamic-Pituitary-Ovarian (HPO) axis and/or show a reduced potential to cause hyper-stimulation of the ovaries and/or show a reduced potential for ovary toxicity.

In some embodiments, the compound of Formula (I), (II), or (III), for use in the treatment of a disease or condition in a pre-menopausal woman have reduced or minimal potential to access the hypothalamus and/or have reduced or minimal potential to modulate the Hypothalamic-Pituitary-Ovarian (HPO) axis and/or show a reduced potential to cause hyper-stimulation of the ovaries and/or show a reduced potential for ovary toxicity. In some embodiments, the disease or condition in the pre-menopausal woman is endometriosis. In some embodiments, the disease or condition in the pre-menopausal woman is an uterine disease or condition.

In one aspect, described herein is a compound of Formula (I), or a pharmaceutically acceptable salt, solvate or prodrug thereof:

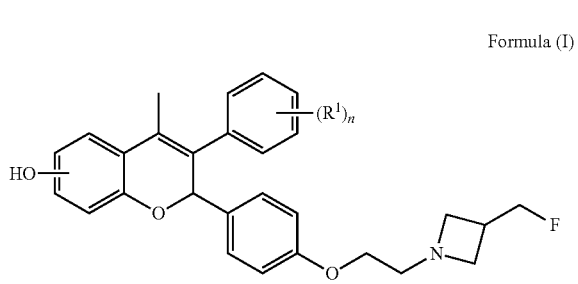

Formula (I)

wherein,
each $R^1$ is independently selected from the group consisting of halogen, —CN, —SO$_2$R$^2$, —OR$^2$, C$_1$-C$_4$ alkyl, and C$_1$-C$_4$ fluoroalkyl;
each $R^2$ is independently selected from the group consisting of C$_1$-C$_4$ alkyl, and C$_1$-C$_4$ fluoroalkyl;
n is 0, 1, 2, or 3;
or a pharmaceutically acceptable salt, solvate or prodrug thereof.

In some embodiments, each $R^1$ is independently selected from the group consisting of F, Cl, —CN, —SO$_2$R$^2$, —OR$^2$, —CH$_3$, —CH$_2$CH$_3$, —CF$_3$, and —CH$_2$CF$_3$; each $R^2$ is independently selected from the group consisting of —CH$_3$, —CH$_2$CH$_3$, —CF$_3$, and —CH$_2$CF$_3$.

In some embodiments, each $R^1$ is independently selected from the group consisting of F, Cl, —CN, —CH$_3$, and —CF$_3$. In some embodiments, each $R^1$ is independently selected from the group consisting of F, Cl, —CN, —SO$_2$CH$_3$, —OCF$_3$, and —CF$_3$. In some embodiments, each $R^1$ is independently selected from the group consisting of F, —CN, and —SO$_2$CH$_3$.

In some embodiments, the compound of Formula (I) has the following structure:

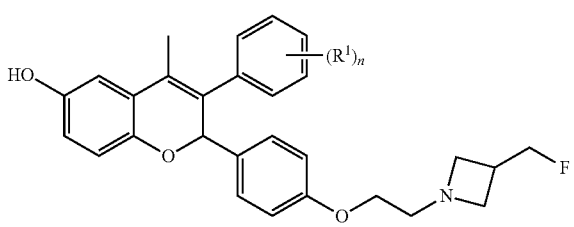

or a pharmaceutically acceptable salt, solvate or prodrug thereof.

In some embodiments, the compound of Formula (I) has the following structure:

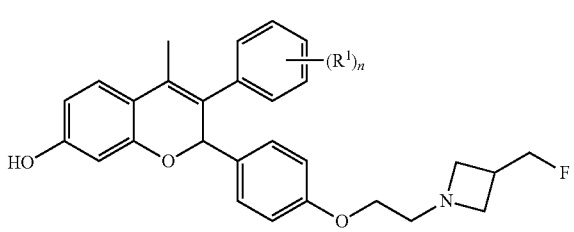

or a pharmaceutically acceptable salt, solvate or prodrug thereof.

In some embodiments, n is 1.
In some embodiments, the compound of Formula (I) has the following structure:

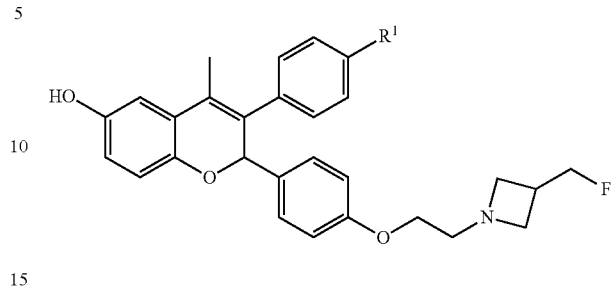

or a pharmaceutically acceptable salt, solvate or prodrug thereof.

In some embodiments, the compound of Formula (I) has the following structure:

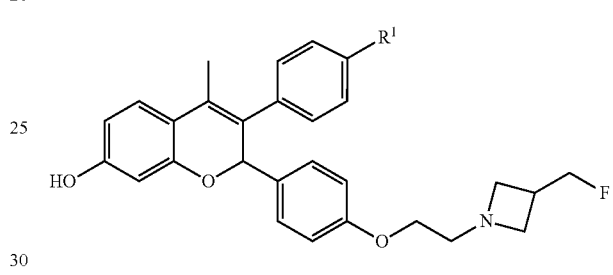

or a pharmaceutically acceptable salt, solvate or prodrug thereof.

In some embodiments, $R^1$ is F. In some embodiments, $R^1$ is CN.

In some embodiments, n is 2.
In some embodiments, the compound of Formula (I) has the following structure:

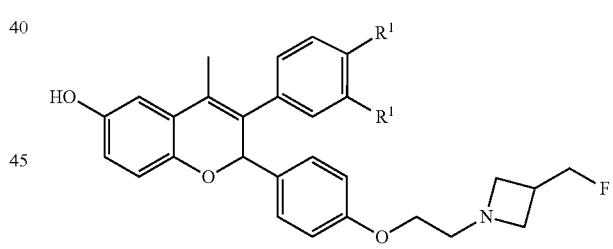

or a pharmaceutically acceptable salt, solvate or prodrug thereof.

In some embodiments, the compound of Formula (I) has the following structure:

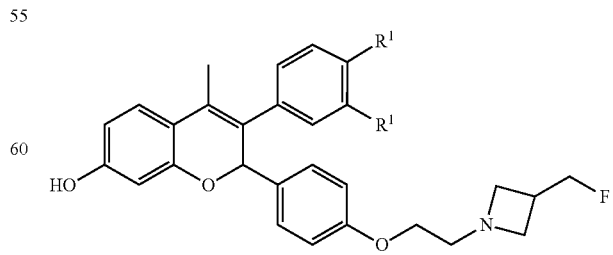

or a pharmaceutically acceptable salt, solvate or prodrug thereof.

In some embodiments, n is 3.

In some embodiments, the compound of Formula (I) has the following structure:

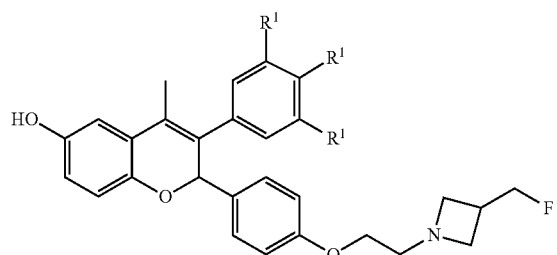

or a pharmaceutically acceptable salt, solvate or prodrug thereof.

In some embodiments, the compound of Formula (I) has the following structure:

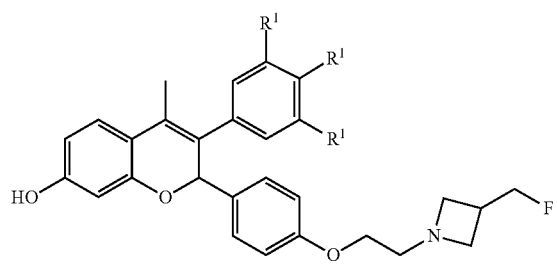

or a pharmaceutically acceptable salt, solvate or prodrug thereof.

In some embodiments, the compound of Formula (I) has one of the following structures:

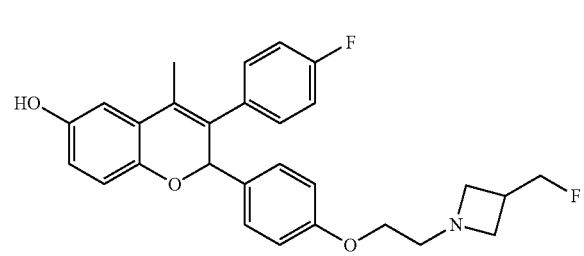

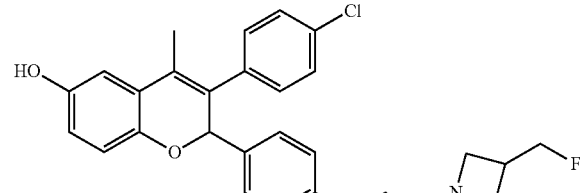

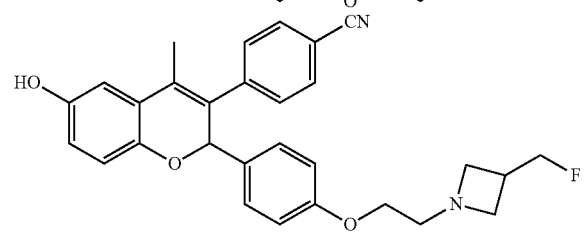

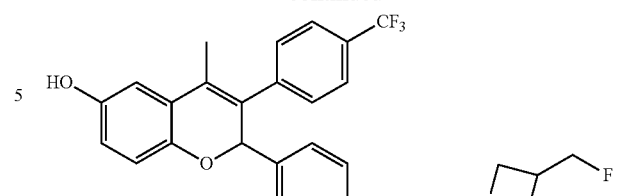

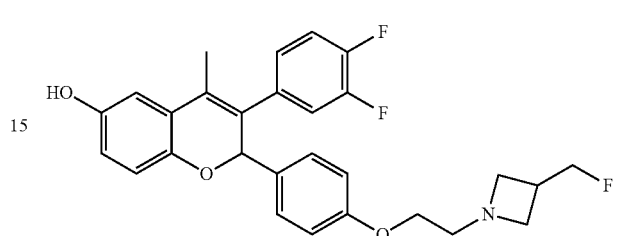

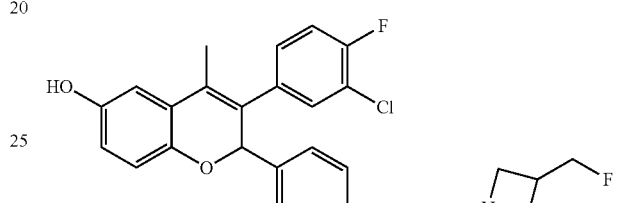

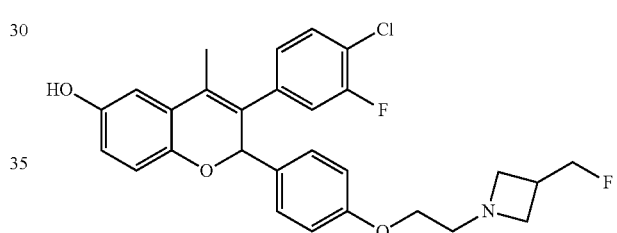

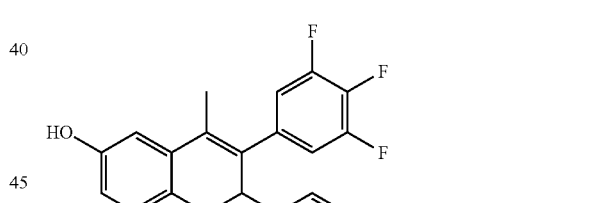

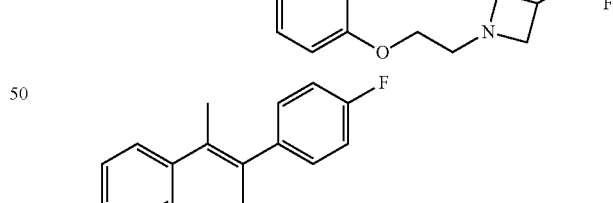

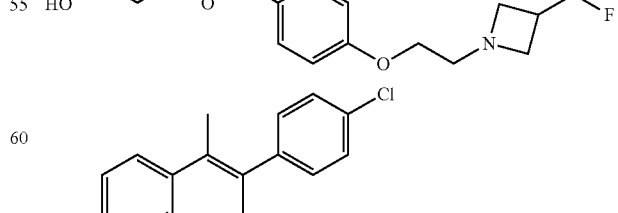

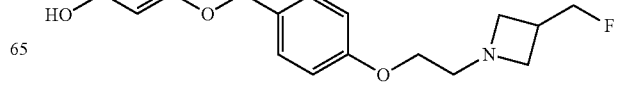

-continued
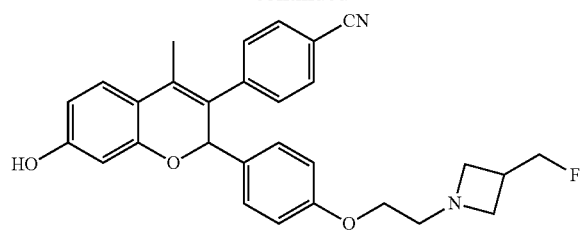
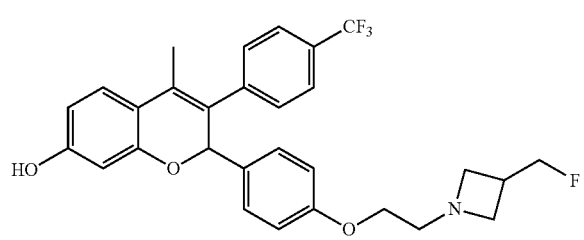
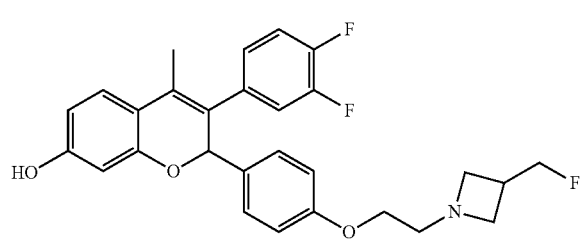
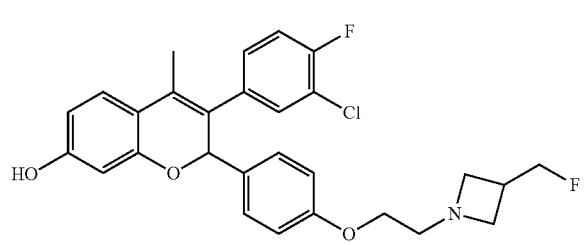
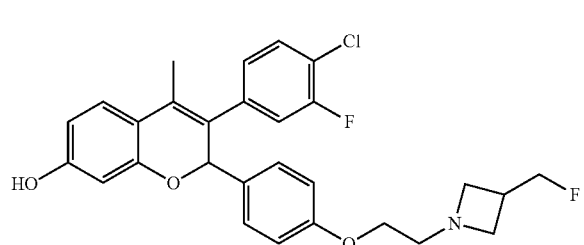
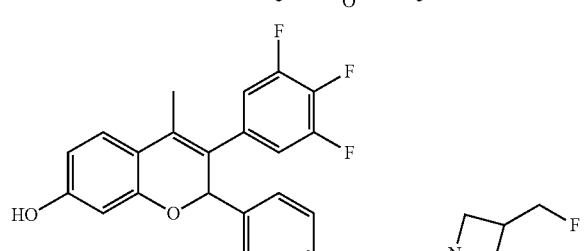
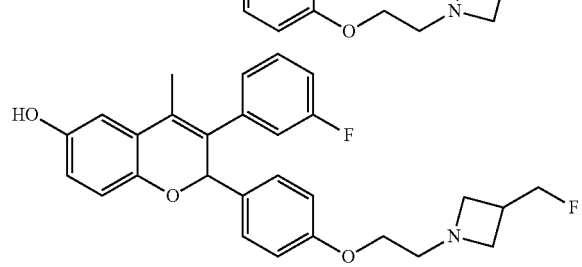
-continued
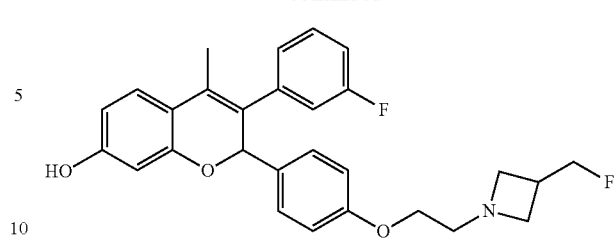
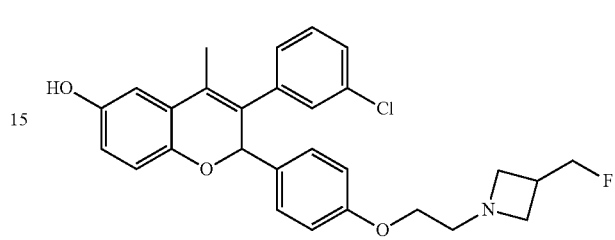
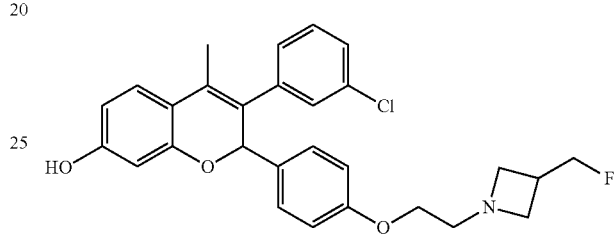
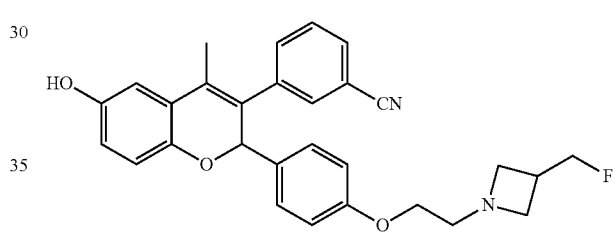
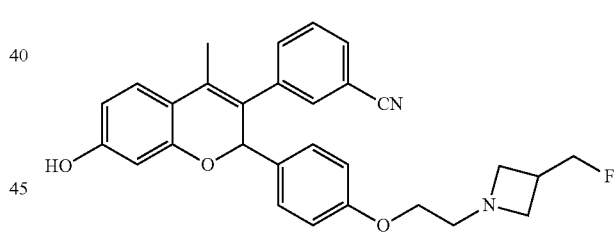
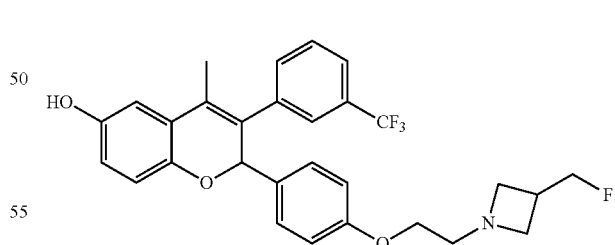
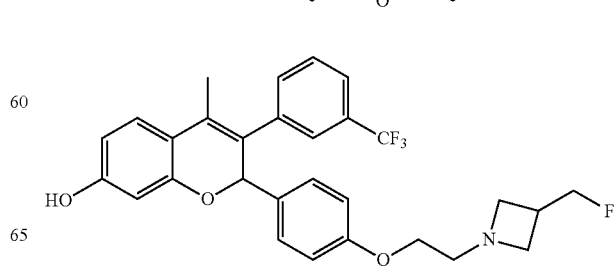

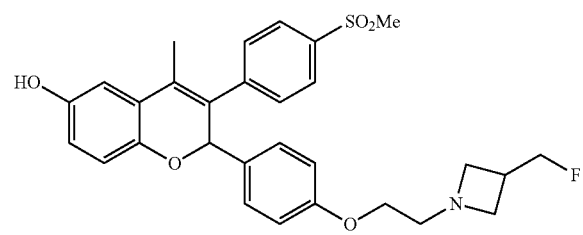
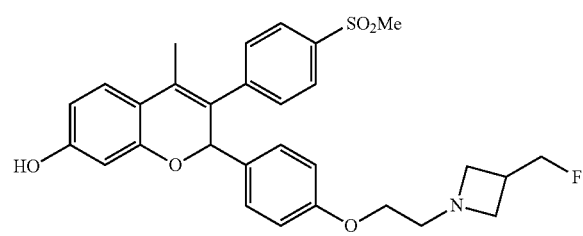
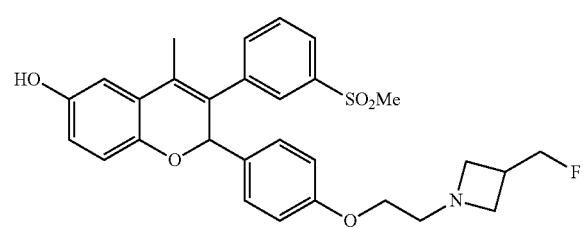
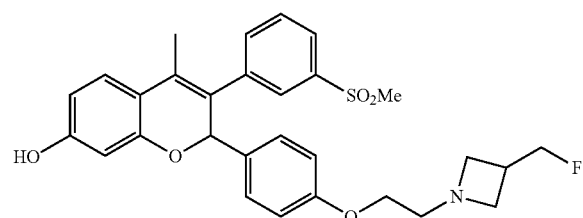
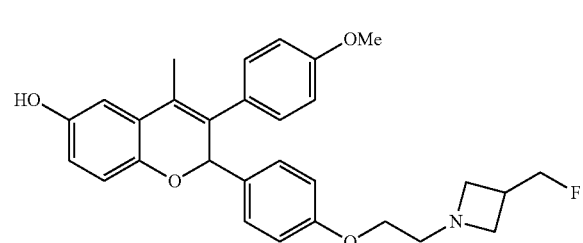
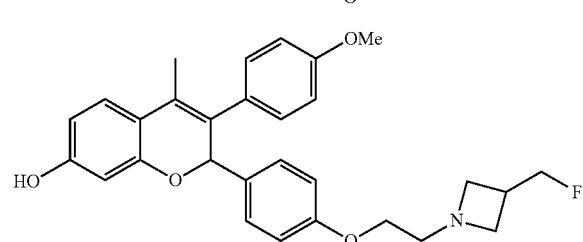
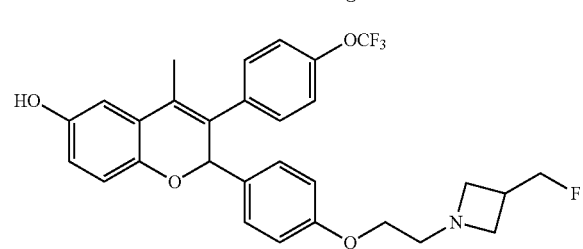
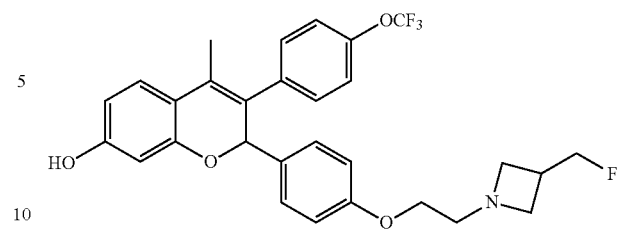
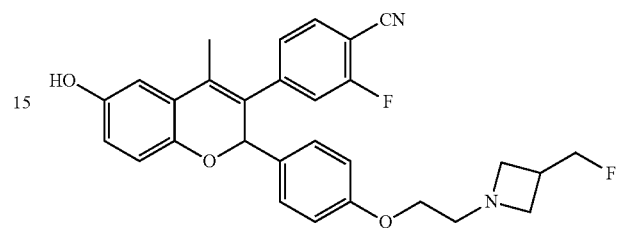
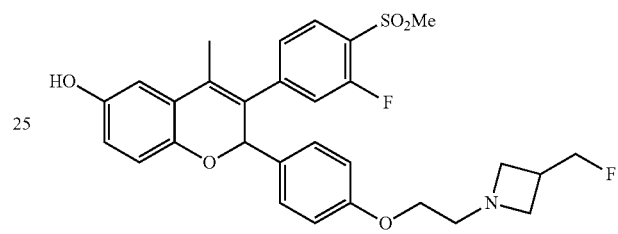
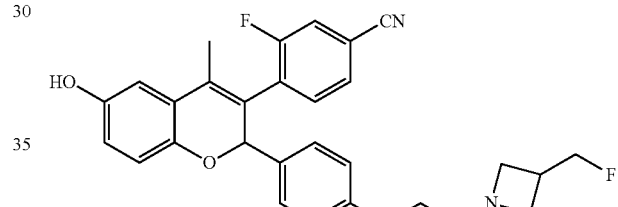
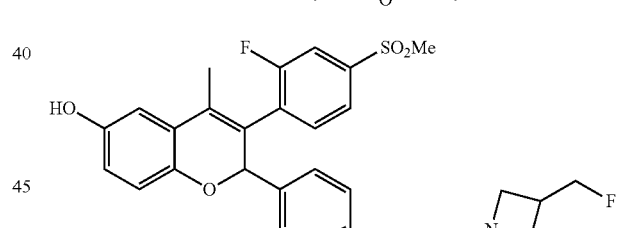
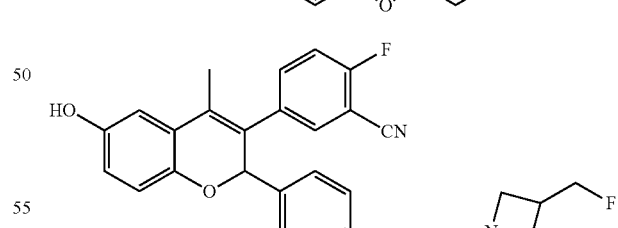
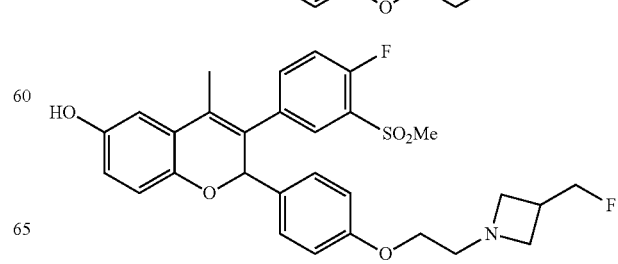

-continued
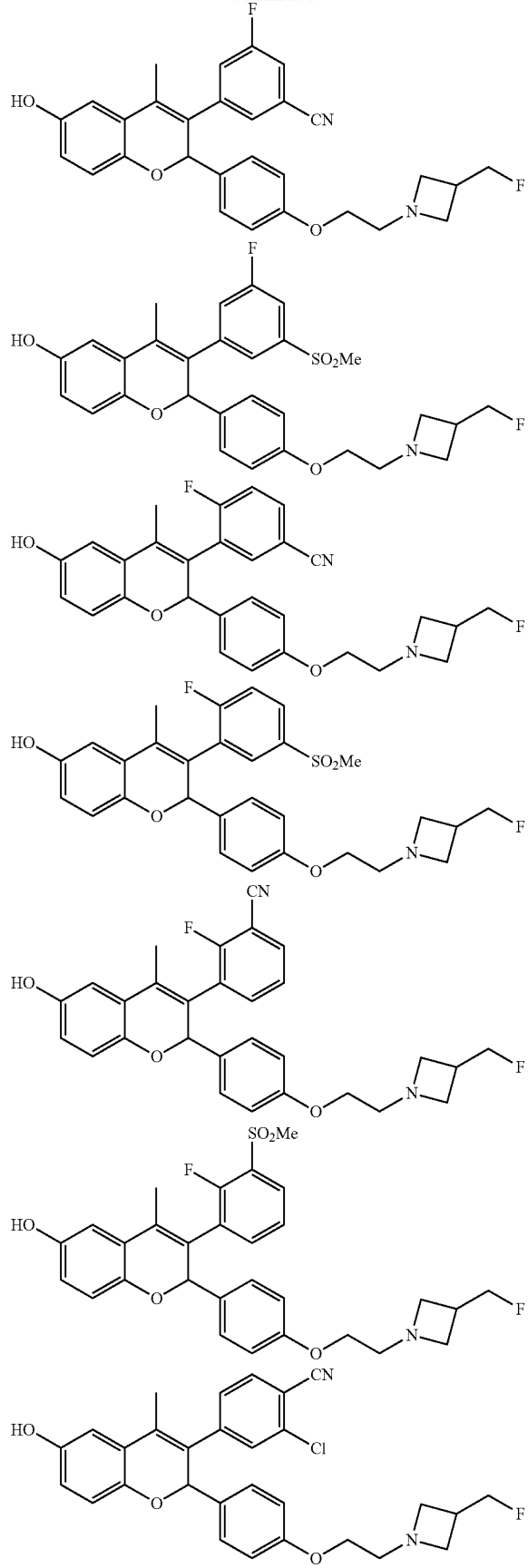
-continued
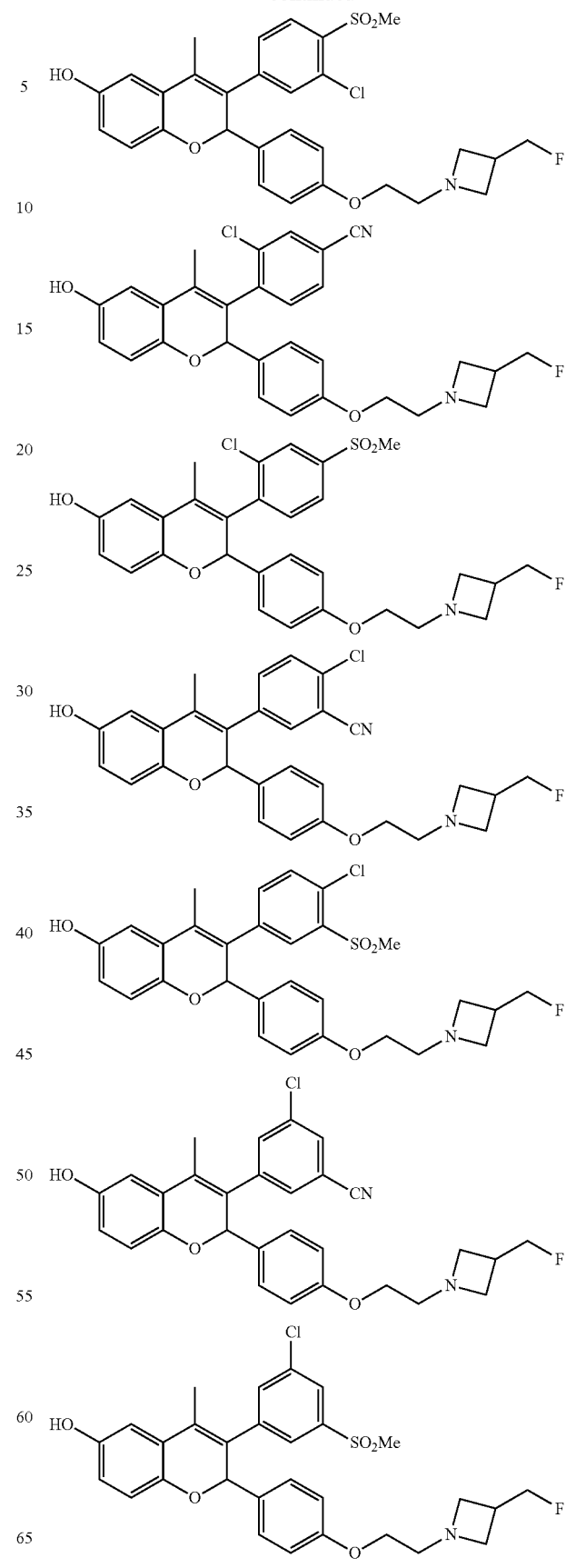

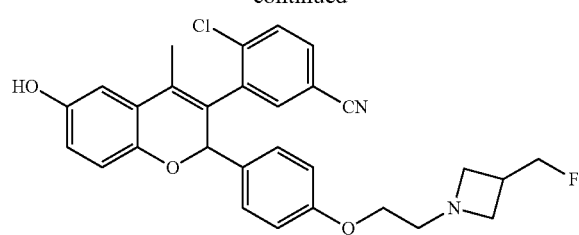
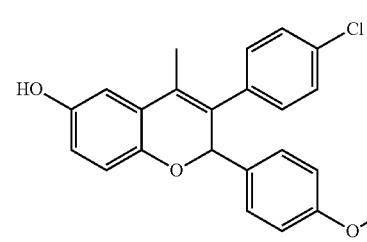
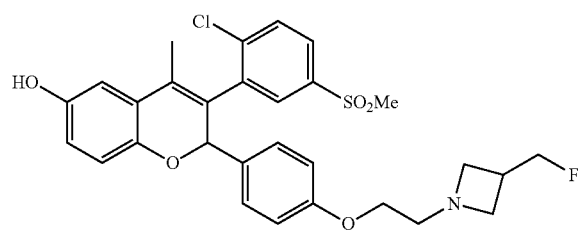
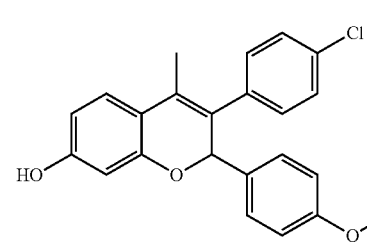
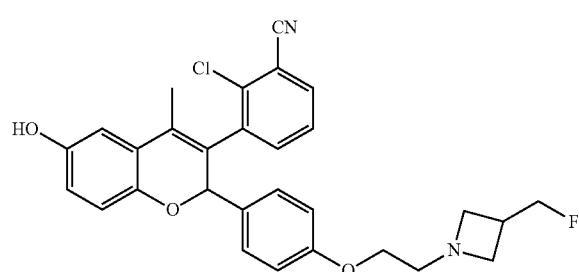
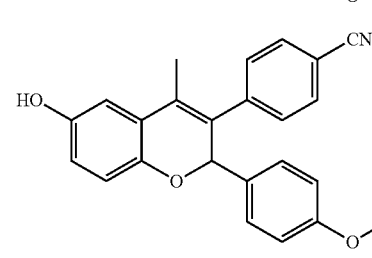
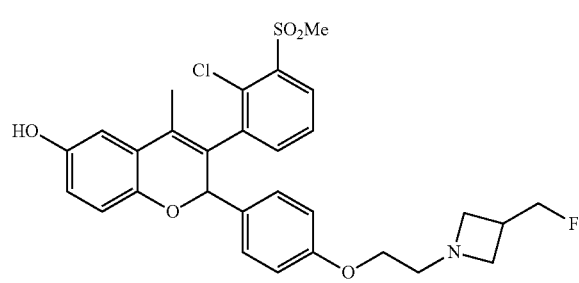
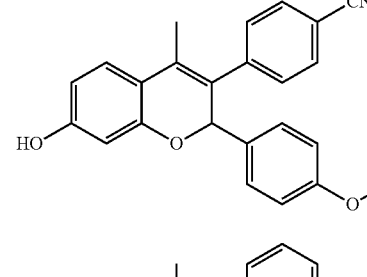
or a pharmaceutically acceptable salt, solvate or prodrug thereof.
In some embodiments, the compound of Formula (I) has one of the following structures:
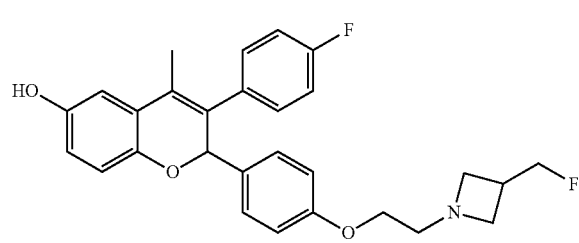
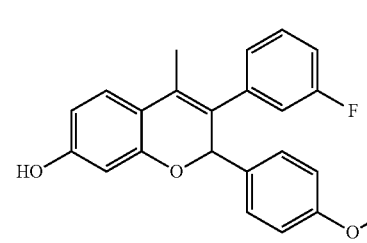
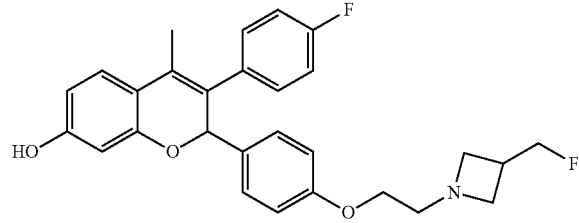
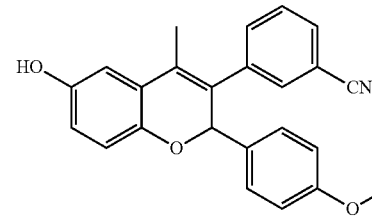

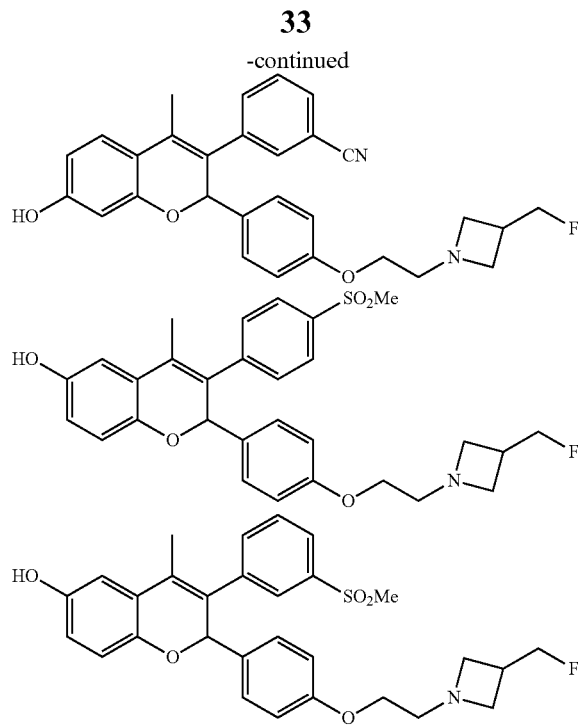

or a pharmaceutically acceptable salt, solvate or prodrug thereof.

In some embodiments, the compound of Formula (I) has the following structure:

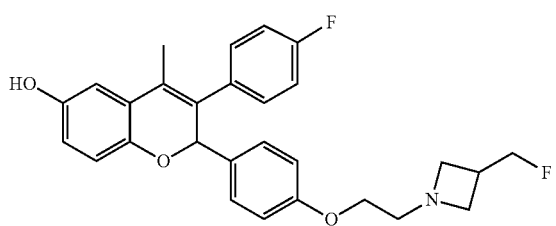 [SMILES: CC1=C(c2ccc(F)cc2)C(c2ccc(OCCN3CC(CF)C3)cc2)Oc2ccc(O)cc21]

or a pharmaceutically acceptable salt, solvate or prodrug thereof.

In some embodiments, the compound of Formula (I) has the following structure:

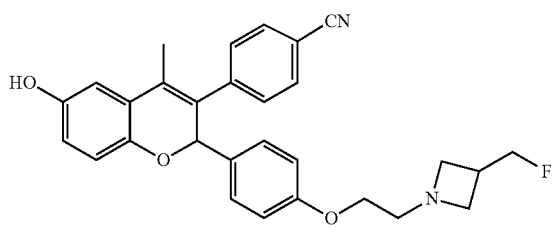 [SMILES: CC1=C(c2ccc(Cl)cc2)C(c2ccc(OCCN3CC(CF)C3)cc2)Oc2ccc(O)cc21]

or a pharmaceutically acceptable salt, solvate or prodrug thereof.

In some embodiments, the compound of Formula (I) has the following structure:

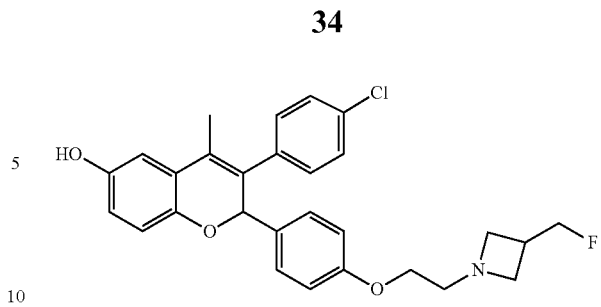

or a pharmaceutically acceptable salt, solvate or prodrug thereof.

Reference to a use of a compound of Formula (I), or a pharmaceutically acceptable salt, solvate or prodrug thereof, or a composition that includes a compound of Formula (I), or a pharmaceutically acceptable salt, solvate or prodrug thereof, refers to a racemic mixture of the compound, or a pharmaceutically acceptable salt, solvate or prodrug thereof.

In another aspect, described herein is the (R)-enantiomer of the compound of Formula (I), wherein the (R)-enantiomer of the compound of Formula (I) has the structure of Formula (II):

Formula (II)

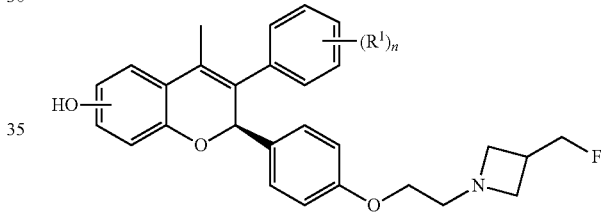

wherein, each $R^1$ is independently selected from the group consisting of halogen, —CN, —SO$_2$R$^2$, —OR$^2$, C$_1$-C$_4$alkyl, and C$_1$-C$_4$fluoroalkyl;

each $R^2$ is independently selected from the group consisting of C$_1$-C$_4$alkyl, and C$_1$-C$_4$fluoroalkyl;

n is 0, 1, 2, or 3;

or a pharmaceutically acceptable salt, solvate or prodrug thereof.

In some embodiments, each $R^1$ is independently selected from the group consisting of F, Cl, —CN, —SO$_2$R$^2$, —OR$^2$, —CH$_3$, —CH$_2$CH$_3$, —CF$_3$, and —CH$_2$CF$_3$; each $R^2$ is independently selected from the group consisting of —CH$_3$, —CH$_2$CH$_3$, —CF$_3$, and —CH$_2$CF$_3$.

In some embodiments, each $R^1$ is independently selected from the group consisting of F, Cl, —CN, —CH$_3$, and —CF$_3$. In some embodiments, each $R^1$ is independently selected from the group consisting of F, Cl, —CN, —SO$_2$CH$_3$, —OCF$_3$ and —CF$_3$. In some embodiments, each $R^1$ is independently selected from the group consisting of F, —CN, and —SO$_2$CH$_3$.

In some embodiments, the compound of Formula (II) has the following structure:

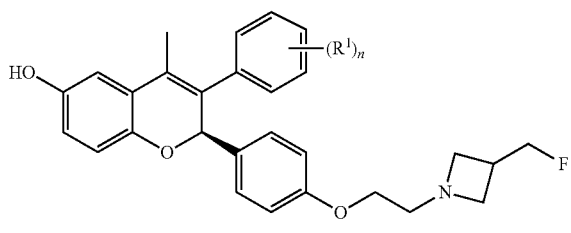

or a pharmaceutically acceptable salt, solvate or prodrug thereof.

In some embodiments, the compound of Formula (II) has the following structure:

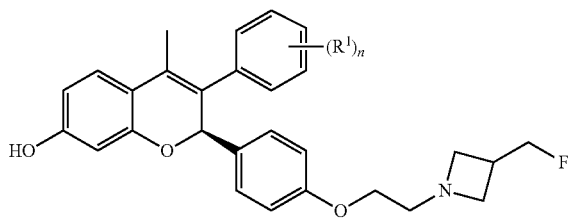

or a pharmaceutically acceptable salt, solvate or prodrug thereof.

In some embodiments, n is 1.

In some embodiments, the compound of Formula (II) has the following structure:

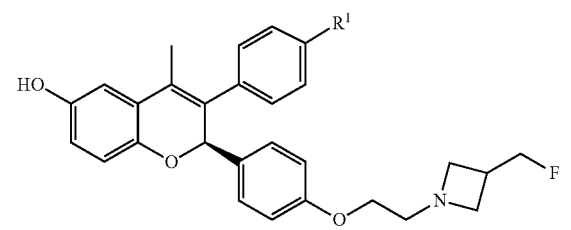

or a pharmaceutically acceptable salt, solvate or prodrug thereof.

In some embodiments, $R^1$ is F. In some embodiments, $R^1$ is CN.

In some embodiments, n is 2.

In some embodiments, the compound of Formula (II) has the following structure:

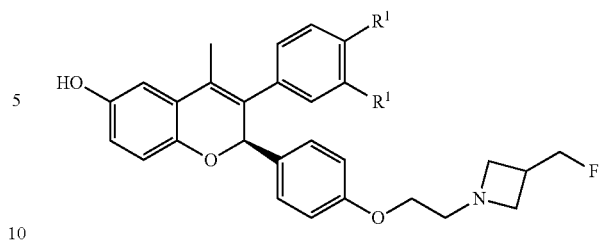

or a pharmaceutically acceptable salt, solvate or prodrug thereof.

In some embodiments, the compound of Formula (II) has the following structure:

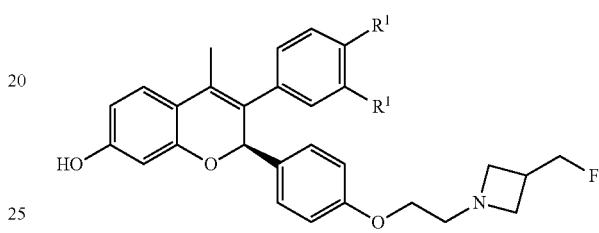

or a pharmaceutically acceptable salt, solvate or prodrug thereof.

In some embodiments, n is 3.

In some embodiments, the compound of Formula (II) has the following structure:

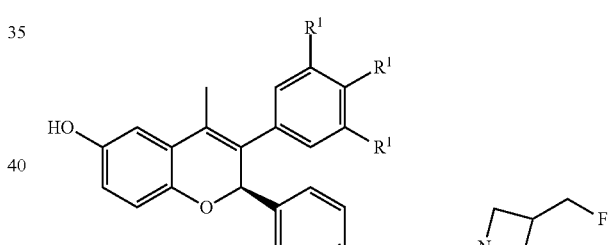

or a pharmaceutically acceptable salt, solvate or prodrug thereof.

In some embodiments, the compound of Formula (II) has the following structure:

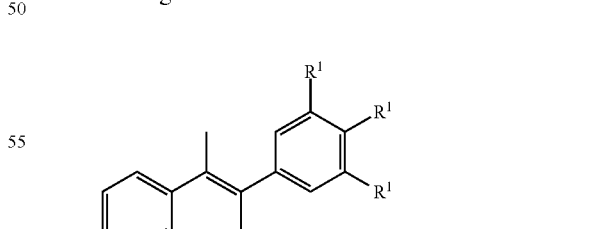

or a pharmaceutically acceptable salt, solvate or prodrug thereof.

In some embodiments, the compound of Formula (II) has one of the following structures:

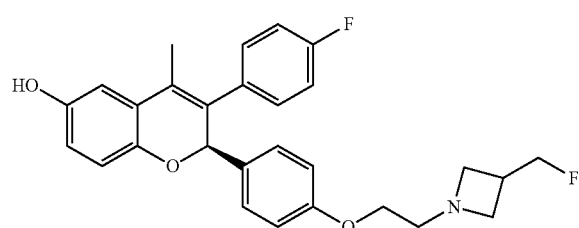
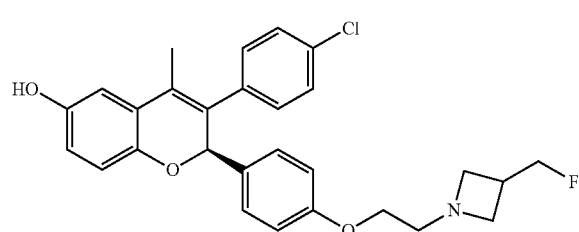
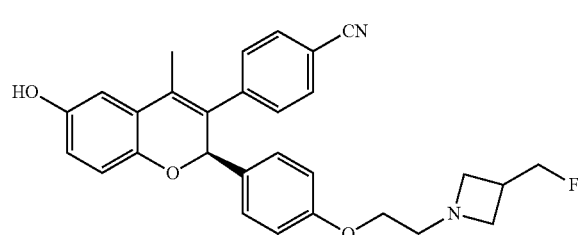
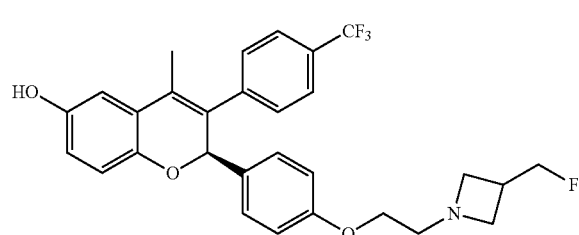
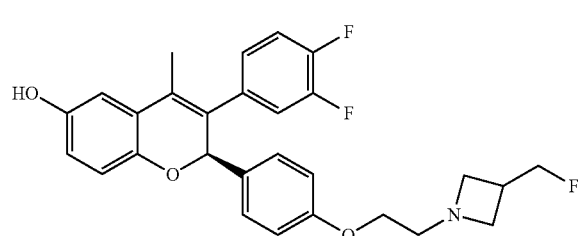
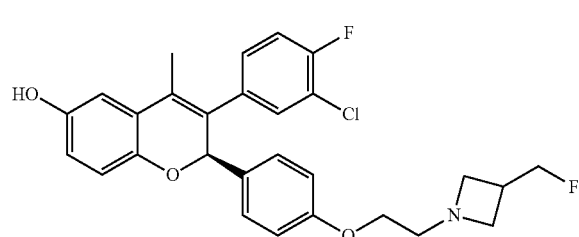
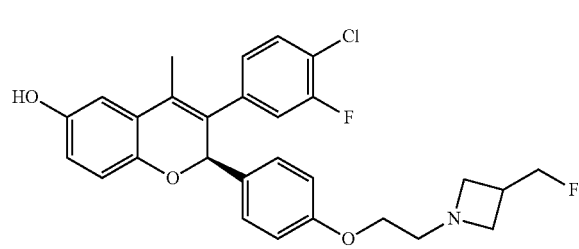
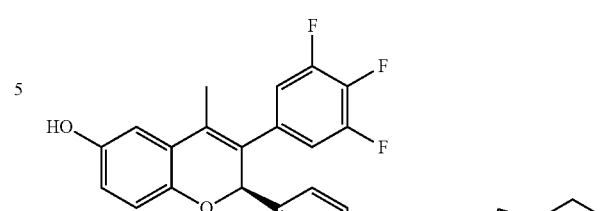
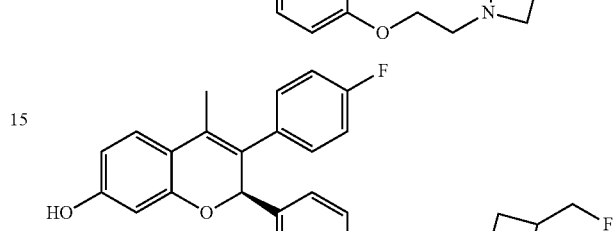
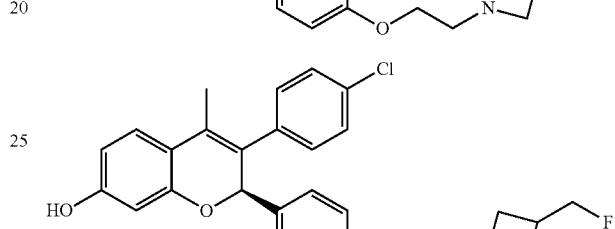
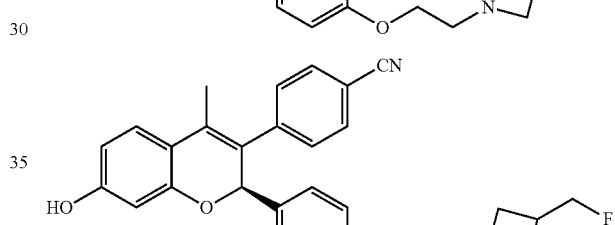
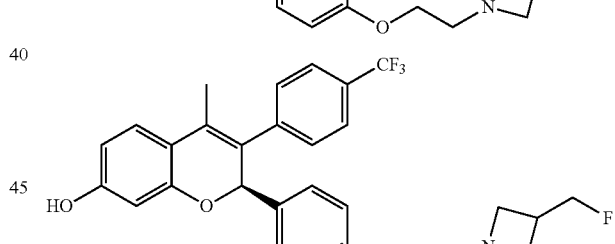
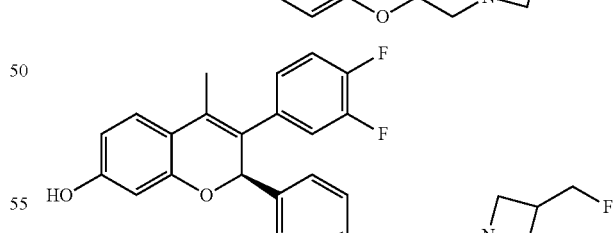
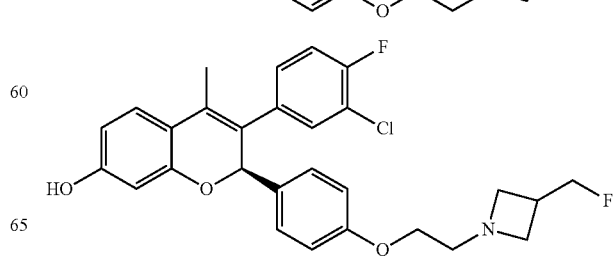

39
-continued
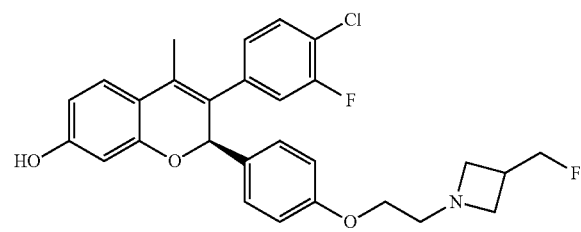
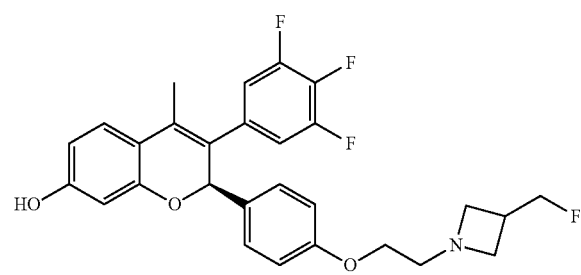
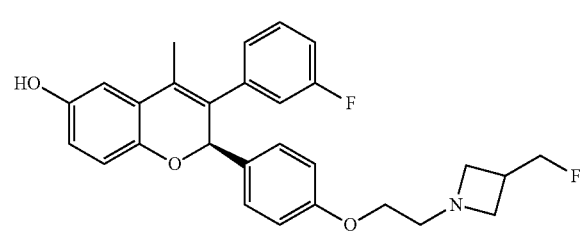
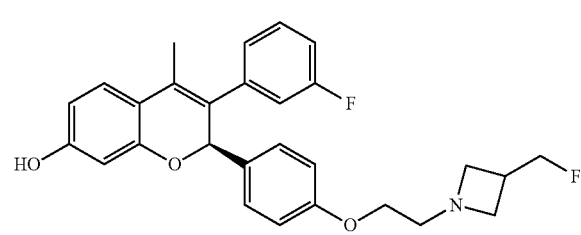
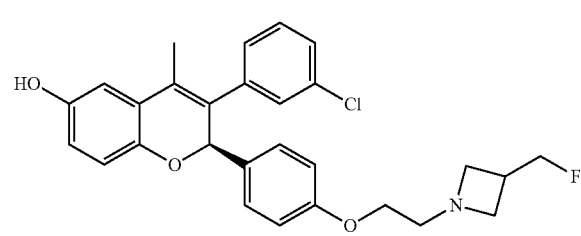
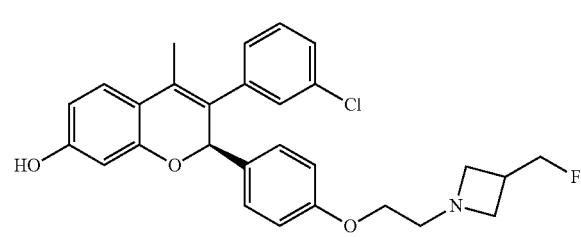
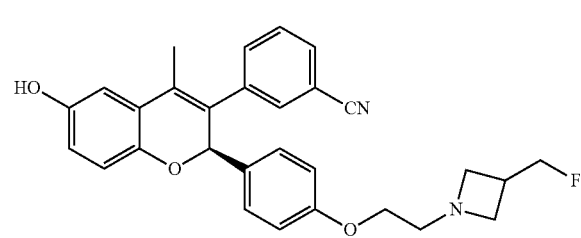
40
-continued
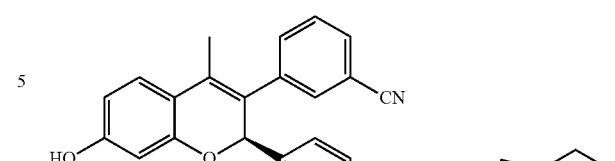
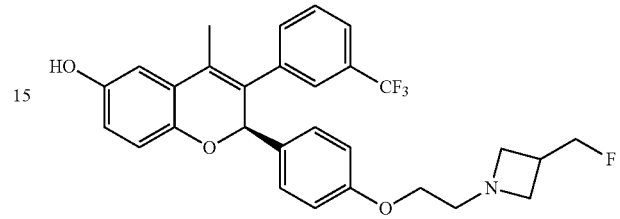
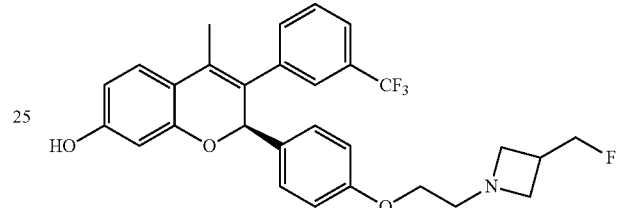
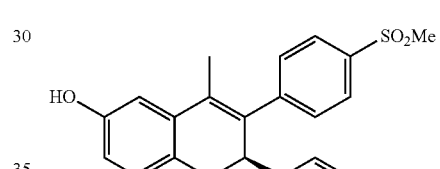
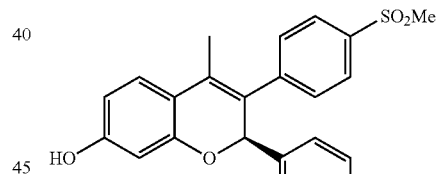
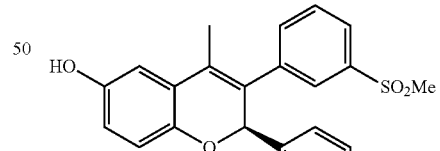
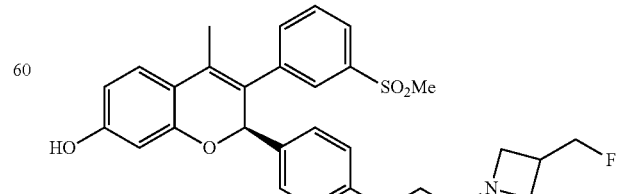

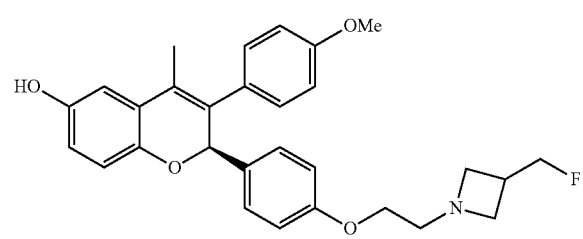
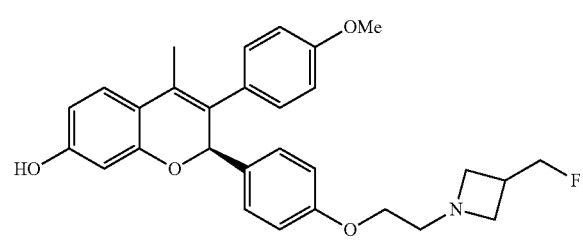
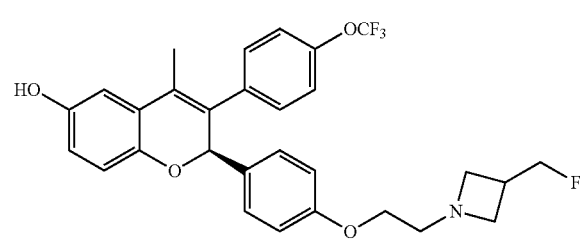
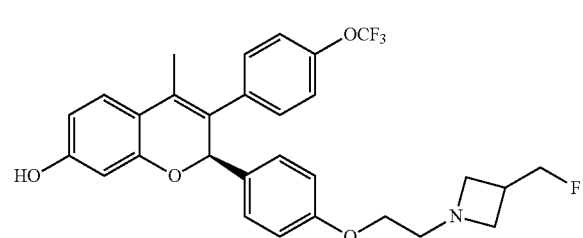
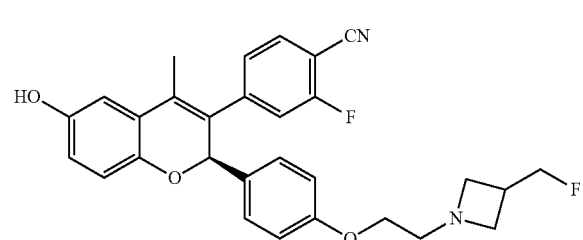
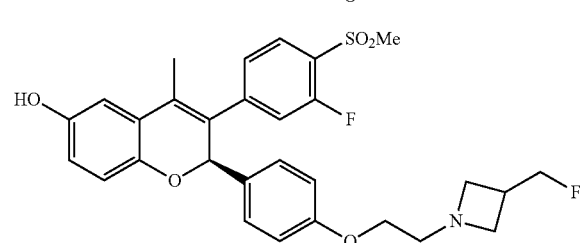
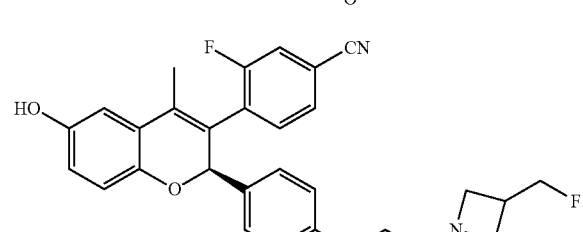
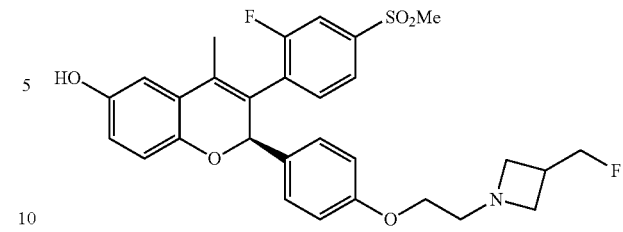
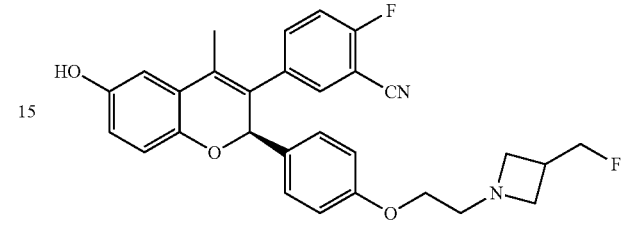
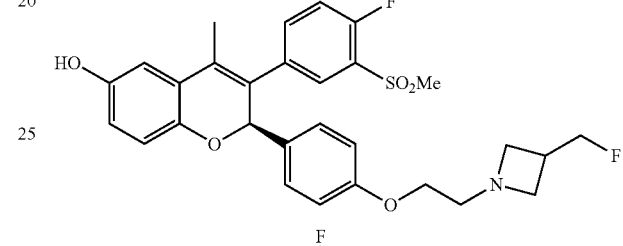
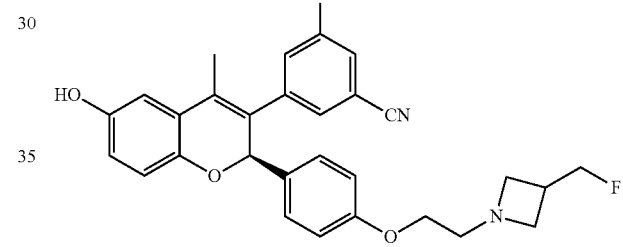
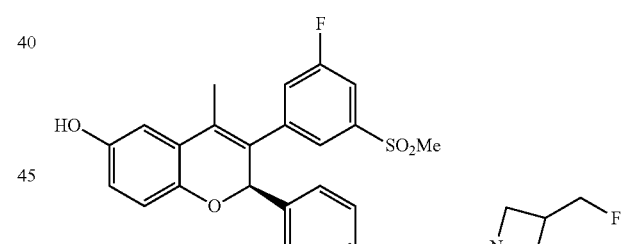
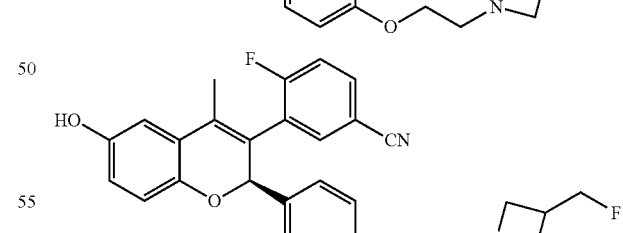
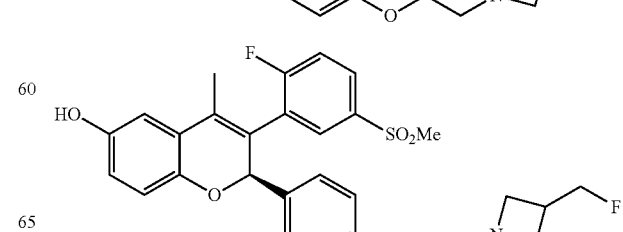

-continued
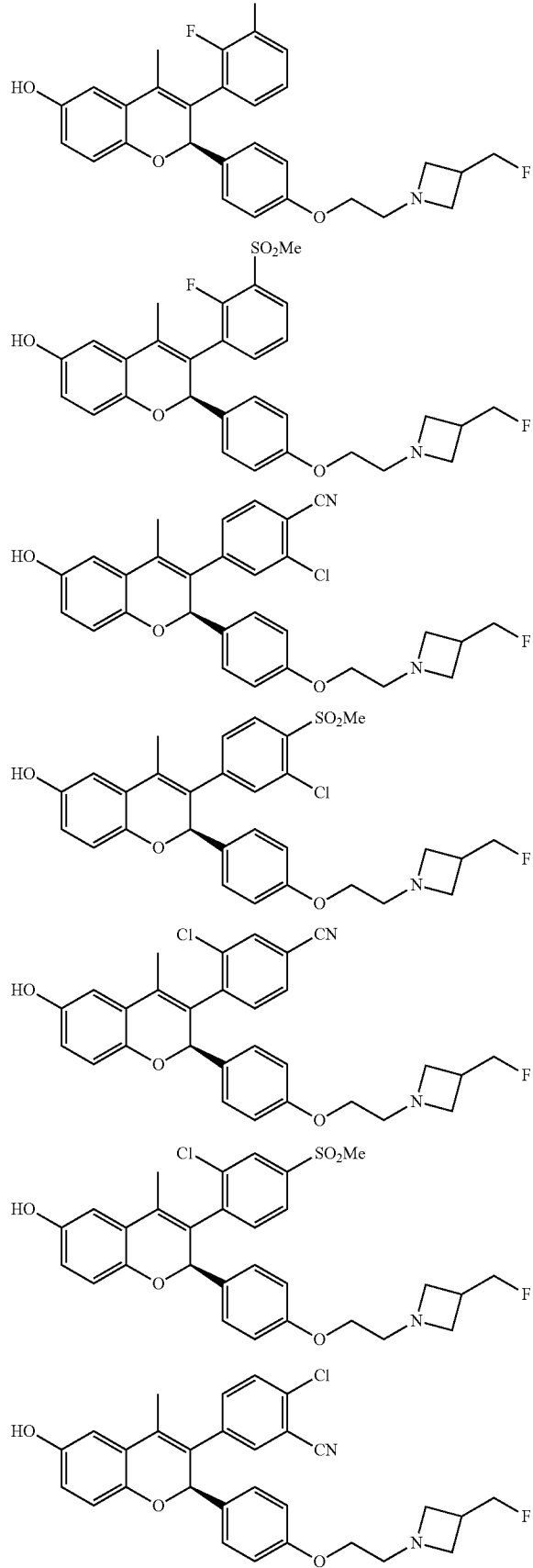
-continued
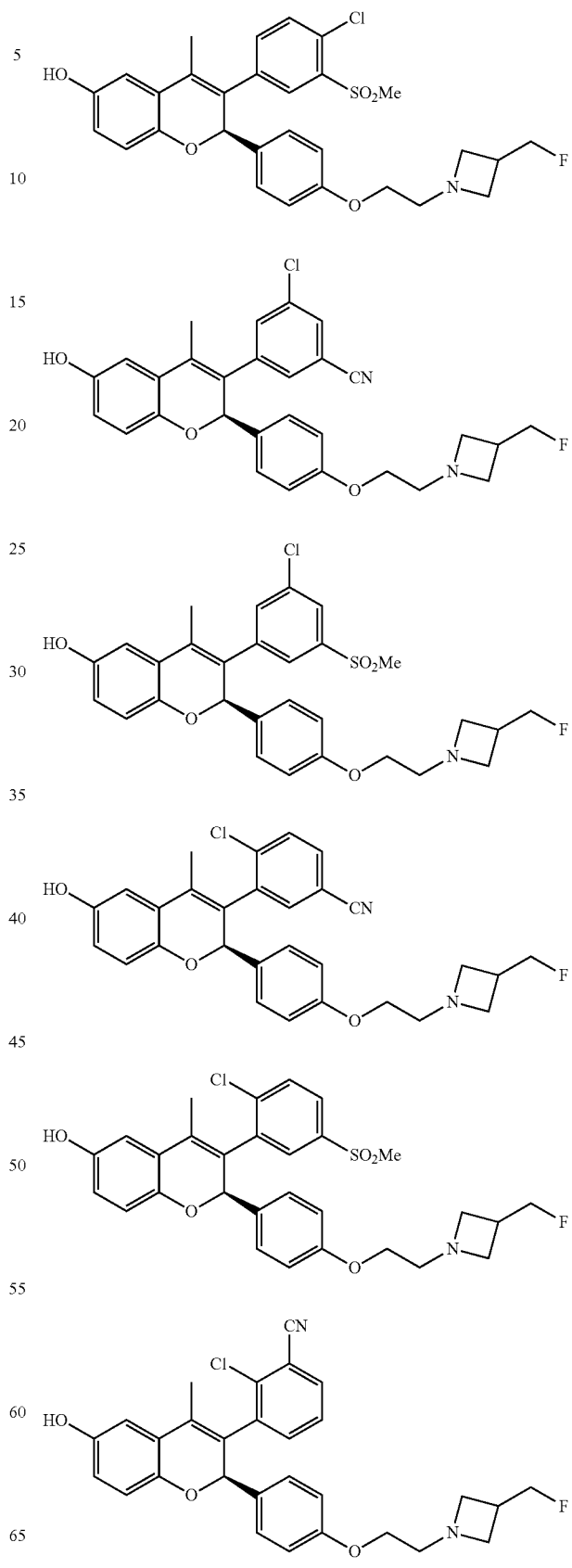

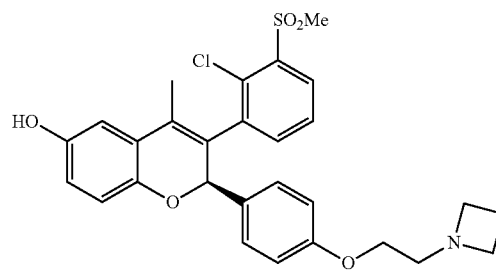
or a pharmaceutically acceptable salt, solvate or prodrug thereof.
In some embodiments, the compound of Formula (II) has one of the following structures:
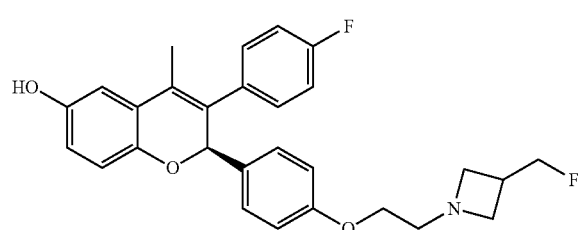
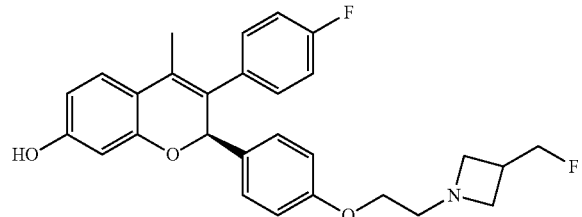
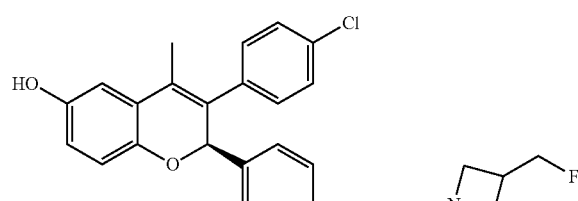
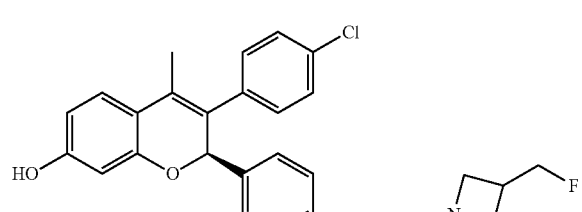
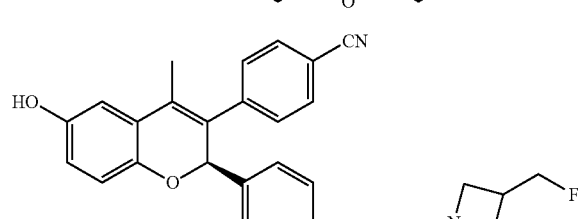
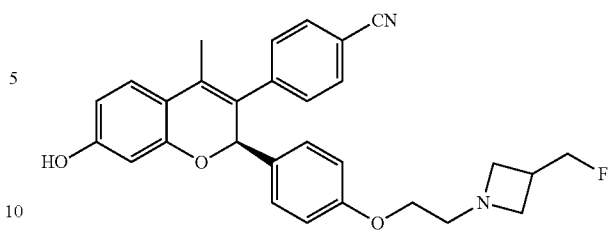
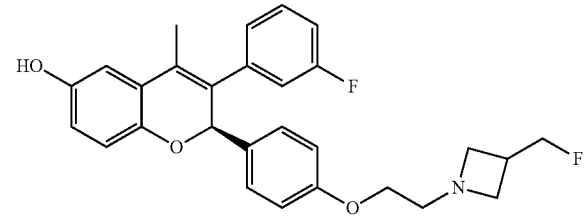
or a pharmaceutically acceptable salt, solvate or prodrug thereof.

In some embodiments, the compound of Formula (II) has the following structure:

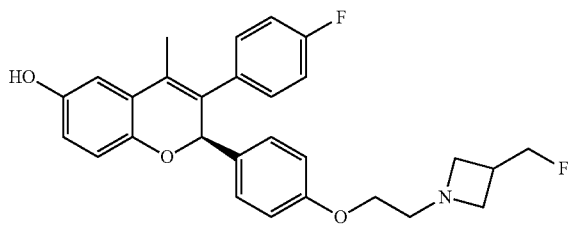

or a pharmaceutically acceptable salt, solvate or prodrug thereof.

In some embodiments, the compound of Formula (II) has the following structure:

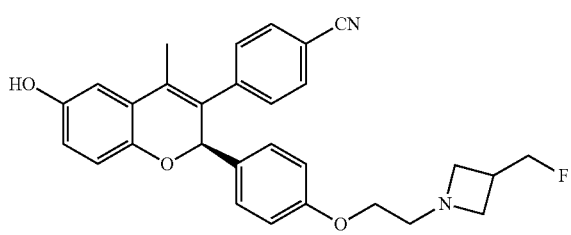 [SMILES: CC1=C(c2ccc(C#N)cc2)[C@@H](c2ccc(OCCN3CC(CF)C3)cc2)Oc2ccc(O)cc21]

or a pharmaceutically acceptable salt, solvate or prodrug thereof.

In some embodiments, the compound of Formula (II) has the following structure:

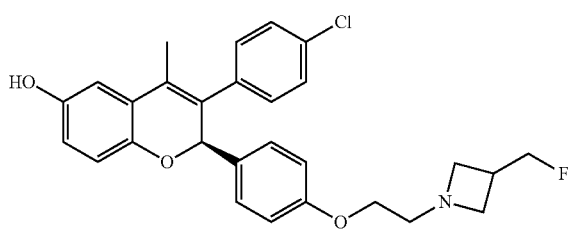

or a pharmaceutically acceptable salt, solvate or prodrug thereof.

Reference to a use of a compound of Formula (II), or a pharmaceutically acceptable salt, solvate or prodrug thereof, or a composition that includes a compound of Formula (II), or a pharmaceutically acceptable salt, solvate or prodrug thereof, refers to any optical purity of the compound of Formula (II), or a pharmaceutically acceptable salt, solvate or prodrug thereof, in the composition, including but not limited to optically pure compound, or a pharmaceutically acceptable salt, solvate or prodrug thereof.

In some embodiments, the enantiomeric ratio of the compound of Formula (II), or a pharmaceutically acceptable salt, solvate or prodrug thereof, is greater than 90:10. In some embodiments, the enantiomeric ratio of the compound of Formula (II), or a pharmaceutically acceptable salt, solvate or prodrug thereof, is greater than 95:5. In some embodiments, the enantiomeric ratio of the compound of Formula (II), or a pharmaceutically acceptable salt, solvate or prodrug thereof, is greater than 99:1. In some embodiments, the compound of Formula (II), or a pharmaceutically acceptable salt, solvate or prodrug thereof, is optically pure.

In yet another aspect, described herein is the (S)-enantiomer of the compound of Formula (I), wherein the (S)-enantiomer of the compound of Formula (I) has the structure of Formula (III):

Formula (III)

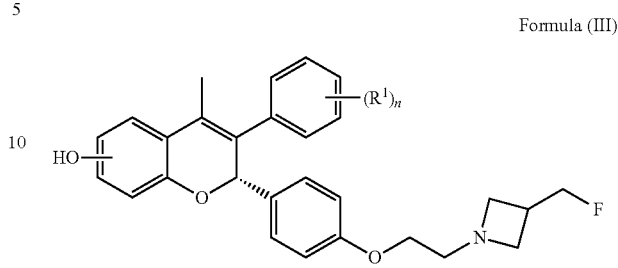

wherein,
each $R^1$ is independently selected from the group consisting of halogen, —CN, —SO$_2$R$^2$, —OR$^2$, C$_1$-C$_4$alkyl, and C$_1$-C$_4$fluoroalkyl;
each $R^2$ is independently selected from the group consisting of C$_1$-C$_4$alkyl, and C$_1$-C$_4$fluoroalkyl;
n is 0, 1, 2, or 3;
or a pharmaceutically acceptable salt, solvate or prodrug thereof.

In some embodiments, each $R^1$ is independently selected from the group consisting of F, Cl, —CN, —SO$_2$R$^2$, —OR$^2$, —CH$_3$, —CH$_2$CH$_3$, —CF$_3$, and —CH$_2$CF$_3$; each $R^2$ is independently selected from the group consisting of —CH$_3$, —CH$_2$CH$_3$, —CF$_3$, and —CH$_2$CF$_3$. In some embodiments, each $R^1$ is independently selected from the group consisting of F, Cl, —CN, —SO$_2$CH$_3$, —OCF$_3$ and —CF$_3$. In some embodiments, each $R^1$ is independently selected from the group consisting of F, —CN, and —SO$_2$CH$_3$.

In some embodiments, each $R^1$ is independently selected from the group consisting of F, Cl, —CN, —CH$_3$, and —CF$_3$.

In some embodiments, the compound of Formula (III) has the following structure:

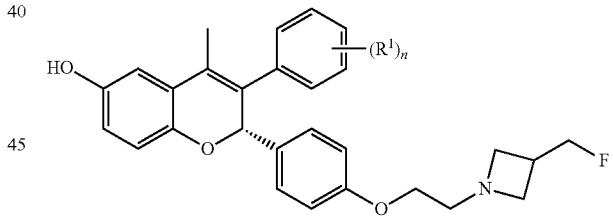

or a pharmaceutically acceptable salt, solvate or prodrug thereof.

In some embodiments, the compound of Formula (III) has the following structure:

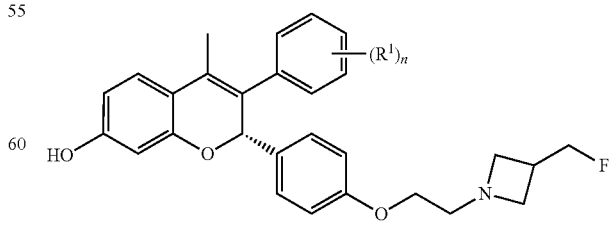

or a pharmaceutically acceptable salt, solvate or prodrug thereof.

In some embodiments, n is 1.

In some embodiments, the compound of Formula (III) has the following structure:

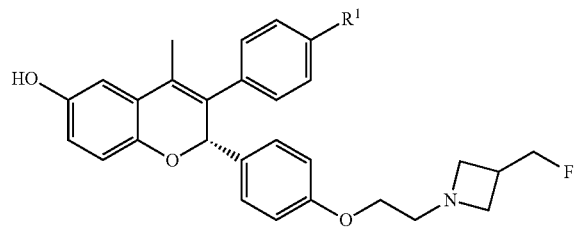

or a pharmaceutically acceptable salt, solvate or prodrug thereof.

In some embodiments, the compound of Formula (III) has the following structure:

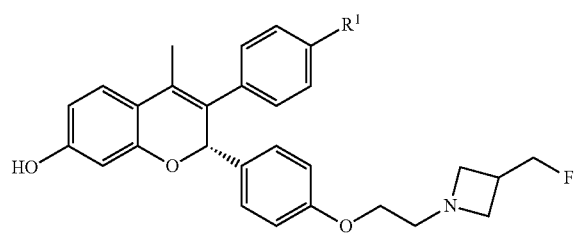

or a pharmaceutically acceptable salt, solvate or prodrug thereof.

In some embodiments, R¹ is F. In some embodiments, R¹ is CN.

In some embodiments, n is 2.

In some embodiments, the compound of Formula (III) has the following structure:

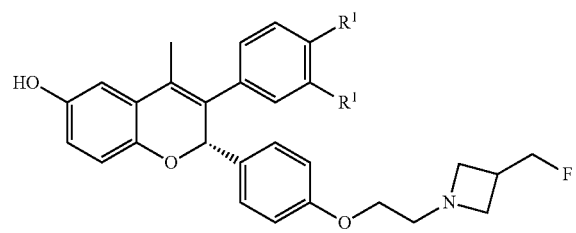

or a pharmaceutically acceptable salt, solvate or prodrug thereof.

In some embodiments, the compound of Formula (III) has the following structure:

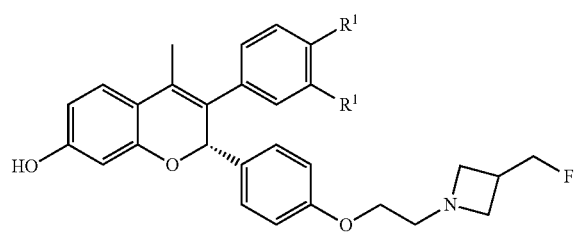

or a pharmaceutically acceptable salt, solvate or prodrug thereof.

In some embodiments, n is 3.

In some embodiments, the compound of Formula (III) has the following structure:

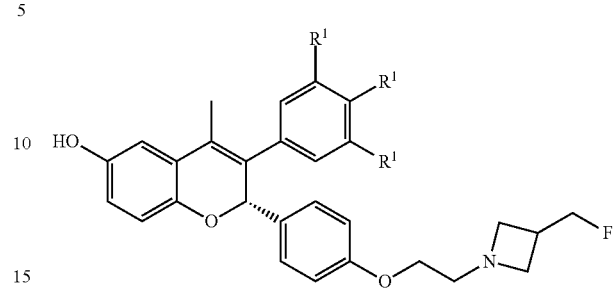

or a pharmaceutically acceptable salt, solvate or prodrug thereof.

In some embodiments, the compound of Formula (III) has the following structure:

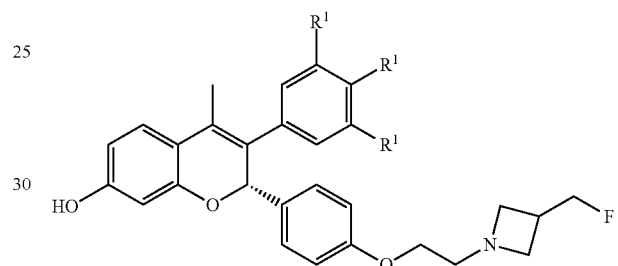

or a pharmaceutically acceptable salt, solvate or prodrug thereof.

In some embodiments, the compound of Formula (III) has one of the following structures:

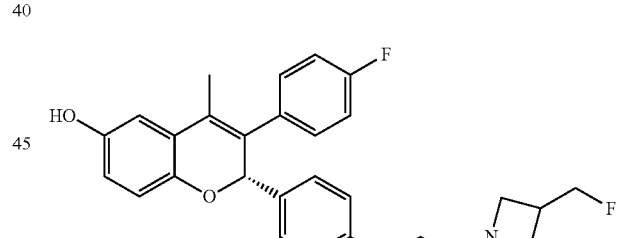

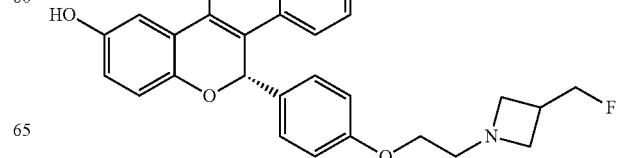

-continued
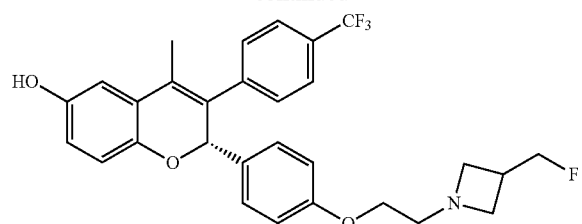
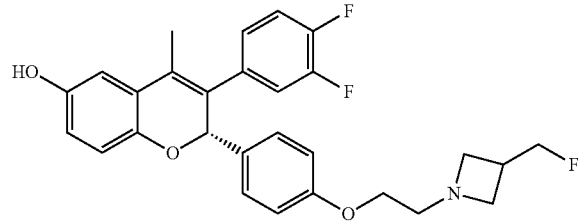
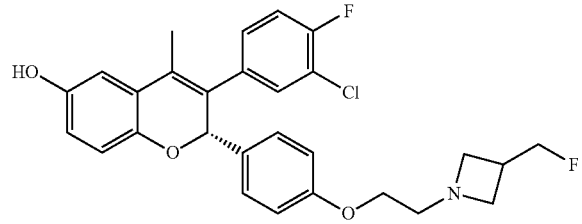
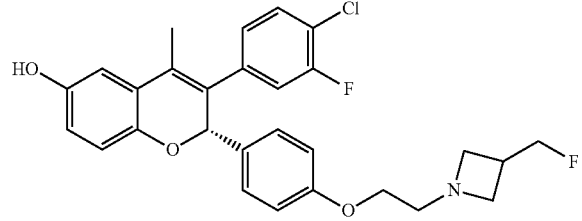
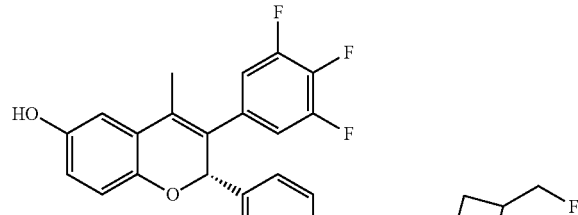
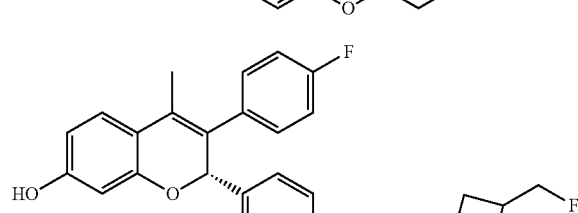
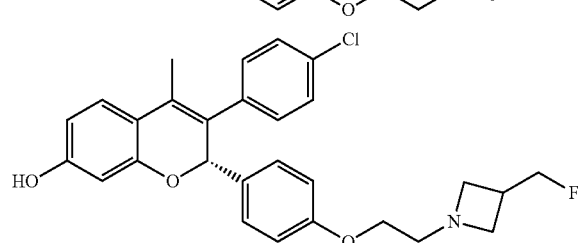
-continued
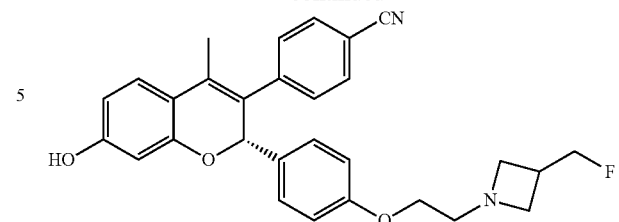
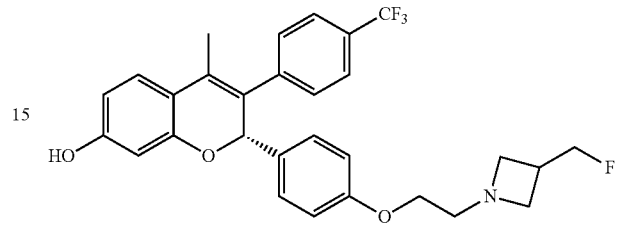
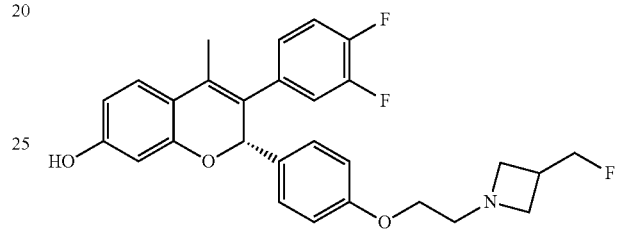
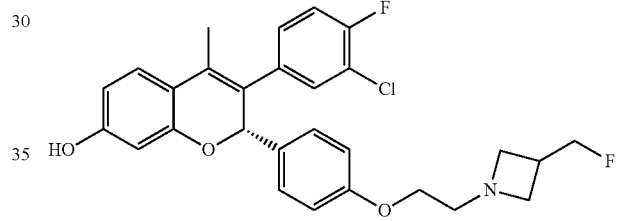
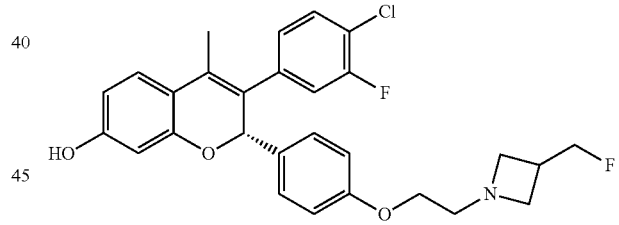
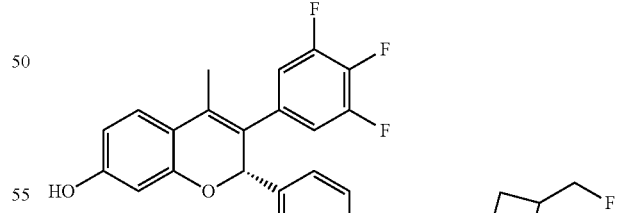
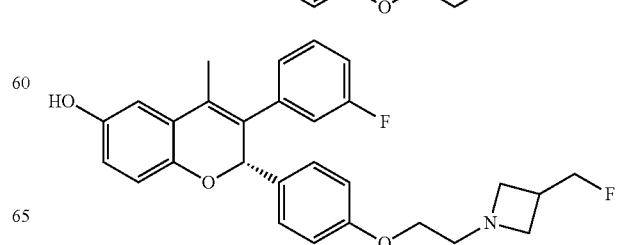

53
-continued
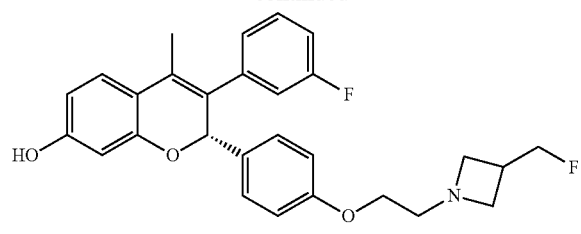
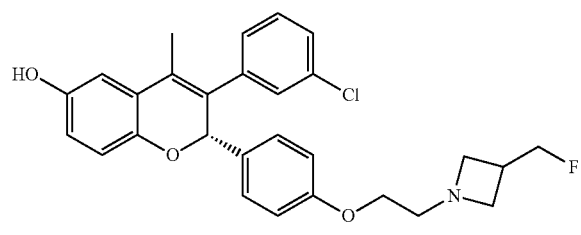
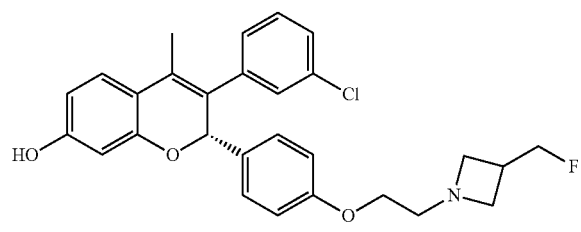
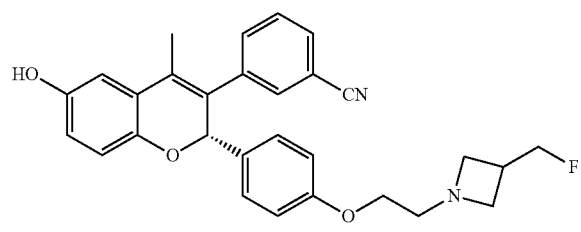
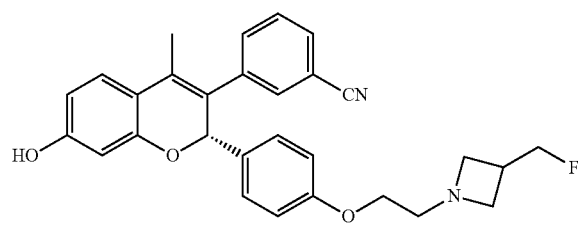
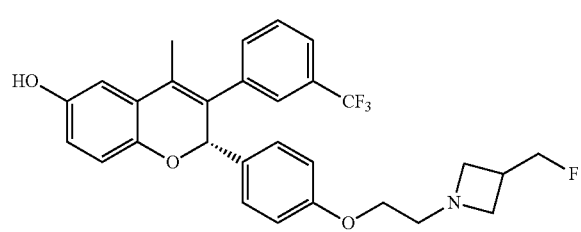
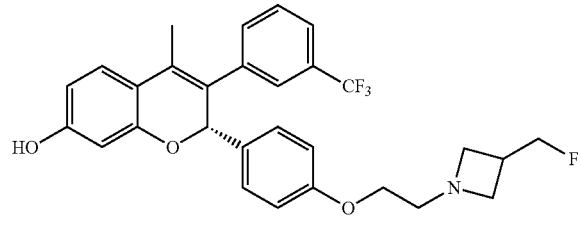
54
-continued
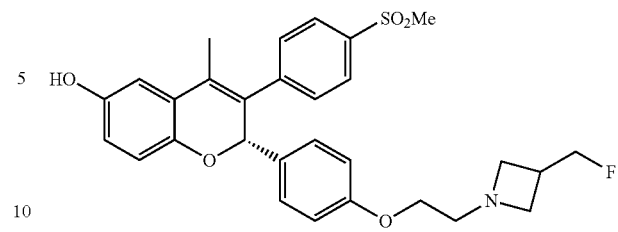
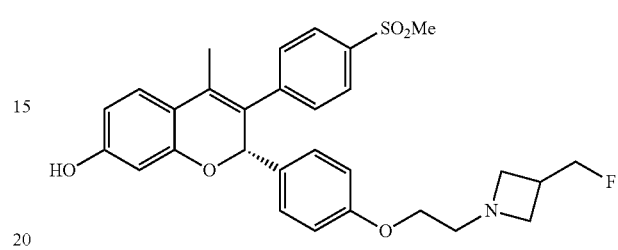
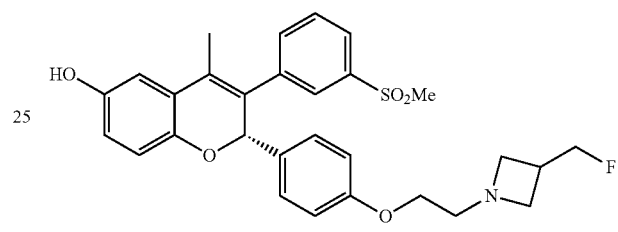
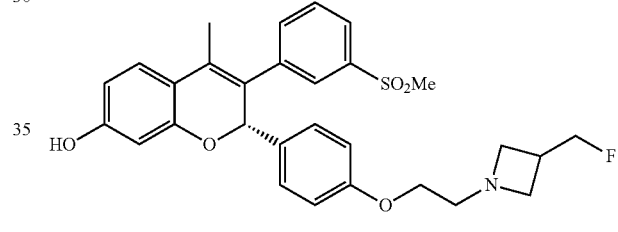
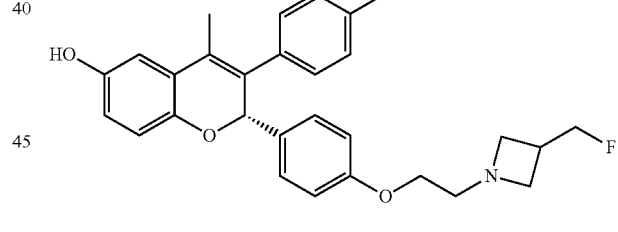
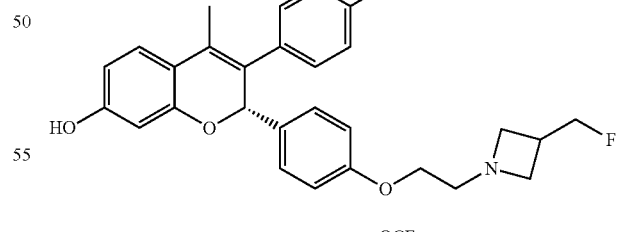
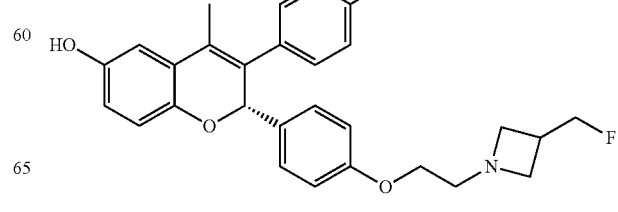

55
-continued
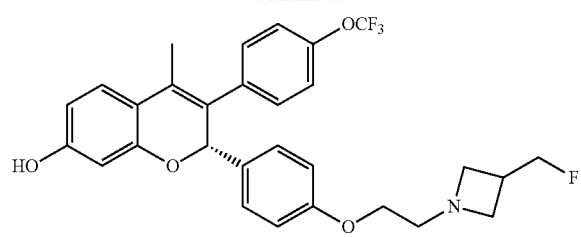
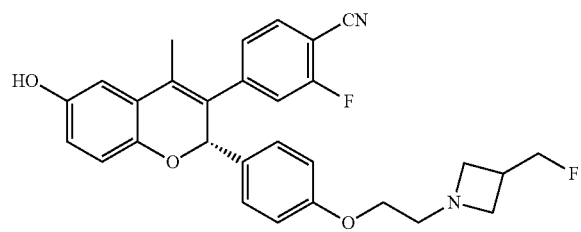
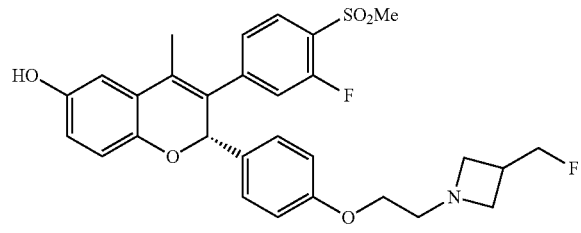
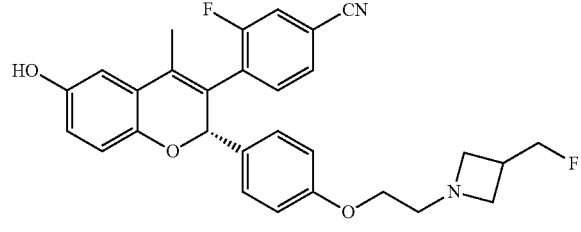
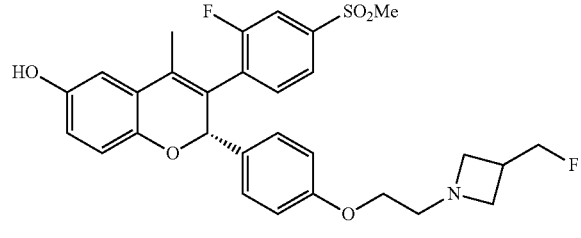
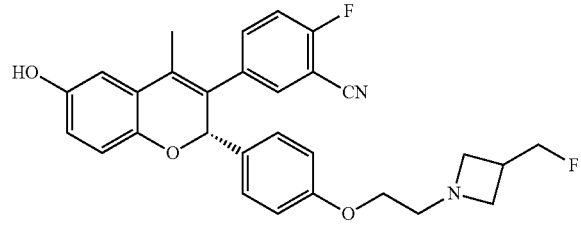
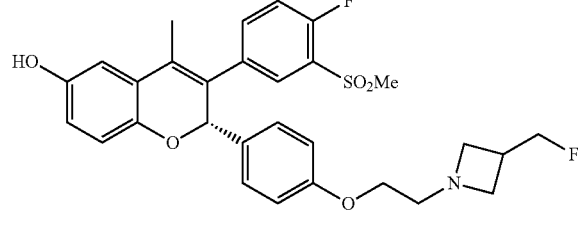
56
-continued
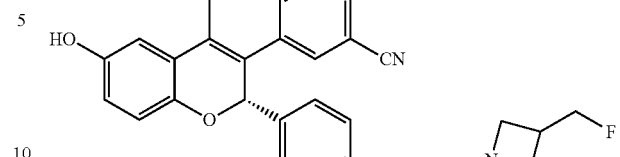
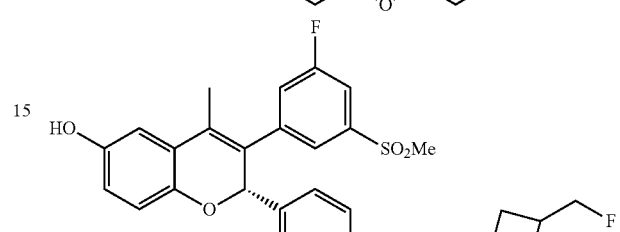
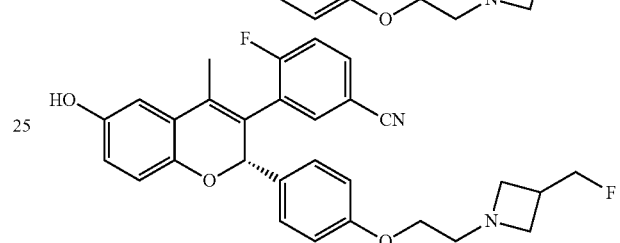
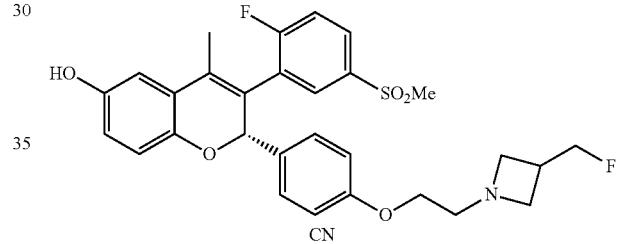
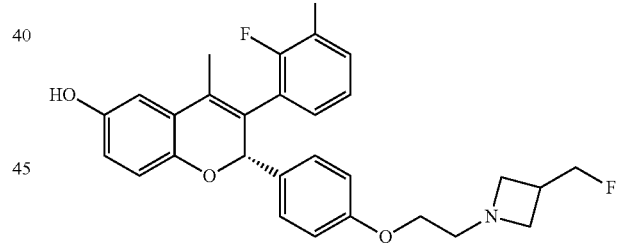
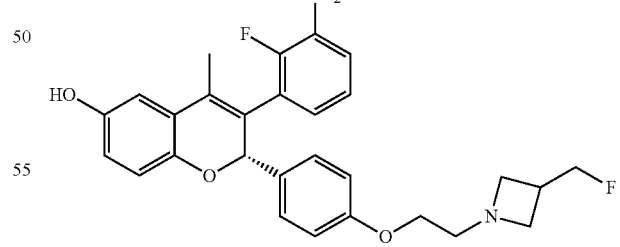
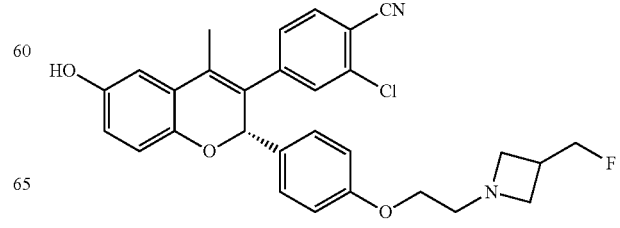

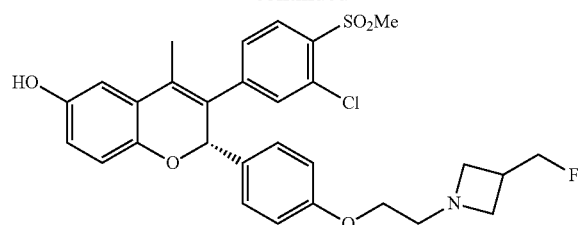
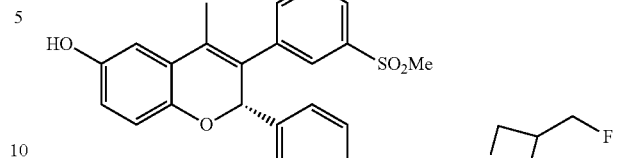
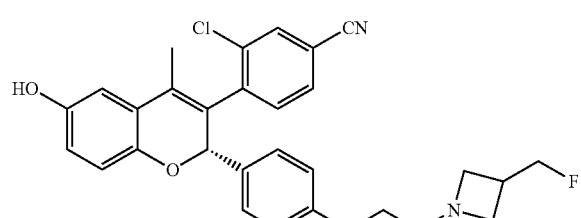
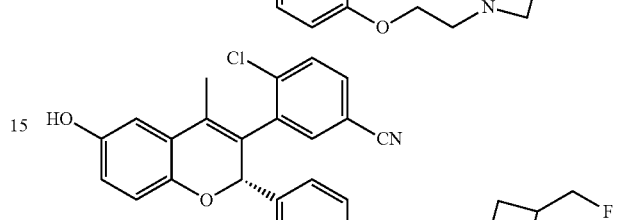
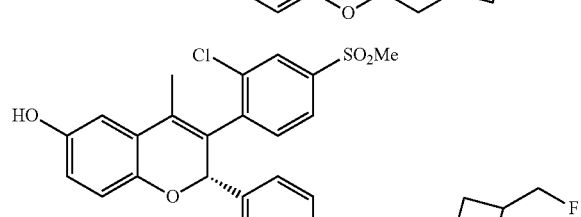
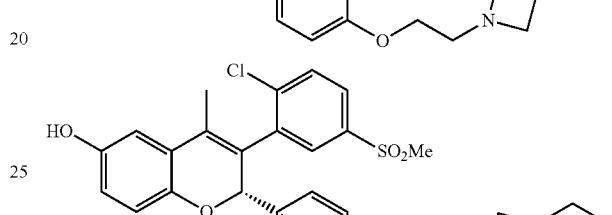
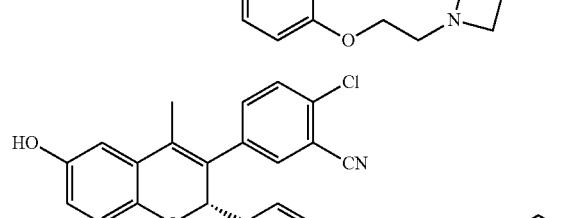
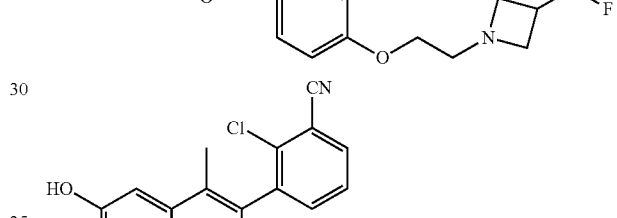
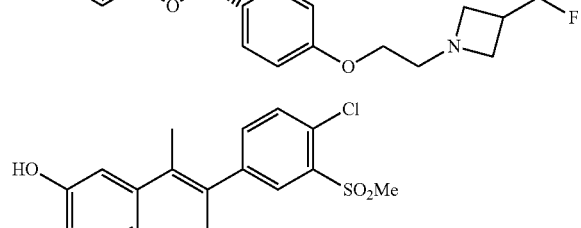
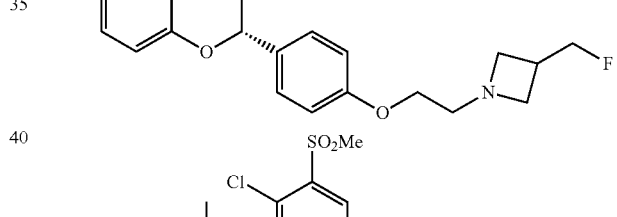
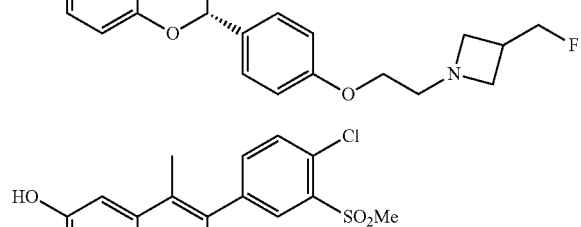
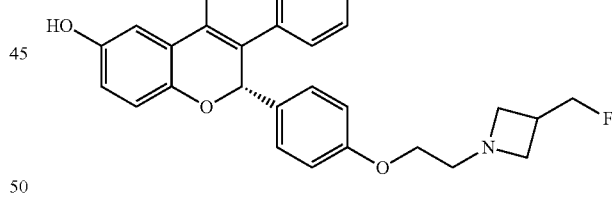
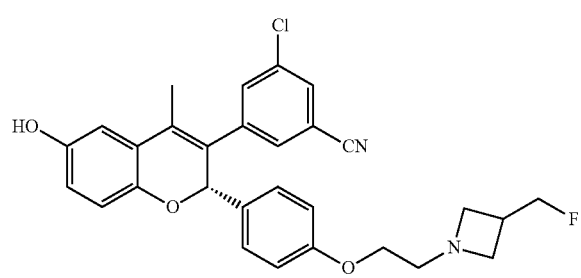
or a pharmaceutically acceptable salt, solvate or prodrug thereof.
In some embodiments, the compound of Formula (III) has one of the following structures:
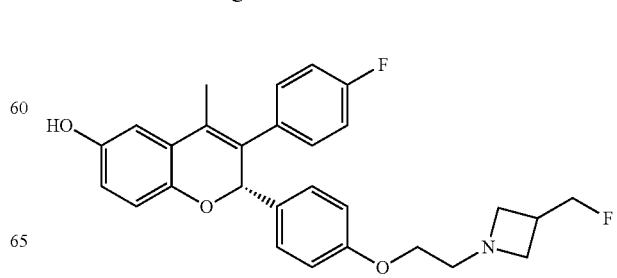

-continued

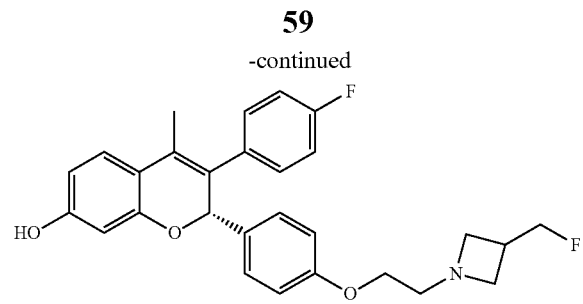

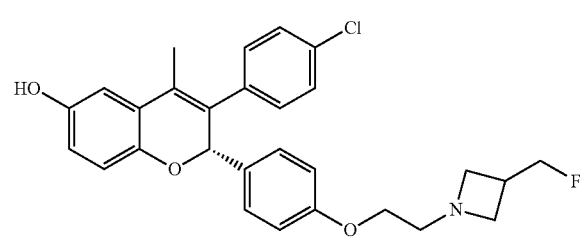

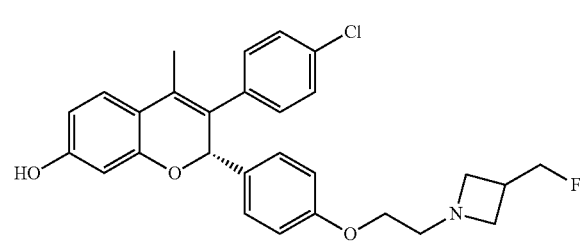

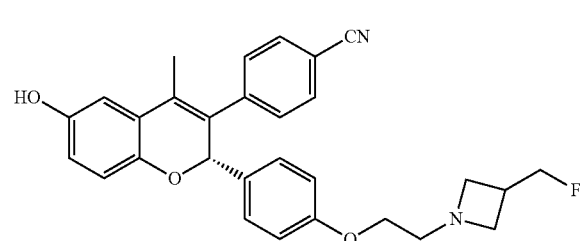

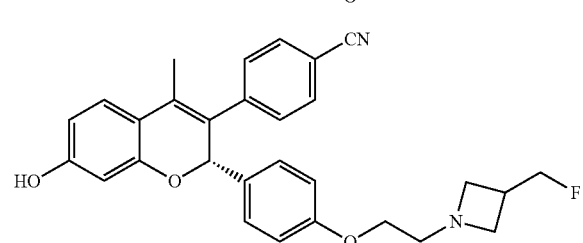

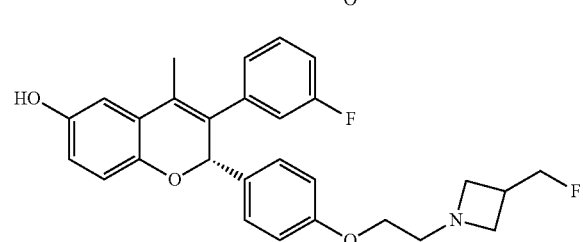

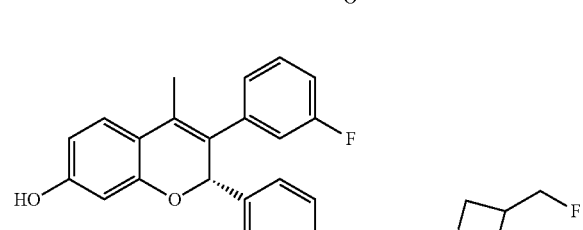

-continued

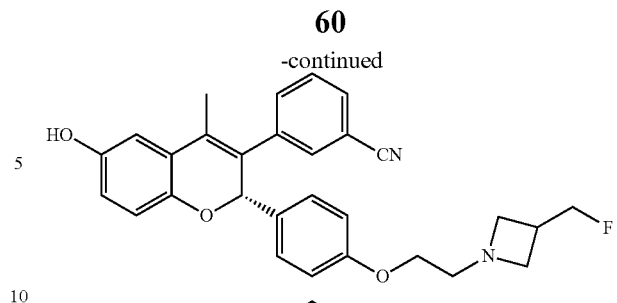

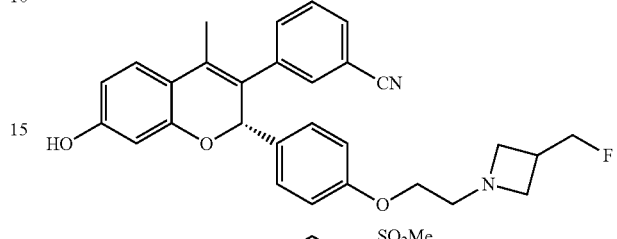

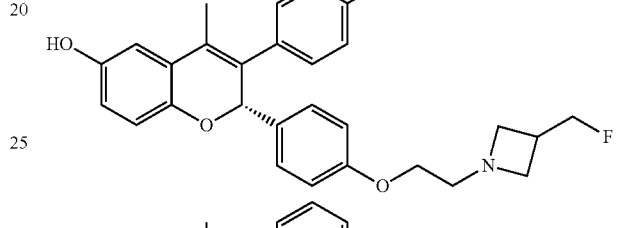

or a pharmaceutically acceptable salt, solvate or prodrug thereof.

In some embodiments, the compound of Formula (III) has the following structure:

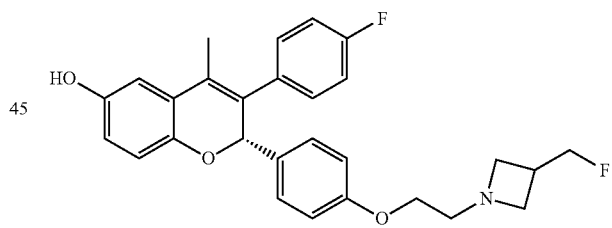

or a pharmaceutically acceptable salt, solvate or prodrug thereof.

In some embodiments, the compound of Formula (III) has the following structure:

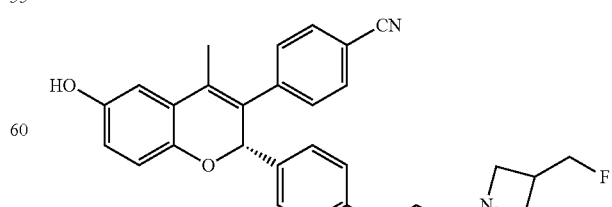

or a pharmaceutically acceptable salt, solvate or prodrug thereof.

In some embodiments, the compound of Formula (III) has the following structure:

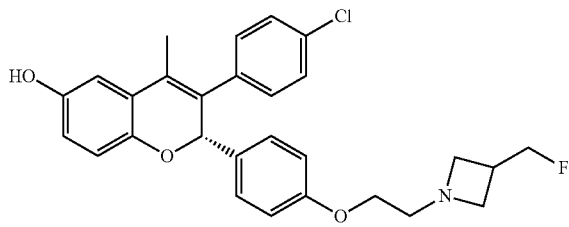

or a pharmaceutically acceptable salt, solvate or prodrug thereof.

Reference to a use of a compound of Formula (III), or a pharmaceutically acceptable salt, solvate or prodrug thereof, or a composition that includes a compound of Formula (III), or a pharmaceutically acceptable salt, solvate or prodrug thereof, refers to any optical purity of the compound of Formula (III), or a pharmaceutically acceptable salt, solvate or prodrug thereof, in the composition, including but not limited to optically pure compound or a pharmaceutically acceptable salt, solvate or prodrug thereof.

In some embodiments, the enantiomeric ratio of the compound of Formula (III), or a pharmaceutically acceptable salt, solvate or prodrug thereof, is greater than 90:10. In some embodiments, the enantiomeric ratio of the compound of Formula (III), or a pharmaceutically acceptable salt, solvate or prodrug thereof, is greater than 95:5. In some embodiments, the enantiomeric ratio of the compound of Formula (III), or a pharmaceutically acceptable salt, solvate or prodrug thereof, is greater than 99:1. In some embodiments, the compound of Formula (III), or a pharmaceutically acceptable salt, solvate or prodrug thereof, is optically pure.

An additional compound for use in any of the methods, uses, formulations or compositions described herein is 3-(3-hydroxyphenyl)-4-methyl-2-(4-(2-(3-methylazetidin-1-yl)ethoxy)phenyl)-2H-chromen-6-ol, or a pharmaceutically acceptable salt, solvate or prodrug thereof. In some embodiments, the (R) enatiomer of 3-(3-hydroxyphenyl)-4-methyl-2-(4-(2-(3-methylazetidin-1-yl)ethoxy)phenyl)-2H-chromen-6-ol, or a pharmaceutically acceptable salt, solvate or prodrug thereof, is used in any of the methods, uses, formulations or compositions described herein. Reference to a use of the (R)-enantiomer, or a pharmaceutically acceptable salt, solvate or prodrug thereof, or a composition that includes the (R)-enantiomer, or a pharmaceutically acceptable salt, solvate or prodrug thereof, refers to any optical purity of the (R)-enantiomer of the compound, or a pharmaceutically acceptable salt, solvate or prodrug thereof, in the composition, including but not limited to optically pure compound, or a pharmaceutically acceptable salt, solvate or prodrug thereof. In some embodiments, the enantiomeric ratio of the (R)-enantiomer of the compound, or a pharmaceutically acceptable salt, solvate or prodrug thereof, is greater than 90:10. In some embodiments, the enantiomeric ratio of the (R)-enantiomer of the compound, or a pharmaceutically acceptable salt, solvate or prodrug thereof, is greater than 95:5. In some embodiments, the enantiomeric ratio of the (R)-enantiomer of the compound, or a pharmaceutically acceptable salt, solvate or prodrug thereof, is greater than 99:1. In some embodiments, the (R)-enantiomer of the compound, or a pharmaceutically acceptable salt, solvate or prodrug thereof, is optically pure. In some embodiments, the (S) enatiomer of 3-(3-hydroxyphenyl)-4-methyl-2-(4-(2-(3-methylazetidin-1-yl)ethoxy)phenyl)-2H-chromen-6-ol, or a pharmaceutically acceptable salt, solvate or prodrug thereof, is used in any of the methods, uses, formulations or compositions described herein. Reference to a use of the (S)-enantiomer, or a pharmaceutically acceptable salt, solvate or prodrug thereof, or a composition that includes the (S)-enantiomer, or a pharmaceutically acceptable salt, solvate or prodrug thereof, refers to any optical purity of the (S)-enantiomer of the compound, or a pharmaceutically acceptable salt, solvate or prodrug thereof, in the composition, including but not limited to optically pure compound, or a pharmaceutically acceptable salt, solvate or prodrug thereof. In some embodiments, the enantiomeric ratio of the (S)-enantiomer of the compound, or a pharmaceutically acceptable salt, solvate or prodrug thereof, is greater than 90:10. In some embodiments, the enantiomeric ratio of the (S)-enantiomer of the compound, or a pharmaceutically acceptable salt, solvate or prodrug thereof, is greater than 95:5. In some embodiments, the enantiomeric ratio of the (S)-enantiomer of the compound, or a pharmaceutically acceptable salt, solvate or prodrug thereof, is greater than 99:1. In some embodiments, the enantiomeric ratio of the (S)-enantiomer of the compound, or a pharmaceutically acceptable salt, solvate or prodrug thereof, is greater than 99:1. In some embodiments, the (S)-enantiomer of the compound, or a pharmaceutically acceptable salt, solvate or prodrug thereof, is optically pure.

Synthesis

Compounds described herein are synthesized using standard synthetic techniques or using methods known in the art in combination with methods described herein. In additions, solvents, temperatures and other reaction conditions presented herein may vary.

The starting material used for the synthesis of the compounds described herein are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4$^{th}$, (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds can be modified by the use of appropriate reagents and conditions for the introduction of the various moieties found in the formulae as provided herein.

In some embodiments, the compounds described herein are prepared as outlined in the following Schemes.

Scheme 1:

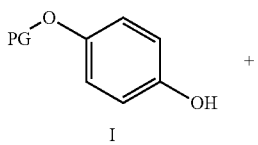

I

-continued

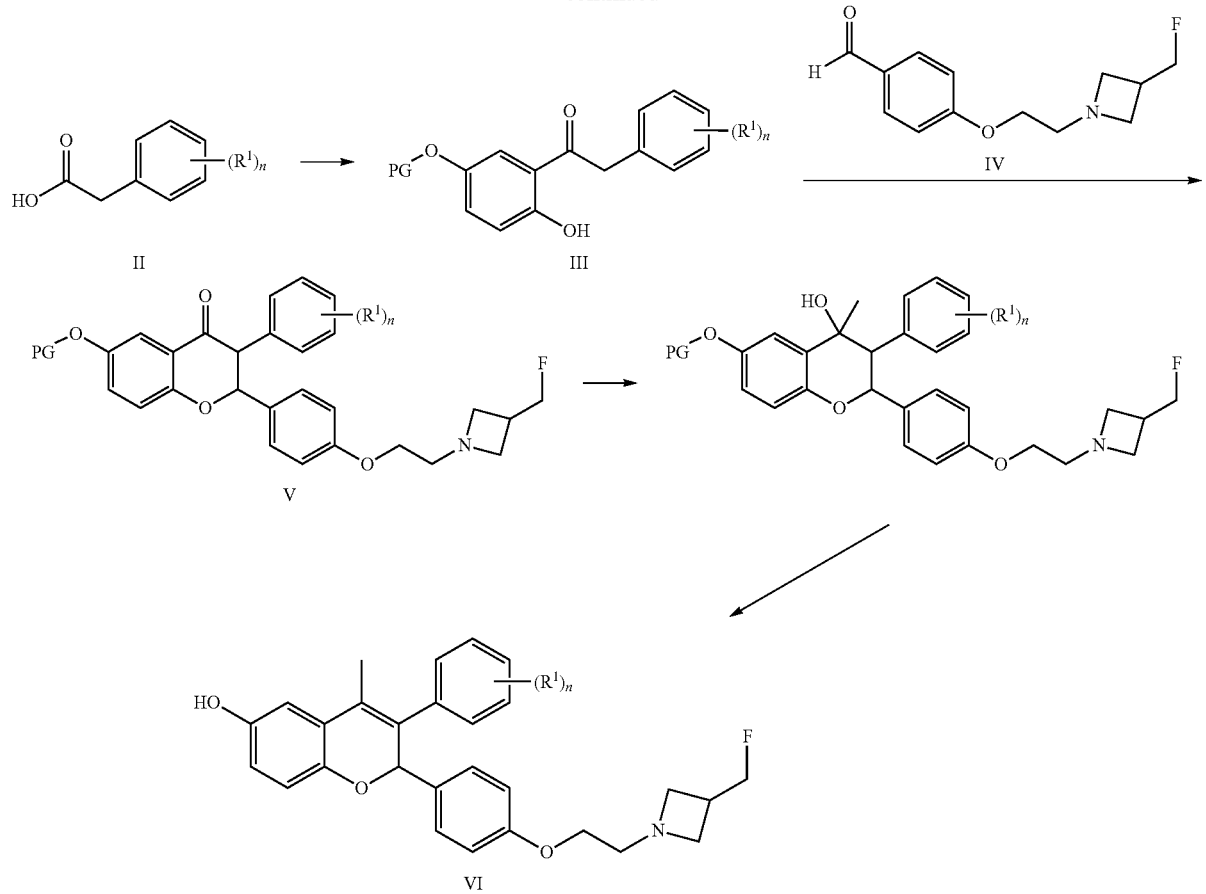

Treatment of phenols of structure I with phenylacetic acids of structure II in the presence of a suitable Lewis Acid in a suitable solvent provides ketones of structure III. PG represents any suitable phenol protecting group. In some embodiments, PG is methyl, benzyl, para-methoxybenzyl or tetrahydropyran. In some embodiments the suitable Lewis Acid is $BF_3$-$Et_2O$. In some embodiments, the suitable solvent is toluene, dichloromethane, or dichloroethane. In some embodiments, the reaction is heated. In some embodiments, the reaction is heated to 90° C.-100° C. Ketones of structure III are reacted with benzaldehydes of structure IV in the presence of a suitable base and suitable solvent to provide compounds of structure V. In some embodiments, the suitable base is piperidine and 1,8-diazabicyclo[5.4.0]undec-7-ene (DBU). In some embodiments, the suitable solvent is s-butanol, n-butanol, and/or i-propanol. In some embodiments, ketones of structure III are reacted with benzaldehydes of structure IV in the presence of piperidine, DBU in s-butanol at reflux for 3 hours and then i-propanol is added and the reaction is stirred at room temperature for 1-3 days. Compounds of structure V are treated with suitable organometallic reagents in a suitable solvent to provide tertiary alcohols that are then dehydrated to provide chromenes of structure VI. In some embodiments, the suitable organometallic reagent is methyl lithium, methyl magnesium chloride, methyl magnesium bromide or methyl magnesium iodide. In some embodiments, the suitable solvent for the formation of the tertiary alcohols is an aprotic solvent. In some embodiments, the aprotic solvent is tetrahydrofuran. The tertiary alcohol that is produced is then treated with acetic acid/water to eliminate to the chromene. In some embodiments, the tertiary alcohol is treated with acetic acid/water around 90° C. to eliminate to the chromene. The protecting groups are then removed under standard reaction conditions. For example, when PG is a benzyl group, then the benzyl group is removed with Pd/C, hydrogen gas, in methanol or ethyl acetate or acetic acid. Alternatively, when PG is a benzyl group, then the benzyl group is removed with a Lewis acid, such as aluminum trichloride. In some embodiments, when PG is a para-methoxybenzyl group, the para-methoxybenzyl group is removed with an acid, such as trifluoroacetic acid or hydrochloric acid. In some other embodiments, when PG is a tetrahydropyran group, then the tetrahydropyran group is removed with 80% acetic acid in water. In some embodiments, when PG is a methyl group, then the methyl group is removed with trifluoroborane-dimethylsulfide in dichloromethane.

In some embodiments, benzaldehydes of structure IV are prepared as outlined in Scheme 2.

Scheme 2.

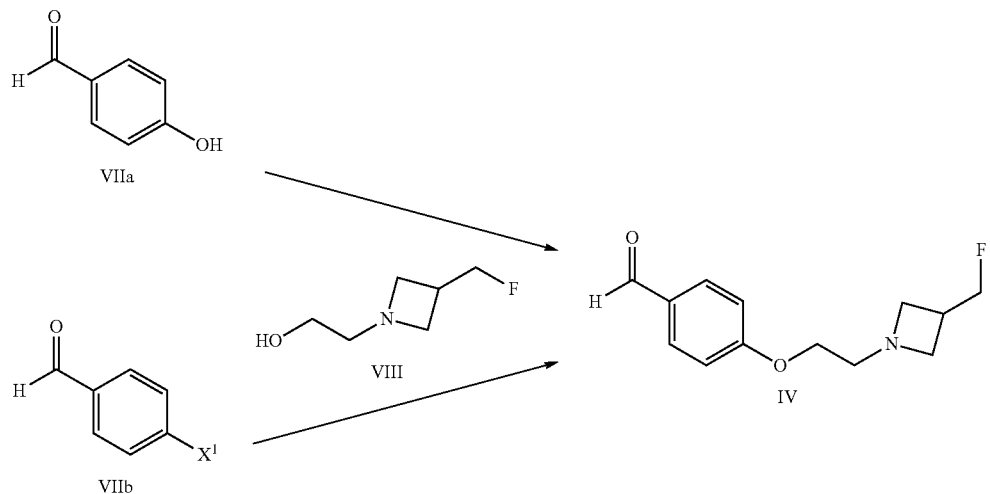

In some embodiments, 4-hydroxybenzaldehyde of structure VIIa is coupled with compound of structure VIII under suitable coupling conditions. In some embodiments, the suitable coupling conditions include the use of triphenylphosphine, diisopropyl azodicarboxylate and tetrahydrofuran. In some embodiments, the coupling is performed at room temperature.

In some embodiments, 4-halobenzaldehydes of structure VIIb (e.g. where $X^1$ is F, Cl, Br or I) are coupled with compound of structure VIII under suitable coupling conditions. In some embodiments, when $X^1$ is I then suitable Ullman reaction conditions are used to couple compounds of structure VIIb and VIII to provide compounds of structure IV. In some embodiments, when $X^1$ is I then the suitable reaction conditions include the use of CuI, potassium carbonate, butyronitrile with heating to about 125° C. In an alternative embodiment, when $X^1$ is I then the suitable reaction conditions include the use of CuI, 1,10-phenanthroline, cesium carbonate, m-xylenes, with heating to about 125° C. In some other embodiments, when $X^1$ is Cl, Br or I then the suitable palladium mediated reaction conditions are used to couple compounds of structure VIIb and VIII to provide compounds of structure IV. In some embodiments, when $X^1$ is Br then the suitable reaction conditions include the use of $Pd_2(dba)_3$, Xantphos, cesium carbonate, and dioxane, with heating to about 100° C.

In some embodiments, when $X^1$ is F or Cl then suitable $S_NAr$ reaction conditions are used to couple compounds of structure VIIb and VIII to provide compounds of structure IV. In some embodiments, suitable conditions for the $S_NAr$ reaction conditions include the use of a base such as sodium hydride or cesium carbonate and a solvent such as dimethylformamide, dimethylsulfoxide, or any other suitable aprotic solvent. In some embodiments, when $X^1$ is F then the suitable reaction conditions include the use of sodium hydride and dimethylformamide or cesium carbonate and dimethylsulfoxide with heating. In some embodiments, when $X^1$ is Cl then the suitable reaction conditions include the use of sodium hydride and dimethylformamide with heating.

In some embodiments, compounds are prepared as outlined in Scheme 3.

Scheme 3:

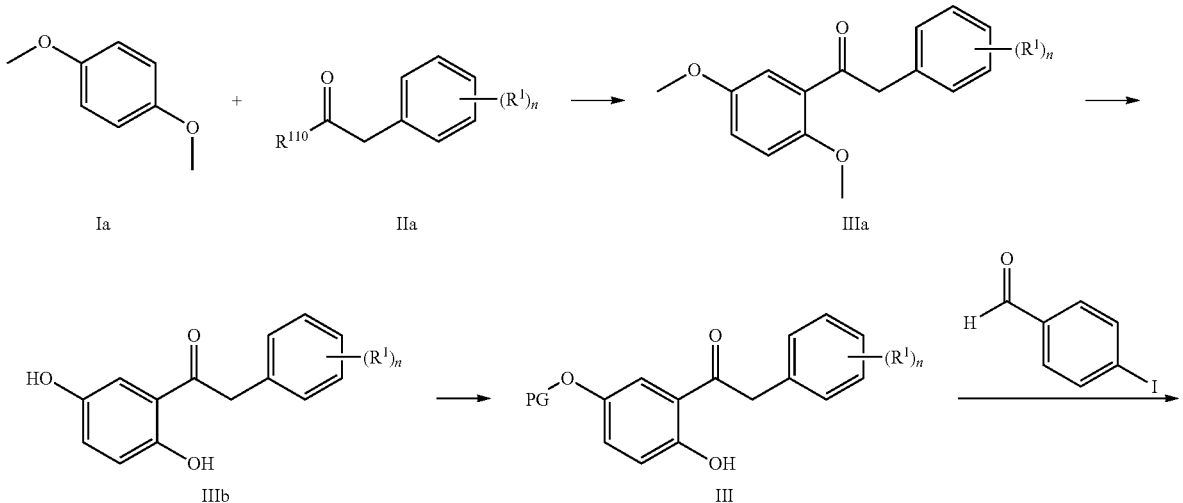

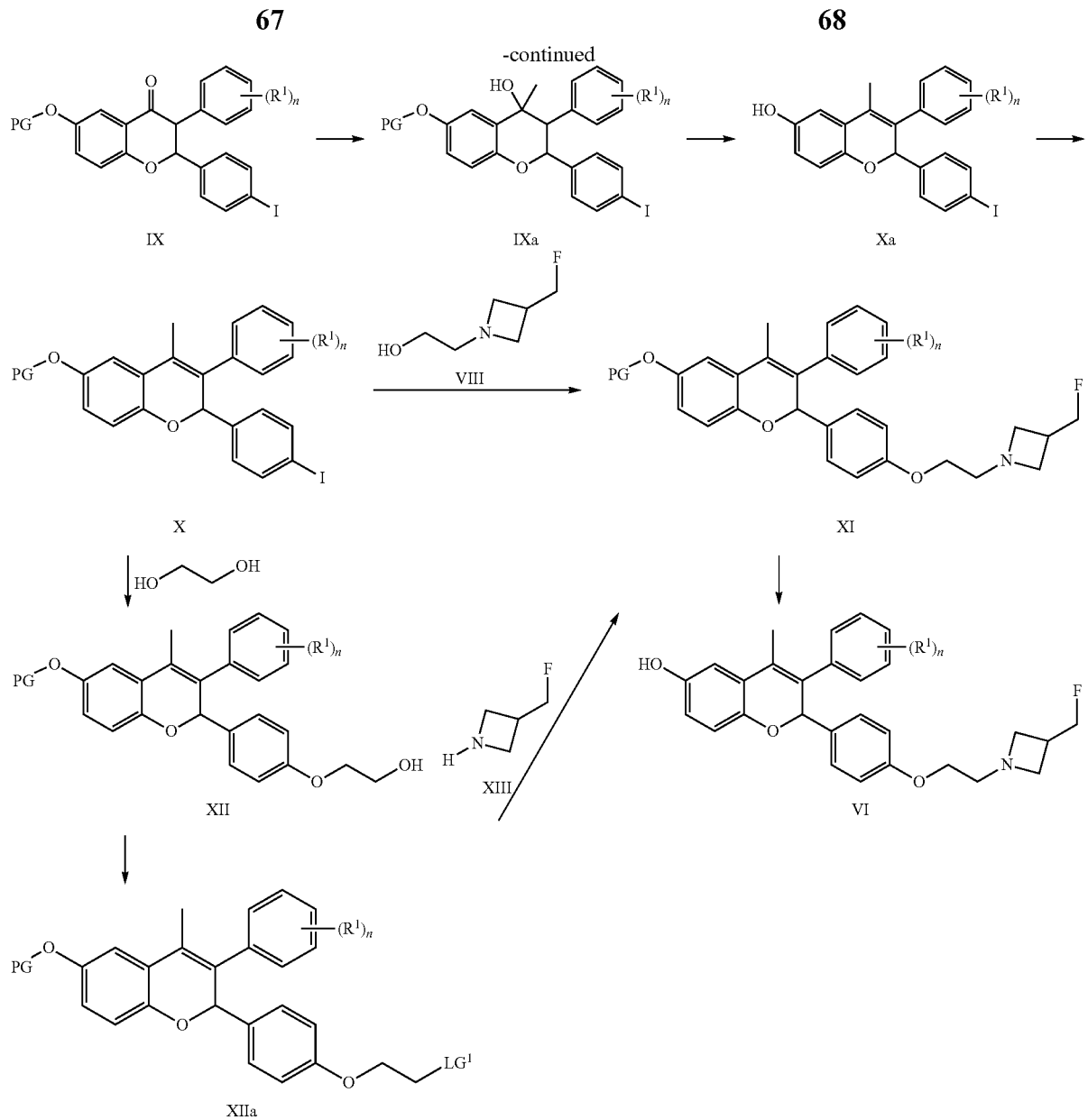

In some embodiments, ketones of structure III are prepared as outlined in Scheme 1 and then reacted with 4-iodobenzaldehyde of structure in the presence of a suitable base and suitable solvent to provide compounds of structure IX. In some embodiments, the suitable base is piperidine and 1,8-diazabicyclo[5.4.0]undec-7-ene (DBU). In some embodiments, the suitable solvent(s) is s-butanol and i-propanol. In other embodiments, ketones of structure III are prepared as outlined in Scheme 3 by starting with 1,4-dimethoxybenzene (Ia) and a compound of structure IIa (where $R^{110}$ is a halide, —OH, or —Oalkyl). In some embodiments, where $R^{110}$ is chloro, a compound of structure IIa and 1,4-dimethoxybenzene are treated with a suitable Lewis Acid and a suitable solvent to provide ketones of structure IIIa. In some embodiments, the suitable Lewis Acid is aluminum trichloride and the suitable solvent is dichloromethane. In some embodiments, where $R^{110}$ is —OH, a compound of structure IIa and 1,4-dimethoxybenzene are treated with polyphosphoric acid and heated. Removal of the methyl groups from the ketones of structure IIIa provides ketones of structure IIIb. In some embodiments, removal of the methyl groups is accomplished with the use of a suitable Lewis Acid. In some embodiments, the suitable Lewis Acids for the removal of the methyl groups is broron tribromide. Protection of the less sterically hindered hydroxyl group of ketones of structure IIIb provides ketones of structure III. In some embodiments, the PG of ketones of structure III is tetrahydropyran. Other suitable protecting groups are contemplated.

Compounds of structure IX are then treated with suitable organometallic reagents to provide tertiary alcohols of structure IXa, followed by dehydration of the tertiary alcohol to provide chromenes of structure Xa. In some embodiments, the suitable organometallic reagent is methyl lithium, methyl magnesium chloride, methyl magnesium bromide, or methyl magnesium iodide. In some embodiments, dehydration is accomplished with the use of 80% acetic acid in water at a temperature of about 90° C. The free hydroxyl group chromenes of structure Xa are protected with a protecting group. In some embodiments, the suitable protecting group is tetrahydropyran.

In some embodiments, compound of structure VIII is reacted with chromenes of structure X under Ullmann reaction conditions to give compound of structure XI followed by removal of the protecting groups PG to provide chromenes of structure VI. Ullmann reaction conditions include the use of copper salts. In some embodiments, the Ullmann reaction conditions include the use of CuI, $K_2CO_3$, and butyronitrile with heating to about 125° C. In some embodiments, the Ullmann reaction conditions include the use of CuI, $Cs_2CO_3$, 1,10-phenanthroline and m-xylenes with heating to about 125° C.

In an alternative embodiment, chromenes of structure X are reacted with ethane-1,2-diol under Ullmann reaction conditions to provide chromenes of structure XII, followed by conversion of the —OH to a suitable leaving group ($LG^1$) to provide chromenes of structure XIIa. In some embodiments, the Ullmann reaction conditions include the use of CuI, 1,10-phenanthroline, potassium carbonate, and m-xylenes with heating to about 125° C. Examples of suitable leaving groups ($LG^1$) include —Cl, —Br, —I, —OTf, —OMs, and —OTs. In some embodiments, the —OH is converted to —OMs by treating the —OH with methanesulfonyl chloride and triethylamine in dichloromethane at about 0° C. The leaving group of chromenes of structure XIIa is then displaced with the azetidine of structure XIII to provide chromenes of structure XI. Removal of the protecting groups PG of chromenes of structure XI provides chromenes of structure VI.

In some embodiments, ketones of structure III are prepared as outlined in Scheme 4:

Scheme 4:

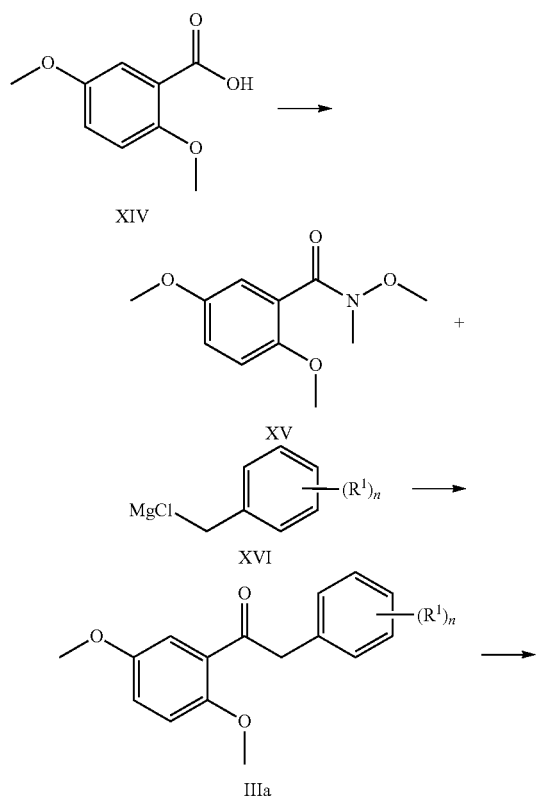

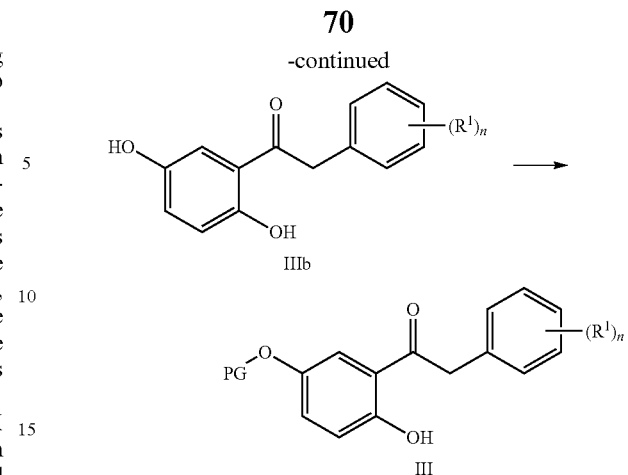

Benzoic acid compounds of structure XIV are converted to Weinreb amides of structure XV. In some embodiments, benzoic acid compounds of structure XIV are treated with oxalyl chloride, dimethylformamide (DMF), dichloromethane (DCM), at room temperature for about 2 hours followed by treatment with triethylamine ($Et_3N$), N,O-dimethylhydroxylamine-HCl, DCM, at 0° C. to room temperature for 1 hour to provide Weinreb amides of structure XV. Weinreb amides of structure XV are then treated with suitable organometallics reagents of structure XVI to provide ketones of structure IIIa. In some embodiments, ketones of structure IIIa are treated with $BBr_3$, DCM, −78° C. to 0° C. for about 30 minutes to provide ketones of structure IIIb. Alternatively, ketones of structure IIIa are treated with $AlCl_3$, DCM, 0° C. to room temperature for about 30 minutes to provide ketones of structure IIIb. In some embodiments, the less sterically hindered hydroxyl group of ketones of structure IIIb are protected with a suitable protecting group, such as tetrahydropyran.

In some embodiments, ketones of structure III are prepared as outlined in Scheme 5:

Scheme 5:

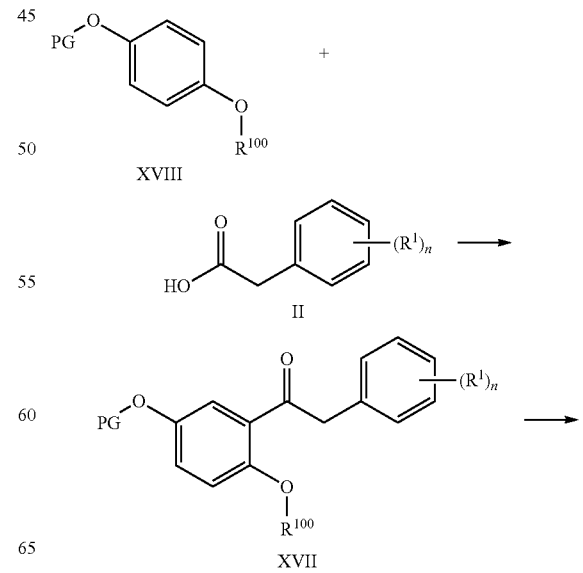

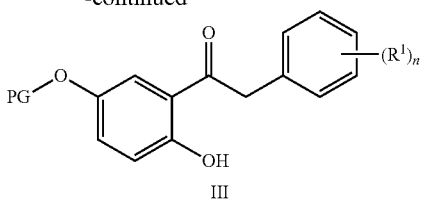

III

In some embodiments, suitably protected phenols of structure XVIII are treated with polyphosphoric acid and phenyl acetic acids of structure II to provide ketones of structure XVII. In some embodiments, $R^{100}$ is a phenol protecting group. In some embodiments, $R^{100}$ is methyl. Ketones of structure XVII are then converted to ketones of structure III as outlined in Scheme 4.

In some embodiments, ketones of structure III are prepared as outlined in Scheme 6:

Scheme 6:

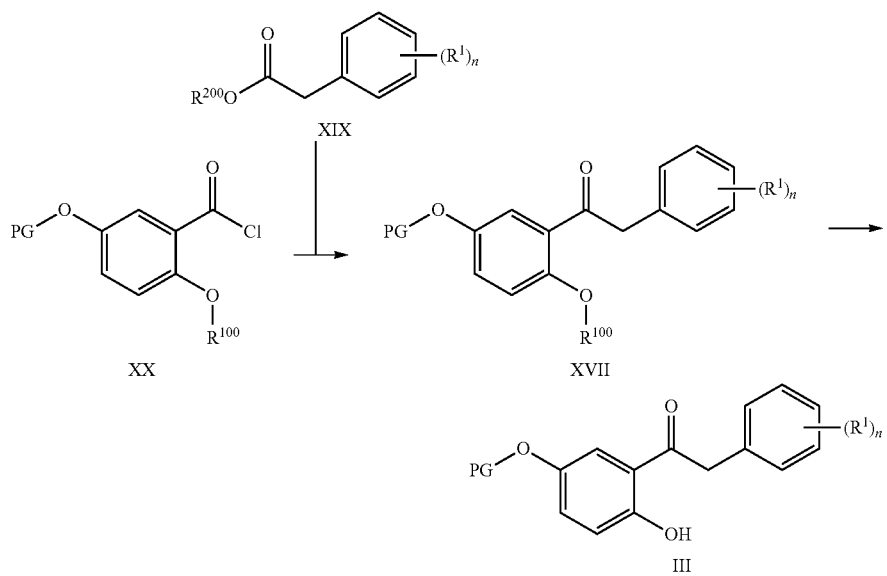

Alkyl esters of phenylacetic acids, such as compounds of structure XIX, are treated with a suitable base and then reacted with acid chlorides of structure XX to provide keto-esters that are decarboxylated to provide ketones of structure XVII. In some embodiments, $R^{100}$ is alkyl. In some embodiments, $R^{100}$ is methyl. In some embodiments, the suitable base is sodium hydride. In some embodiments, compounds of structure XIX are reacted with acid chlorides of structure XX in the presence of sodium hydride in tetrahydrofuran at 0° C. to room temperature. In other embodiments, the suitable base is lithium bis(trimethylsilyl) amide (LiHMDS). In some embodiments, compounds of structure XIX are treated with LiHMDS in tetrahydrofuran at −78° C. and then reacted with acid chlorides of structure XX and the reaction mixture is warmed to room temperature. In some embodiments, decarboxylation of the ketoester is accomplished using Krapcho decarboxylation condition. In some embodiments, Krapcho decarboxylation conditions include dimethylsulfoxide, brine or lithium chloride with heating to about 150° C. Other decarboxylation conditions include the use of concentrated hydrochloric acid in water or ethanol with heating. $R^{100}$ is then removed from ketones of structure XVII as described in Scheme 4 to provide ketones of structure III.

In some embodiments, ketones of structure III are prepared as outlined in Scheme 7.

Scheme 7.

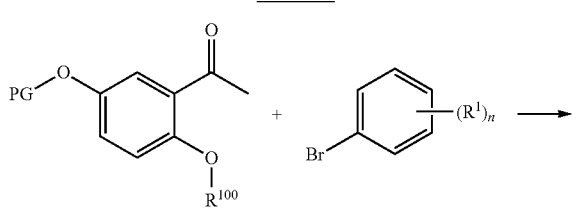

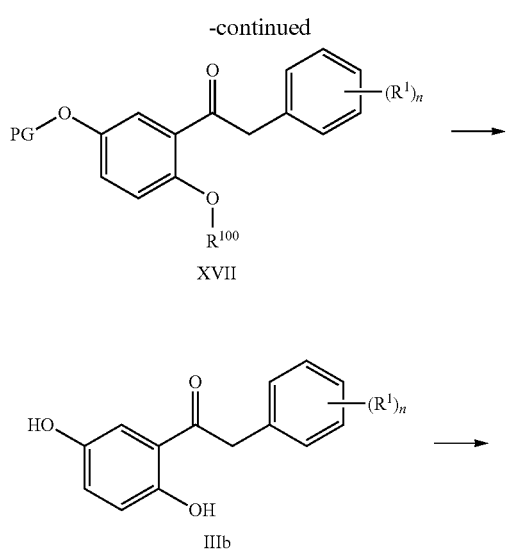

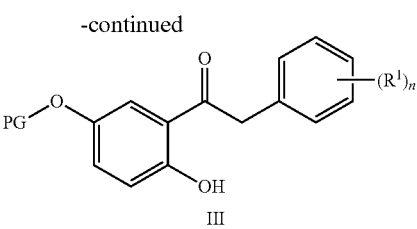

In some embodiments, a palladium mediated coupling reaction between suitable acetophenones and phenyl halides provides ketones of structure XVII. In some embodiments, the palladium mediated coupling conditions includes the use of $Pd_2(dba)_3$, BINAP, sodium tert-butoxide, tetrahydrofuran at 70° C. Ketones of structure XVII are then transformed to ketones of structure III as described above.

In some embodiments, the substituted azetidine is prepared as outlined in Scheme 8.

embodiments, when $R^{300}$ is Cbz then the deprotection is performed using Pd/C, hydrogen gas, methanol or hydrochloric acid, dioxane and heat. In some embodiments, when $LG^1$ is —OMs then the suitable reaction conditions include the use of potassium carbonate (or cesium carbonate or sodium hydroxide or diisopropylethylamine) and acetonitrile (or methanol, ethanol, isopropanol, tetrahydrofuran or dioxane) with optional heating. In some embodiments, when $LG^1$ is —OMs then the suitable reaction conditions include performing the reaction neat (i.e. amine as solvent) with heating. In some embodiments, when $LG^1$ is —OTf then the suitable reaction conditions include the use of diisopropylethylamine and dichloromethane with the reaction initial performed at −78° C. then warming to room temperature. In some embodiments, when $LG^1$ is Br and $R^{200}$ is H, then the suitable reaction conditions include the use of sodium hydroxide, in tetrahydrofuran/water at room temperature. In some other embodiments, when $LG^1$ is Br and $R^{200}$ is H,

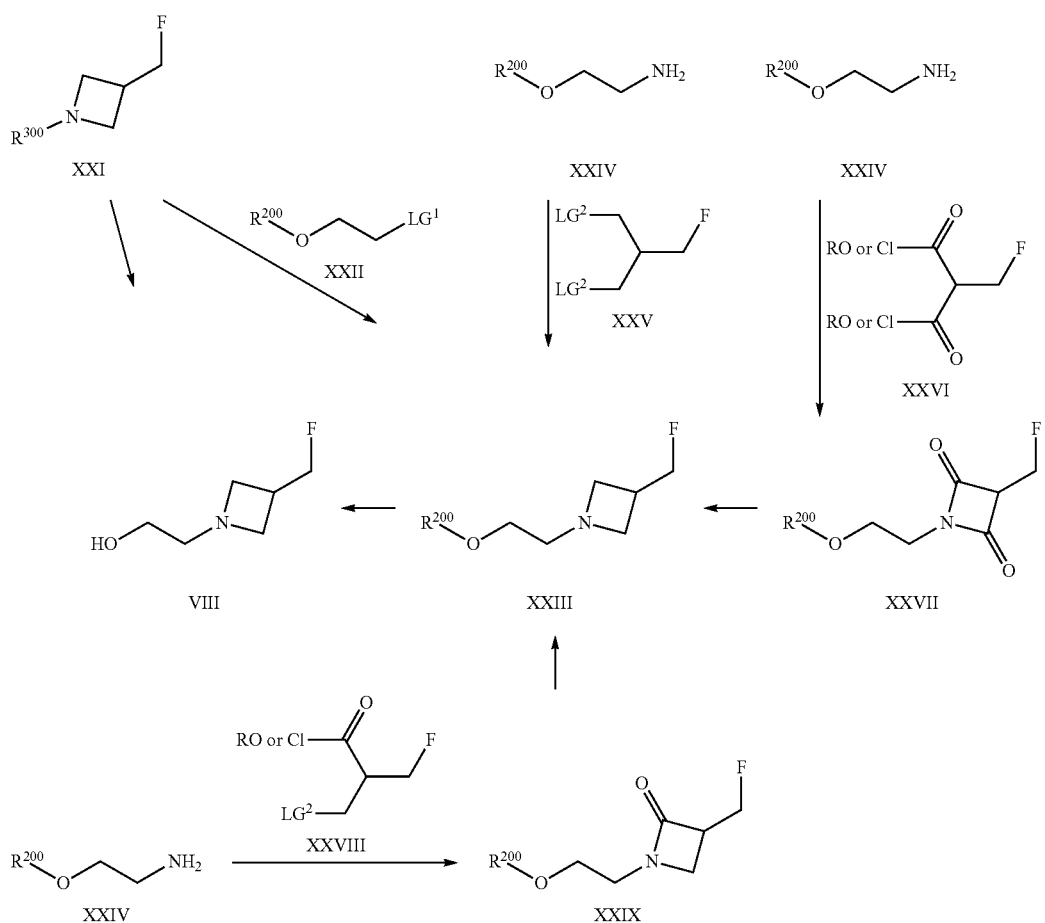

In some embodiments, azetidines of structure XXI, where $R^{300}$ is a protecting group such as t-BOC or Cbz, are first deprotected and then reacted with compounds of structure XXII, where $LG^1$ is a leaving group, under suitable reaction conditions to provide compounds of structure XXIII. In some embodiments, when $R^{300}$ is t-BOC then the deprotection is performed using hydrochloric acid in methanol or dioxane at room temperature or using trifluoroacetic acid in dichloromethane at room temperature. In some other then the suitable reaction conditions include the use of 1,8-diazabicyclo[5.4.0]undec-7-ene (DBU) in tetrahydrofuran at room temperature. In some other embodiments, when $LG^1$ is Br and $R^{200}$ is H, then the reaction conditions include performing the reaction in neat triethylamine or diisoproylethylamine at room temperature.

In some embodiments, $R^{200}$ is a suitable protecting group and includes, but is not limited, tetrahydropyran (THP), benzyl, trialkylsilyl, or trityl. In some embodiments, $R^{200}$ is removed from compounds of structure XXIII to provide VIII. In some embodiments, when $R^{200}$ is benzyl, then the benzyl is removed using Pd/C, hydrogen gas, in methanol or ethyl acetate or acetic acid. In some other embodiments, when $R^{200}$ is benzyl, then the benzyl is removed with Lewis acids such as $AlCl_3$. In some embodiments, when $R^{200}$ is THP, then the THP is removed using 80% acetic acid in water. In some embodiments, when $R^{200}$ is trityl, then the trityl is removed with hydrochloric acid in tetrahydrofuran/water.

In another embodiment, protecting group $R^{300}$ of azetidines of structure XXI is first removed and the resulting amine is reacted with ethane-1,2-diol under transition metal mediated reaction conditions to provide compound of structure VIII. In some embodiments, the transition metal mediated reaction conditions include the use of ruthenium or iridium catalysts.

Alternatively, reaction of amines of structure XXIV with activated alkanes of structure XXV, where $LG^2$ is a suitable leaving group, under suitable reaction conditions provides compounds of structure XXIII. Suitable leaving groups include, chloro, bromo, iodo, tosylate (—OTs), mesylate (—OMs), and triflate (—OTf). In some embodiments, when $LG^2$ is OMs, then the suitable reaction conditions include the use of potassium carbonate and acetonitrile with the reaction performed at room temperature to 80° C. In some embodiments, when $LG^2$ is OTf, then the suitable reaction conditions include the use of dichloromethane and diisopropylethylamine at −78° C. followed by heating. In some embodiments, when $LG^2$ is a halogen, then the suitable reaction conditions include the use of potassium carbonate and acetonitrile at room temperature followed by heating. In other embodiments, the suitable reaction conditions include performing the reaction without added solvent or base (i.e. neat conditions).

Alternatively, reaction of diacids of structure XXVI (R=H) with acetic anhydride at about 85° C. for about 30 minutes provides an anhydride which is then treated with amines of structure XXIV followed by acetic anhydride to provide imides of structure XXVII. In some other embodiments, diacid chlorides of structure XXVI are reacted with amines of structure XXIV in the presence of diisopropylethylamine in dichloromethane at 0° C. to provide imides of structure XXVII. In yet other embodiments, alkyl diesters of structure XXVI are reacted with amines of structure XXIV in the presence of ethanol or isopropanol with heating or aluminum trichloride or trimethylaluminium in toluene. Imides of structure XXVII are then reduced to provide amines of structure XXIII. In some embodiment, the reduction is performed with lithium aluminum hydride in tetrahydrofuran or DIBAL in tetrahydrofuran. Other suitable reduction conditions include the use of $BH_3$—$SMe_2$, dicloromethane, with heating.

In some embodiments, amines of structure XXIV are reacted with compounds of structure XXVIII under suitable reaction conditions to provide amide compounds of structure XXIX. In some embodiments, the suitable reaction conditions include the use of potassium carbonate in tetrahydrofuran or dimethylformamide. In some embodiments, when $LG^2$ is OMs, then the suitable reaction conditions include the use of potassium carbonate and acetonitrile at room temperature to about 80° C. In some embodiments, when $LG^2$ is OTf, then the suitable reaction conditions include the use of dichloromethane and diisopropylethylamine at −78° C. to heat. In some embodiments, when $LG^2$ is halogen, then the suitable reaction conditions include the use of potassium carbonate and acetonitrile at room temperature to heat. In some embodiment, amides of structure XXIX are then reduced to provide amines of structure XXIII as described above.

In some embodiments, fluorinated azetidines are prepared as outlined in Scheme 9.

Scheme 9.

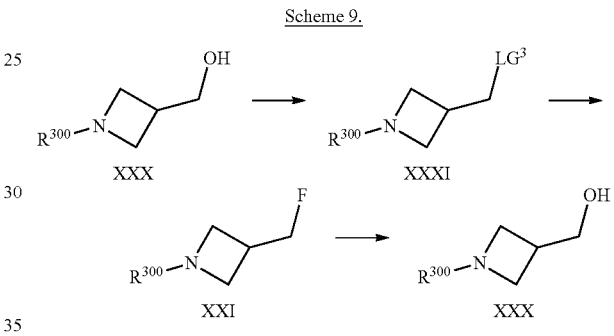

$R^{300}$ is a suitable protecting group for the nitrogen atom of the azetidine. In some embodiments, $R^{300}$ is t-BOC or Cbz. In some embodiments, when $R^{300}$ is t-BOC, then the compound of structure XXX is treated with methanesulfonyl chloride, triethylamine, and dichloromethane at 0° C. to provide compounds of structure XXXI where $LG^3$ is OMs. In some embodiments, when $R^{300}$ is Cbz, then the compound of structure XXX is treated with triflic anhydride, diisopropylethylamine, and dichloromethane at −78° C. to provide compounds of structure XXXI where $LG^3$ is OTf. In some embodiments, when $R^{300}$ is t-BOC and $LG^3$ is OMs, then the compound of structure XXXI is treated with tetrabutylammonium fluoride in tetrahydrofuran at reflux to provide compounds of structure XXI. Alternatively compounds of structure XXI can be prepared directly from compounds of structure XXX by use of diethylaminosulfur trifluoride in dichloromethane at −78° C. to room temperature.

In some embodiments, azetidine of structure VIII is prepared as outlined in Scheme 10.

Scheme 10.

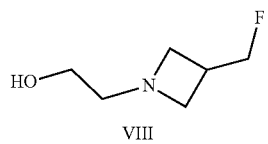

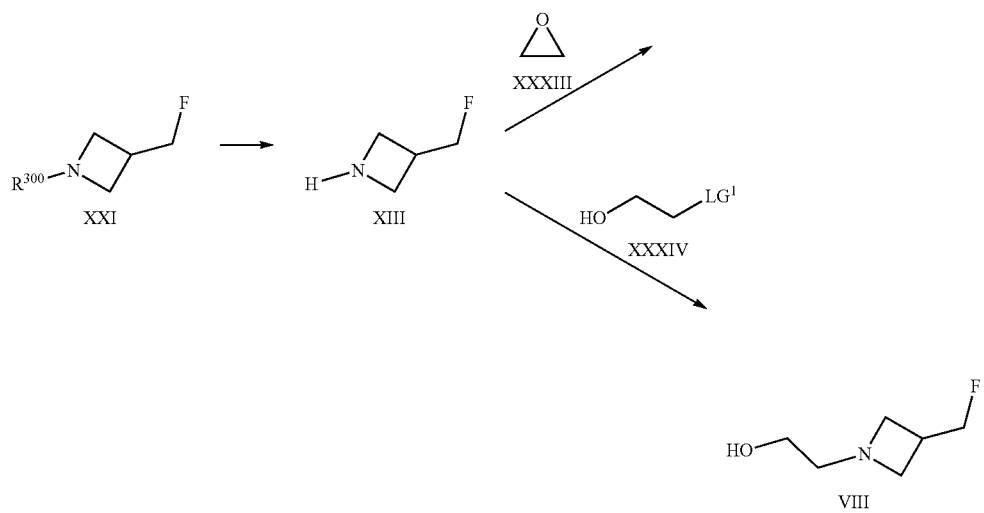

Azetidines of structure XXI, where $R^{300}$ is a protecting group such as t-BOC or Cbz, are deprotected to provide an azetidine of structure XIII. In some embodiments, when $R^{300}$ is t-BOC then the deprotection is performed using hydrochloric acid in methanol or dioxane at room temperature or using trifluoroacetic acid in dichloromethane at room temperature. In some other embodiments, when $R^{300}$ is Cbz then the deprotection is performed using Pd/C, hydrogen gas, methanol or hydrochloric acid, dioxane and heat.

In some embodiments, azetidine of structure XIII is reacted with epoxide of structure XXXIII under suitable reaction conditions to provide azetidine of structure VIII. In some embodiments, the suitable reaction conditions include the use of diisopropylethylamine and dichloromethane at room temperature or the suitable reaction conditions include the use of sodium hydroxide and tetrahydrofuran/water at room temperature or alternatively, the suitable reaction conditions include the use of triethylamine, $LiClO_4$, and acetonitrile or dichloromethane, at 0° C. to room temperature.

In other embodiments, azetidine of structure XIII is reacted with compounds of structure XXXIV under suitable reaction conditions to provide azetidine of structure VIII. $LG^1$ is a suitable leaving group. Suitable leaving groups include, chloro, bromo, iodo, tosylate (—OTs), mesylate (—OMs), and triflate (—OTf). In some embodiments, when $LG^1$ is Br or I, then the suitable reaction conditions include the use of any one of the following: (i) sodium hydroxide, tetrahydrofuran/water; or (ii) sodium hydroxide, potassium iodide, tetrahydrofuran/water; or (iii) sodium hydroxide, tetrabutylammonium iodide, tetrahydrofuran/water, room temperature to 50° C.; or (iv) diisopropylethylamine, acetonitrile, room temperature to 80° C.; (v) triethylamine, tetrahydrofuran, room temperature to reflux; or (vi) 1,8-diazabicyclo[5.4.0]undec-7-ene (DBU) in tetrahydrofuran at room temperature; vii) neat amines (e.g. triethylamine or diisopropylethylamine).

In some other embodiments, azetidine of structure VIII is prepared as outlined in Scheme 11.

Scheme 11

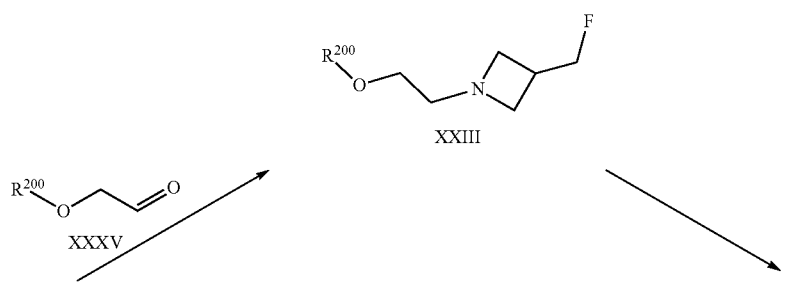

-continued

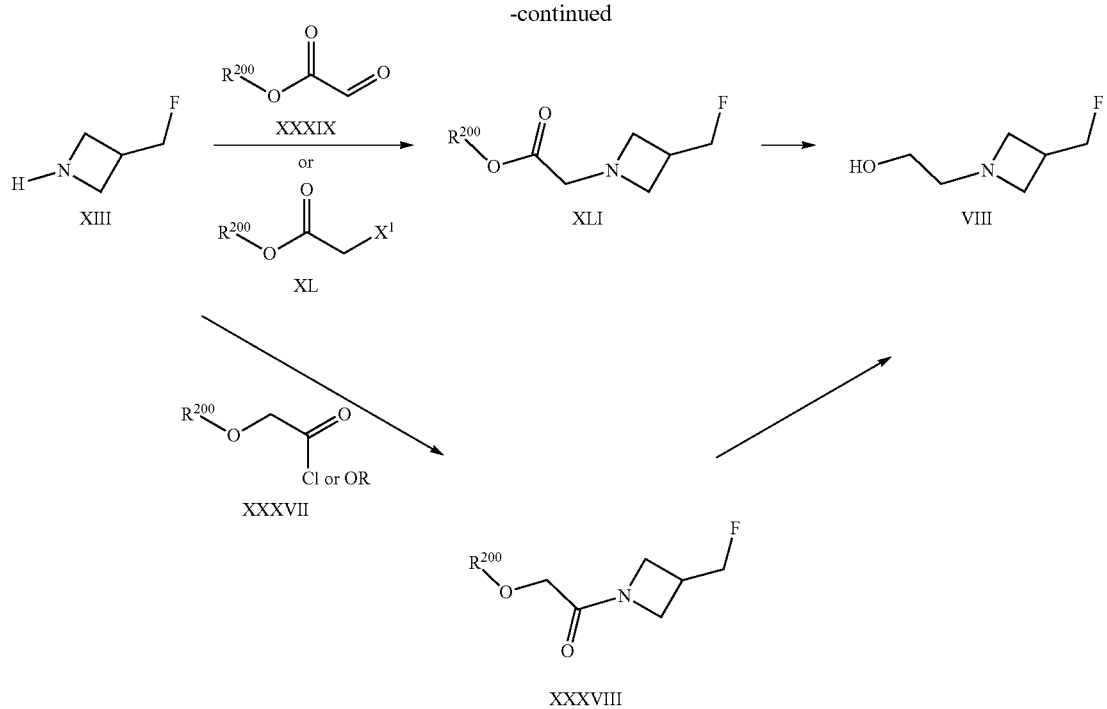

In some embodiments, an azetidine of structure XIII is reacted with aldehydes of structure XXXV under suitable reductive conditions to provide compounds of structure XXIII. Suitable reductive conditions include the use of: (i) NaBH(OAc)$_3$, acetic acid, and tetrahydrofuran; or (ii) NaCNBH$_4$, NaOAc, and ethanol at 0° C. to room temperature. Removal of the R$^{200}$ group of compounds of structure XXIII proceeds as outlined in Scheme 8 to provide azetidine compound of structure VIII.

In some other embodiments, an azetidine of structure XIII is coupled with compounds of structure XXXVII (where R$^{200}$ is a suitable alcohol protecting group and R is an alkyl) to provide compounds of structure XXXVIII. In some embodiments, the coupling conditions include the use of triethylamine and tetrahydrofuran at 0° C. to room temperature or diisopropylethylamine and dichloromethane at room temperature or pyridine and dichloromethane at 0° C. Reduction of the amide and deprotection of the R$^{200}$ protecting group of compounds of structure XXXVIII provides compound of structure VIII. In some embodiments, R$^{200}$ is acetyl and reduction of the amide of compounds of structure XXXVIII is performed with lithium aluminum hydride in tetrahydrofuran at 0° C. to provide compound of structure VIII In an alternative embodiment, azetidine of structure XIII is coupled with: (i) aldehydes of structure XXXIX under reductive amination conditions; or (ii) compounds of structure XL (where X' is a leaving group such as Cl, Br or I); to provide compounds of structure XLI. Reduction of the alkyl ester of compound of structure XLI to the alcohol provides VIII. In some embodiments, an azetidine of structure XIII is coupled with aldehydes of structure XXXIX under reductive amination conditions that include the use of NaBH(OAc)$_3$, NaOAc, and dichloromethane. In some embodiments, azetidine of structure XIII is coupled with alkyl esters of structure XL with the use of potassium carbonate and acetonitrile at room temperature or triethylamine and tetrahydrofuran at 0° C. to room temperature or diisopropylethylamine and dichloromethane at room temperature. Suitable reaction conditions for the reduction of the alkyl ester to the alcohol include the use of lithium aluminum hydride, lithium borohydride, sodium borohydride or diisobutylaluminum hydride in a suitable solvent.

In some embodiments, azetidine of structure VIII is prepared as outlined in Scheme 12.

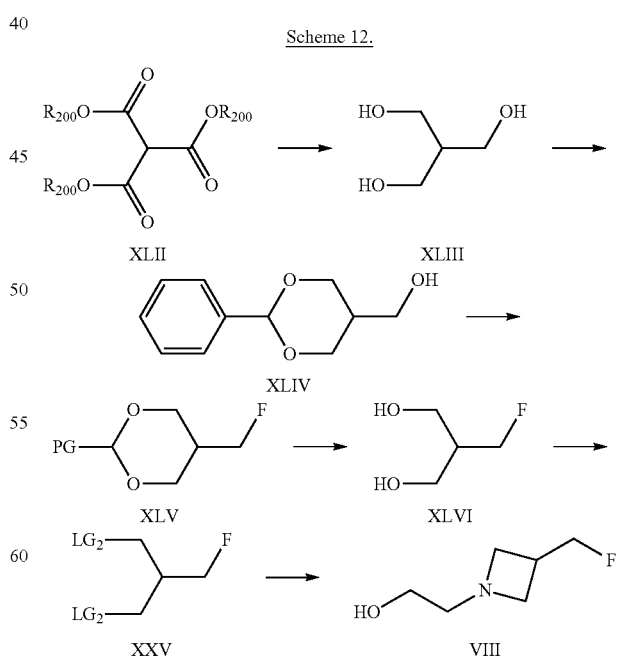

Scheme 12.

Tris(hydroxymethyl)methane of structure XLIII is treated with benzaldehyde, toluenesulfonic acid, dichloromethane and heat to provide compound of structure XLIV. The hydroxyl group of compound of structure XLIV is then converted to a fluoride group by a two step process that first includes activating the hydroxyl group to a suitable leaving group and then treatment with a suitable source of fluoride ions. In some embodiments, compound of structure XLIV is treated with methanesulfonyl chloride, triethylamine, dichloromethane at 0° C. and then treated with tetrabutylammonium fluoride, tetrahydrofuran at reflux to provide compound of structure XLV. Compound of structure XLV is then treated with an acid to provide diol of structure XLVI. In one embodiment, compound of structure XLV is treated with: (i) hydrochloric acid, methanol, at room temperature; or (ii) hydrochloric acid, water, at room temperature to provide diol of structure XLVI.

In some embodiments, diol of structure XLVI is treated with methanesulfonyl chloride, triethylamine, dichloromethane at 0° C. to room temperature to provide compound of structure XXV, where $LG^2$ is OMs. Alternatively, diol of structure XLVI is treated with triflic anhydride, diisopropylethylamine, dichloromethane, at −78° C. to room temperature to provide compound of structure XXV, where $LG^2$ is OTf. In some embodiments, compound of structure XXV is treated with 2-aminoethanol, acetonitrile, potassium carbonate, with heating to provide azetidine of structure VIII. Other aminoalcohols (e.g. 2-(benzyloxy)ethanamine or compounds of structure XXIV) are reacted with compound of structure XXV as outlined in Scheme 8 to provide azetidine of structure VIII. In some embodiments, when $LG^2$ is OMs then compound of structure XXV is treated with a suitable aminoalcohol under neat conditions.

In some embodiments, compounds of structure VI are prepared as described in Scheme 13.

In some embodiments, compounds of structure XLVII are treated with compound of structure VIII under suitable coupling conditions to provide compounds of structure XI. In some embodiments, the suitable coupling conditions include the use of triphenylphosphine, diisopropyl azodicarboxylate and tetrahydrofuran. In some embodiments, the coupling is performed at room temperature. In some embodiments, PG is methyl or tetrahydropyran.

Alternatively, reaction of phenols of structure XLVII with activated alkanes of structure VIIIa, where LG is a suitable leaving group, under suitable reaction conditions provides compounds of structure XI. Suitable leaving groups include, chloro, bromo, iodo, tosylate (—OTs), mesylate (—OMs), and triflate (—OTf). In some embodiments, when LG is Cl or Br, then then the suitable reaction conditions include the use of potassium carbonate and acetonitrile (or acetone) with the reaction performed at room temperature to reflux.

Deprotection of the protecting group from compounds of structure XI provides compounds of structure VI. In some embodiments, when PG is tetrahydropyran then the deprotection reaction is performed with the use of 80% acetic acid in water at room temperature. In some embodiments, when PG is methyl then the deprotection reaction is performed with the use of boron trifluoride-dimethyl sulfide in dichloromethane at room temperature.

In some embodiments, the phenols of structure XLVII are prepared as outlined in Scheme 14.

Scheme 13.

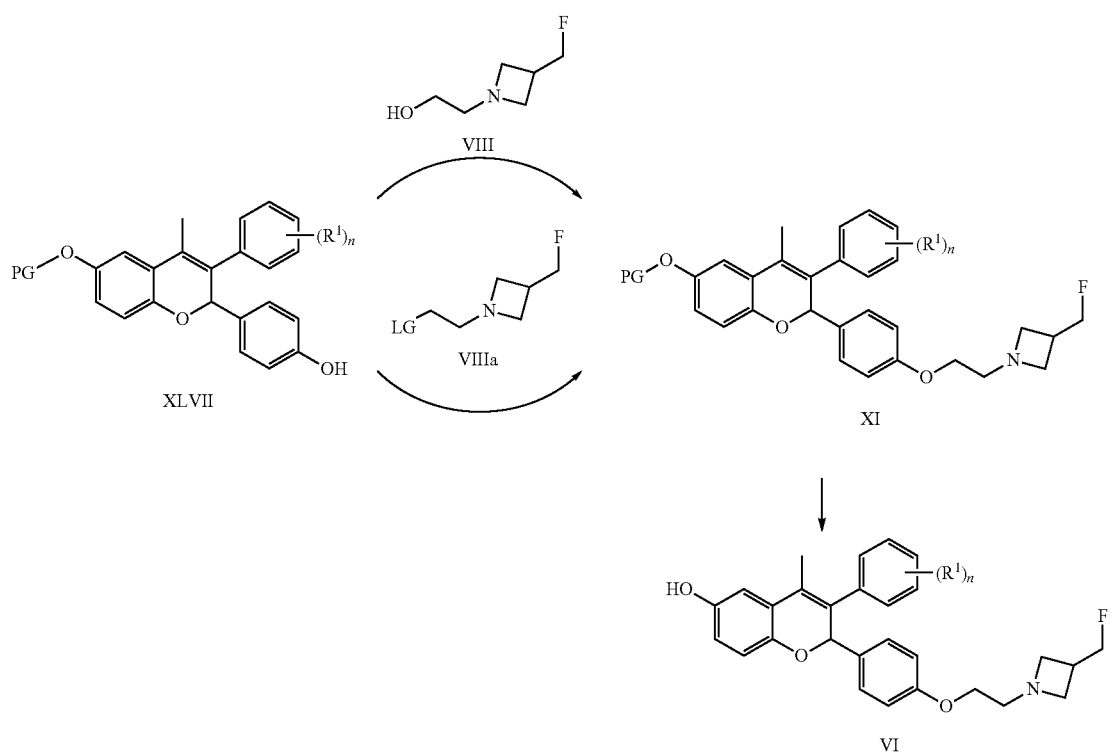

Scheme 14.

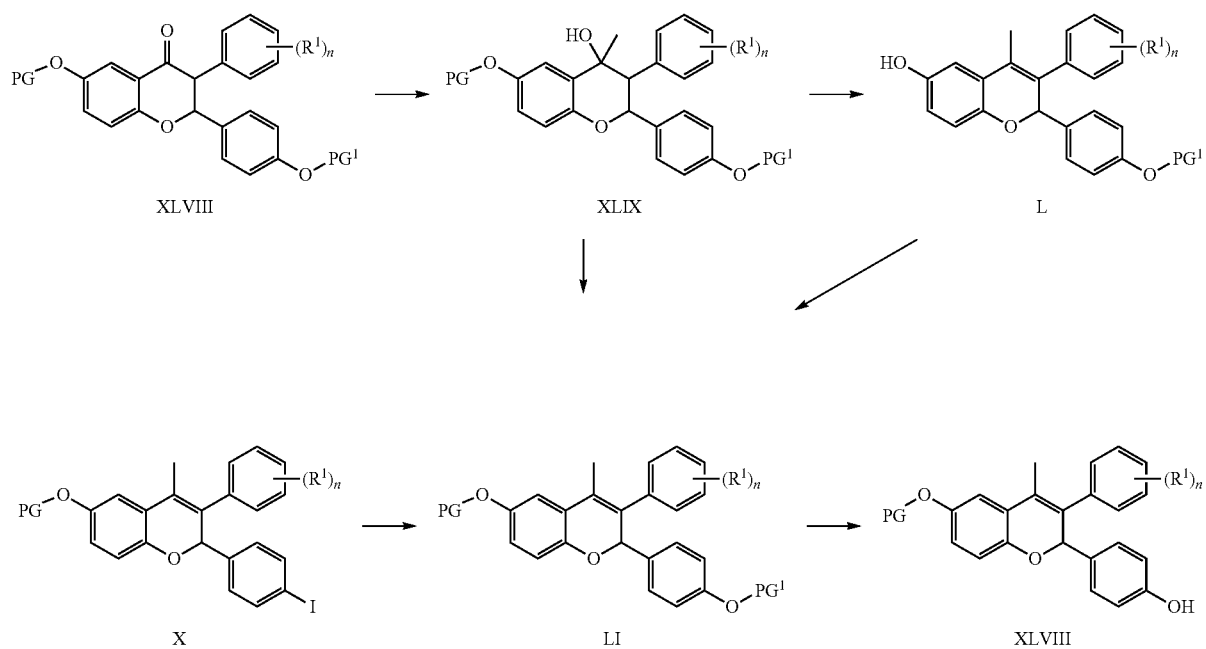

In some embodiments, compounds of structure XLVIII are treated with suitable organometallic reagents in a suitable solvent to provide tertiary alcohols of structure XLIX. In some embodiments, the suitable organometallic reagent is methyl lithium, methyl magnesium chloride, methyl magnesium bromide or methyl magnesium iodide. In some embodiments, the suitable solvent for the formation of the tertiary alcohols is an aprotic solvent. In some embodiments, the aprotic solvent is tetrahydrofuran.

In some embodiments, when PG is tetrahydropyran and $PG^1$ is allyl or benzyl, then tertiary alcohols of structure XLIX are treated with 80% acetic acid in water at about 90° C. to provide compounds of structure L. In some embodiments, compounds of structure L are treated with dihydropyran, pyridinium p-toluenesulfonate (PPTS) in dicloromethane at room temperature to provide compounds of structure LI, where PG is tetrahydropyran.

In some embodiments, selective removal of the $PG^1$ protecting group from compounds of structure LI provides compounds of structure XLVII. In some embodiments, when $PG^1$ is allyl and PG is tetrahydropyran, then compounds of structure LI are treated with tetrakis(triphenylphosphine)palladium(0), pyrrolidine in tetrahydrofuran at room temperature to provide compounds of structure XLVII. In some embodiments, when $PG^1$ is benzyl and PG is tetrahydropyran, then compounds of structure LI are treated with palladium on carbon, hydrogen gas in methanol at room temperature to provide compounds of structure XLVII.

In some embodiments, the protecting groups of compounds of structure XLIX are stable under acidic conditions and remain intact during the dehydration step of the tertiary alcohol. In some embodiments, suitable protecting groups that are stable under acidic conditions include instances where PG is methyl or benzyl and instances where $PG^1$ is allyl.

An alternative method to access compounds of structure LI includes the reaction of compounds of structure X with suitable alcohols under copper catalyzed reaction conditions. In some embodiments, compounds of structure X are reacted with allyl alcohol or benzyl alcohol in the presence of copper iodide, potassium carbonate, 1,10-phenanthroline, toluene (or xylenes) at a temperature of about 110-120° C. to provide compounds of structure LI.

In some embodiments, compounds of structure XLVIII are prepared as outline in Scheme 15.

Scheme 15.

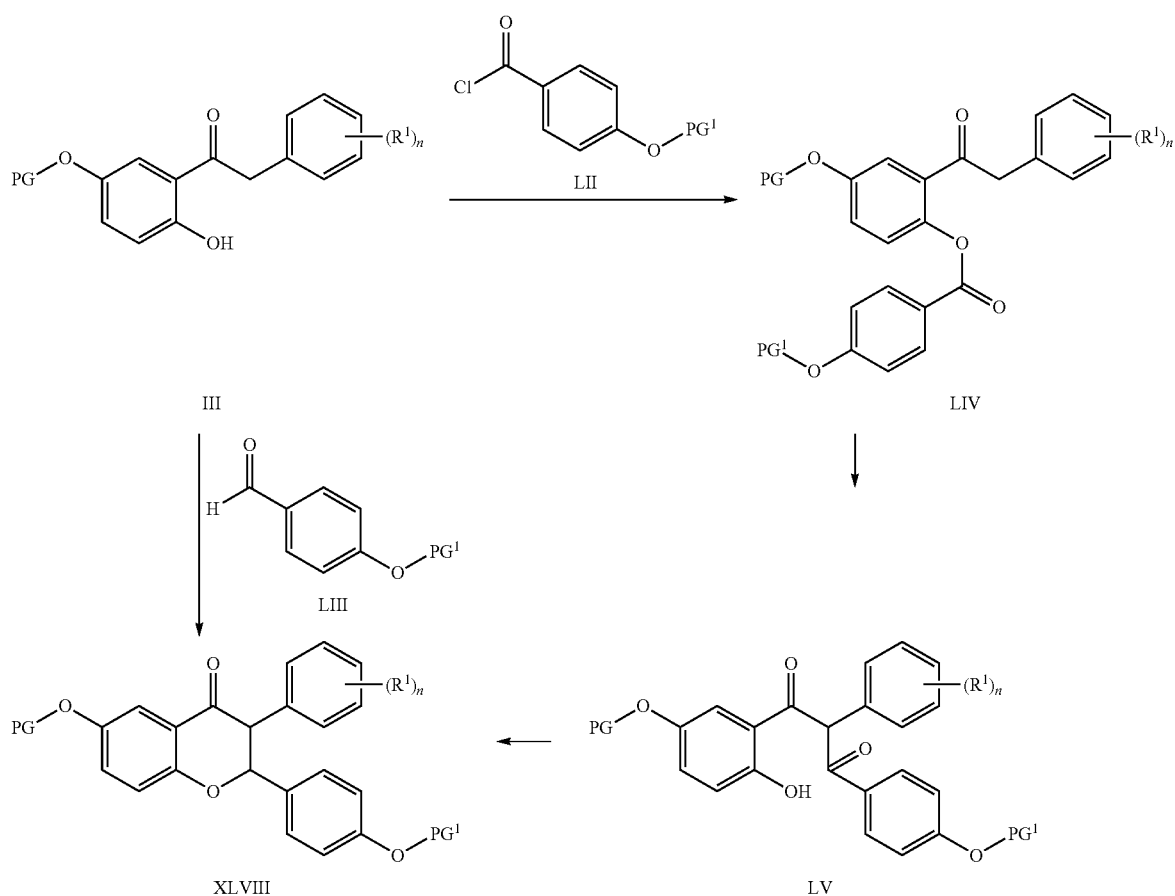

In some embodiments, benzoyl chlorides of structure LII are reacted with compounds of structure III to provide compounds of structure LIV. In some embodiments, the reaction conditions to prepare compounds of structure LIV include the use of triethylamine in tetrahydrofuran at 0° C. to room temperature. Compounds of structure LIV are treated with lithium diisopropylamide or lithium bis(trimethylsilyl)amide in tetrahydrofuran at −78° C. to room temperature to provide compounds of structure LV. Treatment of compounds of structure LV with trifluoroacetic acid and tri ethylsilane in dichloromethane at 0° C. to room temperature provides compounds of structure XLVIII.

Alternatively, compounds or structure III are reacted with benzaldehydes of structure LIII under suitable reaction conditions to provide compounds of structure XLVIII. In some embodiments, the suitable reaction conditions include the use of 1,8-diazabicyclo[5.4.0]undec-7-ene, piperidine, and s-butanol at a temperature of about 120° C.

In one aspect, compounds described herein are synthesized as outlined in the Examples.

Throughout the specification, groups and substituents thereof are chosen by one skilled in the field to provide stable moieties and compounds.

A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Further Forms of Compounds

In one aspect, compounds described herein exist as a racemic mixture or in enantiomerically enriched or enantiomerically pure form. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In certain embodiments, compounds described herein are prepared as their individual stereoisomers by enzymatic resolution. In some embodiments, resolution of individual stereoisomers is carried out using a lipase or an esterase. In some embodiments, resolution of individual stereoisomers is carried out by lipase or esterase-catalyzed asymmetric deacylation. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley and Sons, Inc., 1981. In some embodiments, stereoisomers are obtained by stereoselective synthesis.

The methods and compositions described herein include the use of amorphous forms as well as crystalline forms (also known as polymorphs). In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. In some embodiments, the active entity is a phenolic compound as described herein. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, hydroxyl group(s) in the compounds disclosed herein is/are used to form a prodrug, wherein the hydroxyl group(s) is/are incorporated into an alkyl ester. In some embodiments the alkyl ester is an isopropyl ester or tert-butyl ester. In some embodiments the alkyl ester is an isopropyl ester.

Prodrug forms of the herein described compounds, wherein the prodrug is metabolized in vivo to produce a compound of Formula (I), (II), or (III), as set forth herein are included within the scope of the claims. In some cases, some of the herein-described compounds may be a prodrug for another derivative or active compound.

In some embodiments, sites on the aromatic ring portion of compounds described herein are susceptible to various metabolic reactions. Incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, deuterium or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms that are present in the compounds described herein is replaced with one or more deuterium atoms.

In additional or further embodiments, the compounds described herein are metabolized upon administration to an organism in need to produce a metabolite that is then used to produce a desired effect, including a desired therapeutic effect.

"Pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound described herein with acids. Pharmaceutically acceptable salts are also obtained by reacting a compound described herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid to form a salt such as, for example, a hydrochloric acid salt, a hydrobromic acid salt, a sulfuric acid salt, a phosphoric acid salt, a metaphosphoric acid salt, and the like; or with an organic acid to form a salt such as, for example, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a L-malic acid salt, a maleic acid salt, an oxalic acid salt, a fumaric acid salt, a trifluoroacetic acid salt, a tartaric acid salt, a L-tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, a valproic acid salt, and the like; (2) salts formed when an acidic proton present in the parent compound is replaced by a metal ion, e.g., an alkali metal ion (e.g. a lithium salt, a sodium salt, or a potassium salt), an alkaline earth ion (e.g. a magnesium salt, or a calcium salt), or an aluminum ion (e.g. an aluminum salt). In some cases, compounds described herein may coordinate with an organic base to form a salt, such as, but not limited to, an ethanolamine salt, a diethanolamine salt, a triethanolamine salt, a tromethamine salt, a N-methylglucamine salt, a dicyclohexylamine salt, or a tris(hydroxymethyl)methylamine salt. In other cases, compounds described herein may form salts with amino acids such as, but not limited to, an arginine salt, a lysine salt, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms.

CERTAIN TERMINOLOGY

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl moiety may be branched or straight chain. The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). Typical alkyl groups include, but are in no way limited to, methyl, ethyl, propyl, isopropyl, butyl, isobutyl, sec-butyl, tertiary butyl, pentyl, neopentyl, hexyl, and the like. In some embodiments, 1 or more hydrogen atoms of an alkyl are replaced with 1 or more deuterium atoms.

The term "halo" or, alternatively, "halogen" or "halide" means fluoro (F), chloro (Cl), bromo (Br) or iodo (I).

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The methods and formulations described herein include the use of N-oxides (if appropriate), crystalline forms (also known as polymorphs), or pharmaceutically acceptable salts of a compound having the structure of Formula (I), (II), or (III), as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

The term "enantiomeric ratio" refers to ratio of the percentage of one enantiomer in a mixture to that of the other. In some embodiments, compositions disclosed herein include a compound of Formula (III), or a pharmaceutically acceptable salt, solvate or prodrug thereof, with an enantiomeric ratio of at least 80%-(S):20%-(R), at least 85%-(S):15%-(R), at least 90%-(S):10%-(R), at least 95%-(S):5%-(R), at least 99%-(S):1%-(R), or greater than 99%-(S):1%-(R). In some embodiments, compositions described herein include enantiomerically pure compound of Formula (III), or a pharmaceutically acceptable salt, solvate or prodrug thereof. In some embodiments, compositions disclosed herein include a compound of Formula (II), or a pharmaceutically acceptable salt, solvate or prodrug thereof, with an enantiomeric ratio of at least 80%-(R):20%-(S), at least 85%-(R):15%-(S), at least 90%-(R):10%-(S), at least 95%-(R):5%-(S), at least 99%-(R):1%-(S), or greater than 99%-(R):1%-(S). In some embodiments, compositions described herein include enantiomerically pure compound of Formula (II), or a pharmaceutically acceptable salt, solvate or prodrug thereof.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

"Selective estrogen receptor modulator" or "SERM" as used herein, refers to a molecule that differentially modulates the activity of estrogen receptors in different tissues. For example, in some embodiments, a SERM displays ER antagonist activity in some tissues and ER agonist activity in other tissues. In some embodiments, a SERM displays ER antagonist activity in some tissues and minimal or no ER agonist activity in other tissues. In some embodiments, a SERM displays ER antagonist activity in breast tissues, ovarian tissues, endometrial tissues, and/or cervical tissues but minimal or no ER agonist activity in uterine tissues.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonist" as used herein, refers to a small-molecule agent that binds to a nuclear hormone receptor and subsequently decreases the basal level of nuclear hormone receptor transcriptional activity that is present in the absence of a known agonist.

The term "degrader" as used herein, refers to a small molecule agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90% or at least 95%. In some embodiments, a degrader as described herein lowers steady state estrogen receptor levels by at least 65%. In some embodiments, a degrader as described herein lowers steady state estrogen receptor levels by at least 85%.

The term "selective estrogen receptor degrader" or "SERD" as used herein, refers to a small molecule agent that preferentially binds to estrogen receptors versus other receptors and subsequently lowers the steady state estrogen receptor levels.

The term "ER-dependent", as used herein, refers to diseases or conditions that would not occur, or would not occur to the same extent, in the absence of estrogen receptors.

The term "ER-mediated", as used herein, refers to diseases or conditions that would not occur in the absence of estrogen receptors but can occur in the presence of estrogen receptors.

The term "ER-sensitive", as used herein, refers to diseases or conditions that would not occur, or would not occur to the same extent, in the absence of estrogens.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (II), or (III), or a pharmaceutically acceptable salt thereof, and a co-agent, are both administered to a patient simultaneously in the form of a single entity or dosage. The term "non-fixed combination" means that the active ingredients, e.g. a compound of Formula (I), (II), or (III), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), (II), or (III), or a pharmaceutically acceptable salt thereof, and at least one pharmaceutically acceptable inactive ingredient. In some embodiments, the compounds described herein are administered as pharmaceutical compositions in which a compound of Formula (I), (II), or (III), or a pharmaceutically acceptable salt thereof, is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (II), or (III), or a pharmaceutically acceptable salt thereof, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to a mammal.

A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), (II), or (III), or a pharmaceutically acceptable salt thereof, are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (II), or (III), as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

The pharmaceutical compositions described herein, which include a compound of Formula (I), (II), or (III), or a pharmaceutically acceptable salt thereof, are formulated into any suitable dosage form, including but not limited to, aqueous oral dispersions, liquids, gels, syrups, elixirs, slurries, suspensions, solid oral dosage forms, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In some embodiments, the push-fit capsules do not include any other ingredient besides the capsule shell and the active ingredient. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral soage forms are prepared by mixing a compound of Formula (I), (II), or (III), or a pharmaceutically acceptable salt thereof, with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulation is in the form of a capsule.

In some embodiments, solid dosage forms, e.g., tablets, effervescent tablets, and capsules, are prepared by mixing particles of a compound of Formula (I), (II), or (III), or a pharmaceutically acceptable salt thereof, with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

In some embodiments, tablets will include a film surrounding the final compressed tablet. In some embodiments, the film coating can provide a delayed release of the compound of Formula (I), (II), or (III), or a pharmaceutically acceptable salt thereof, from the formulation. In other embodiments, the film coating aids in patient compliance (e.g., Opadry® coatings or sugar coating). Film coatings including Opadry® typically range from about 1% to about 3% of the tablet weight.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound of Formula (I), (II), or (III), or a pharmaceutically acceptable salt thereof, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In still other embodiments, effervescent powders are also prepared. Effervescent salts have been used to disperse medicines in water for oral administration.

In some embodiments, the pharmaceutical solid oral dosage forms are formulated to provide a controlled release of the active compound. Controlled release refers to the release of the active compound from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of the active compound upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or in the art.

In some embodiments, pharmaceutical formulations are provided that include particles of a compound of Formula (I), (II), or (III), or a pharmaceutically acceptable salt thereof, and at least one dispersing agent or suspending agent for oral administration to a subject. The formulations may be a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formula (I), the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

Buccal formulations that include a compound of Formula (I), (II), or (III), or a pharmaceutically acceptable salt thereof, are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

In some embodiments, compounds of Formula (I), (II), or (III), or a pharmaceutically acceptable salt thereof, are prepared as transdermal dosage forms. In one embodiment, the transdermal formulations described herein include at least three components: (1) a formulation of a compound of Formula (I), (II), or (III), or a pharmaceutically acceptable salt thereof; (2) a penetration enhancer; and (3) an aqueous adjuvant. In some embodiments the transdermal formulations include additional components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of the active compound. In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of Formula (I), (II), or (III), or a pharmaceutically acceptable salt thereof, is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), vegetable oils and organic esters, such as ethyl oleate. In some embodiments, formulations suitable for subcutaneous injection contain additives such as preserving, wetting, emulsifying, and dispensing agents. Prolonged absorption of the injectable pharmaceutical form can be brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer.

For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

Methods of Dosing and Treatment Regimens

In one embodiment, the compounds of Formula (I), (II), or (III), or a pharmaceutically acceptable salt thereof, are used in the preparation of medicaments for the treatment of diseases or conditions in a mammal that would benefit from a reduction of estrogen receptor activity. Methods for treating any of the diseases or conditions described herein in a mammal in need of such treatment, involves administration of pharmaceutical compositions that include at least one compound of Formula (I), (II), or (III), or a pharmaceutically acceptable salt thereof, or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), (II), or (III), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In some embodiments, daily dosages appropriate for the compound of Formula (I), (II), or (III), or a pharmaceutically acceptable salt thereof, described herein are from about 1 mg per day to about 1000 mg per day. In some embodiments, daily dosages appropriate for the compound of Formula (I), (II), or (III), or a pharmaceutically acceptable salt thereof, described herein are from about 10 mg per day to about 1000 mg per day, from about 10 mg per day to about 900 mg per day, from about 10 mg per day to about 800 mg per day, from about 10 mg per day to about 700 mg per day, from about 10 mg per day to about 600 mg per day, from about 10 mg per day to about 500 mg per day, from about 10 mg per day to about 400 mg per day, from about 50 mg per day to about 500 mg per day, or from about 100 mg per day to about 400 mg per day. In some embodiments, daily dosages appropriate for the compound of Formula (I), (II), or (III), or a pharmaceutically acceptable salt thereof, described herein are from about 50 mg per day to about 300 mg per day. In some embodiments, daily dosages appropriate for the compound of Formula (I), (II), or (III), or a pharmaceutically acceptable salt thereof, described herein are from about 1 mg per day, 5 mg per day, 10 mg per day, 20 mg per day, 30 mg per day, 40 mg per day, 50 mg per day, 60 mg per day, 70 mg per day, 80 mg per day, 90 mg per day, 100 mg per day, 110 mg per day, 120 mg per day, 130 mg per day, 140 mg per day, 150 mg per day, 160 mg per day, 170 mg per day, 180 mg per day, 190 mg per day, 200 mg per day, 210 mg per day, 220 mg per day, 230 mg per day, 240 mg per day, 250 mg per day, 260 mg per day, 270 mg per day, 280 mg per day, 290 mg per day, 300 mg per day, 310 mg per day, 320 mg per day, 330 mg per day, 340 mg per day, 350 mg per day, 360 mg per day, 370 mg per day, 380 mg per day, 390 mg per day, 400 mg per day, 410 mg per day, 420 mg per day, 430 mg per day, 440 mg per day, 450 mg per day, 460 mg per day, 470 mg per day, 480 mg per day, 490 mg per day, 500 mg per day, 510 mg per day, 520 mg per day, 530 mg per day, 540 mg per day, 550 mg per day, 560 mg per day, 570 mg per day, 580 mg per day, 590 mg per day, 600 mg per day, 610 mg per day, 620 mg per day, 630 mg per day, 640 mg per day, 650 mg per day, 660 mg per day, 670 mg per day, 680 mg per day, 690 mg per day, 700 mg per day, 710 mg per day, 720 mg per day, 730 mg per day, 740 mg per day, 750 mg per day, 760 mg per day, 770 mg per day, 780 mg per day, 790 mg per day, 800 mg per day, 810 mg per day, 820 mg per day, 830 mg per day, 840 mg per day, 850 mg per day, 860 mg per day, 870 mg per day, 880 mg per day, 890 mg per day, 900 mg per day, 910 mg per day, 920 mg per day, 930 mg per day, 940 mg per day, 950 mg per day, 960 mg per day, 970 mg per day, 980 mg per day, 990 mg per day, or 1000 mg per day. In one embodiment, the desired dose is conveniently presented in a single dose or in divided doses administered simultaneously or at appropriate intervals, for example as two, three, four or more sub-doses per day.

In some embodiments, the daily dosages appropriate for the compound of Formula (I), (II), or (III), or a pharmaceutically acceptable salt thereof, described herein are administered once a day, twice a day, or three times a day. In some embodiments, the daily dosages appropriate for the compound of Formula (I), (II), or (III), or a pharmaceutically acceptable salt thereof, described herein are administered once a day. In some embodiments, the daily dosages appropriate for the compound of Formula (I), (II), or (III), or a pharmaceutically acceptable salt thereof, described herein are administered twice a day.

In one embodiment, the daily dosages appropriate for the compound of Formula (I), (II), or (III), or a pharmaceutically acceptable salt thereof, described herein are from about 0.01 to about 10 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In some embodiments, CA-125 blood levels are monitored in humans that are administered (or considered as candidates for treatment with) a compound of Formula (I), (II), or (III), or a pharmaceutically acceptable salt thereof. CA-125 (also known as mucin-16) is a glycoprotein in humans. In some embodiments, CA-125 levels are elevated in the blood of patients with certain type of cancers. In some embodiments, CA-125 is used as a serum biomarker in patients with certain type of cancers. In some embodiments, the certain types of cancers include, but are not limited to, breast cancer, ovarian cancer, endometrial (uterine) cancer, prostate cancer, and lung cancer. In some embodiments, monitoring CA-125 levels in the blood is used to determine the tumor burden in a human. In some embodiments, monitoring CA-125 levels in the blood is used to determine when to give a human anti-cancer therapy (e.g. a compound of Formula (I), (II), or (III), or a pharmaceutically acceptable salt thereof). In some embodiments, monitoring CA-125 levels in the blood is used to determine how a human is responding to anti-cancer therapy (e.g. a compound of Formula (I), (II), or (III), or a pharmaceutically acceptable salt thereof). In some embodiments, CA-125 is used as a biomarker for the diagnosis and management of ovarian cancer. Rising levels of CA-125 after radiation therapy or surgery with no detectable metastases could indicate recurrent ovarian cancer and the need to start anti-cancer treatment.

In certain embodiments, CA-125 levels are used to select patients with cancer for treatment with a compound of Formula (I), (II), or (III), or a pharmaceutically acceptable salt thereof. In some embodiments, a compound of Formula (I), (II), or (III), or a pharmaceutically acceptable salt thereof, is admistered to a human that is diagnosed with cancer, wherein the CA-125 levels in blood samples from the human are rising. In some embodiments, the cancer is breast cancer or ovarian cancer or endometrial cancer. In some embodiments, the cancer is ovarian cancer. In some embodiments, the human with ovarian cancer has previously undergone a hysterectomy and/or a bilateral salpingo-oophorectomy. In some embodiments, the ovarian cancer patient has previously been treated with chemotherapy. In some embodiments, the ovarian cancer is recurrent ovarian cancer. In some embodiments, the recurrent ovarian cancer is treated with endocrine therapy (e.g. a compound of Formula (I), (II), or (III), or a pharmaceutically acceptable salt thereof) before metastases develop and treatment with chemotherapy is required. In some embodiments, treatment with a compound of Formula (I), (II), or (III), or a pharmaceutically acceptable salt thereof delays the development of distant metastases.

In some embodiments, a compound of Formula (I), (II), or (III), or a pharmaceutically acceptable salt thereof, is administered to humans diagnosed with cancer and a CA-125 serum concentration doubling time of less than 10 days, less than 20 days, less than 30 days, less than 40 days, less than 50 days, less than 60 days, less than 70 days, less than 80 days, less than 90 days or less than 100 days. In some embodiments, CA-125 doubling time is less than 40 days. In some embodiments, the cancer is breast cancer, ovarian cancer, endometrial (uterine) cancer, prostate cancer, or lung cancer. In some embodiments, the cancer is ovarian cancer.

Combination Treatments

In certain instances, it is appropriate to administer at least one compound of Formula (I), (II), or (III), or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula (I), (II), or (III), or a pharmaceutically acceptable salt thereof, is co-administered with a second therapeutic agent, wherein the compound of Formula (I), (II), or (III), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), (II), or (III), or a pharmaceutically acceptable salt thereof, is initiated prior to, during, or after treatment with a second agent described herein, and continues until any time during treatment with the second agent or after termination of treatment with the second agent. It also includes treatments in which a compound of Formula (I), (II), or (III), or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compound of Formula (I), (II), or (III), or a pharmaceutically acceptable salt thereof, as well as combination therapies, is administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Exemplary Agents for Use in Combination Therapy

In some embodiments, methods for treatment of estrogen receptor-dependent or estrogen receptor-mediated conditions or diseases, such as proliferative disorders, including cancer, comprises administration to a mammal a compound of Formula (I), (II), or (III), or a pharmaceutically acceptable salt thereof, in combination with at least one additional therapeutic agent.

In some embodiments, a compound of Formula (I), (II), or (III), or a pharmaceutically acceptable salt thereof, is used in combination with one or more additional therapeutically active agents selected from: corticosteroids, anti-emetic agents, analgesics, anti-cancer agents, anti-inflammatories, kinase inhibitors, antibodies, HSP90 inhibitors, histone deacetylase (HDAC) inhibitors, modulators of the immune system, PD-1 inhibitors, poly ADP-ribose polymerase (PARP) inhibitors, and aromatase inhibitors.

In certain instances, it is appropriate to administer at least one compound of Formula (I), (II), or (III), or a pharmaceutically acceptable salt thereof, in combination with one or more other therapeutic agents. In certain embodiments, the one or more other therapeutic agents is an anti-cancer agent(s).

In some embodiments, a compound of Formula (I), (II), or (III), or a pharmaceutically acceptable salt thereof, is used in combination with an aromatase inhibitor, a phosphoinositide 3-kinase (PI3K)/mTOR pathway inhibitor, a CDK 4/6 inhibitor, a HER-2 inhibitor, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

In some embodiments, a compound of Formula (I), (II), or (III), or a pharmaceutically acceptable salt thereof, is used in combination with hormone blocking therapy, chemotherapy, radiation therapy, monoclonal antibodies, or combinations thereof.

Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182, 780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

Chemotherapy includes the use of anti-cancer agents.

Monoclonal antibodies include, but are not limited to, trastuzumab (Herceptin).

In some embodiments, a compound of Formula (I), (II), or (III), or a pharmaceutically acceptable salt thereof, is used in combination with at least one additional therapeutic agent selected from: abiraterone; abarelix; adriamycin; aactinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; AZD6244; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; bosutinib; brequinar sodium; bropirimine; busulfan; cab ozantinib; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dinaciclib; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; ENMD-2076; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; foretinib; fosquidone; fostriecin sodium; fulvestrant; gefitinib; gemcitabine; gemcitabine hydrochloride; gemcitabine-cisplatin; gemtuzumab ozogamicin; goserelin acetate; GSK1120212; histrelin acetate; hydroxyurea; idarubicin hydrochloride; ifosfamide; iimofosine; ibritumomab tiuxetan; idarubicin; ifosfamide; imatinib mesylate; imiquimod; interleukin II (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; MM-121; mycophenolic acid; nandrolone phenpropionate; nelarabine; nilotinib; nocodazoie; nofetumomab; nogalamycin; ofatumumab; onartuzumab; oprelvekin; ormaplatin; oxaliplatin; oxisuran; paclitaxel; palbociclib (PD-0332991); palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; saracatinib; sargramostim; seliciclib; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium;

TAK-733; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I 131 Iodine tositumomab; trastuzumab; trestolone acetate; tretinoin; triciribine phosphate; trimetrexate; trimetrexate glucuronate; triptorelin; tubulozole hydrochloride; U3-1287; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; or zorubicin hydrochloride.

In some embodiments, the at least one additional chemotherapeutic agent is selected from, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the compound of Formula (I), (II), or (III), or a pharmaceutically acceptable salt thereof, is administered or formulated in combination with one or more anticancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with the compounds of Formula (I), (II), or (III), or a pharmaceutically acceptable salt thereof, include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Further examples of anti-cancer agents for use in combination with the compounds of Formula (I), (II), or (III), or a pharmaceutically acceptable salt thereof, include aromatase inhibitors. Aromatase inhibitors include steroidal aromatase inhibitors and non-steroidal aromatase inhibitors. Steroidal aromatase inhibitors include, but are not limited to, exemestane. Non-steroidal aromatase inhibitors include, but are not limited to, anastrozole, and letrozole. In some embodiments, the aromatase inhibitor is anastrozole, letrozole or exemestane.

In some embodiments, a compound of Formula (I), (II), or (III), or a pharmaceutically acceptable salt thereof, is administered in combination with a CDK 4/6 inhibitor. In some embodiments, the CDK 4/6 inhibitor is palbociclib (PD-0332991), LEE011 or LY283519. In some embodiments, the CDK 4/6 inhibitor is LEE011. In some embodiments, LEE011 is administered at a dose of about 10 mg per day to about 1000 mg per day. In some embodiments, LEE011 is administered at a dose of about 400 mg per day, about 500 mg per day or about 600 mg per day. In some embodiments, the daily dose of LEE011 is orally administered. In some embodiments, the daily dose of LEE011 is orally administered once a day for three weeks followed by a one week drug holiday where LEE011 is not administered.

In some embodiments, a compound of Formula (I), (II), or (III), or a pharmaceutically acceptable salt thereof, is administered in combination with a phosphoinositide 3-kinase (PI3K)/mTOR pathway inhibitor. In some embodiments, the a phosphoinositide 3-kinase (PI3K)/mTOR pathway inhibitor is everolimus, temsirolimus, BEZ235, BYL719, GDC0032, BKM120, BGT226, GDC0068, GDC-0980, GDC0941, INK128 (MLN0128), INK1117, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Cal101, PWT33597, CU-906, AZD-2014 or CUDC-907. In some embodiments, the phosphoinositide 3-kinase (PI3K)/mTOR pathway inhibitor is everolimus. In some embodiments, everolimus is administered at a dose of about 1 mg per day to about 20 mg per day. In some embodiments, everolimus is administered at a dose of about 2.5 mg per day, about 5 mg per day, or about 10 mg per day. In some embodiments, the daily dose of everolimus is administered once a day. In some embodiments, the phosphoinositide 3-kinase (PI3K)/mTOR pathway inhibitor is BKM120. In some embodiments, BKM120 is administered at a dose of about 5 mg per day to about 500 mg per day. In some embodiments, BKM120 is administered at a dose of about 50 mg per day to about 100 mg per day. In some embodiments, BKM120 is administered at a dose of about 100 mg per day. In some embodiments, the daily dose of BKM120 is administered once a day. In some embodiments, the phosphoinositide 3-kinase (PI3K)/mTOR pathway inhibitor is BYL719. In some embodiments, BYL719 is administered at a dose of about 25 mg per day to about 1000 mg per day. In some embodiments, BYL719 is administered at a dose of about 250 mg per day or about 350 mg per day. In some embodiments, the daily dose of BYL719 is administered once a day.

In some embodiments, a compound of Formula (I), (II), or (III), or a pharmaceutically acceptable salt thereof, is administered in combination with a histone deacetylase inhibitor (HDAC). In some embodiments, the HDAC inhibitor is entinostat, vorinostat (SAHA), panobinostat or mocetinostat. In some embodiments, the HDAC inhibitor is entinostat. In some embodiments, entinostat is administered at a dose of about 0.1 mg per day to about 100 mg per day. In some embodiments, entinostat is administered at a dose of about 4 mg per day to about 15 mg per day. In some embodiments, entinostat is administered orally on days 1 and 15 of a 28 day cycle. In some embodiments, entinostat is administered orally weekly for 3 weeks followed by a 1-week break in a 4-week cycle. In some embodiments, entinostat is administered orally on days 3 and 10 of a 28 day cycle. In some embodiments, entinostat is administered once daily on days 1, 8, 15, 22, and 29. In some embodiments, 10 mg or 15 mg of entinostat is administered every other week or 15 mg on days 1, 8, and 15 every 28 days. In some embodiments, entinostat is orally administered on day 1 and day 8 at a dose of between 4 mg to 8 mg. In some embodiments, 5 mg of entinostat is orally administered once weekly.

In some embodiments, a compound of Formula (I), (II), or (III), or a pharmaceutically acceptable salt thereof, is administered in combination with a HER-2 inhibitor. In some embodiments, the HER-2 inhibitor is trastuzumab, pertuzumab or TDM-1.

In some embodiments, a compound of Formula (I), (II), or (III), or a pharmaceutically acceptable salt thereof, is administered in combination with an epidermal growth factor receptor (EGFR) inhibitor. In some embodiments, the EGFR inhibitor is lapatinib, gefitinib, erlotinib, cetuximab, canertinib, panitumumab, nimotuzumab, OSI-632, vandetanib, afatinib, MP-412, AEE-788, neratinib, XL-647, dacomitinib, AZD-8931, CUDC-101, AP-26113, MEHD7945A or CO-1686.

In some embodiments, a compound of Formula (I), (II), or (III), or a pharmaceutically acceptable salt thereof, is administered in combination with an anti-angiogenesis agent. In some embodiments, the anti-angiogenesis agent is a VEGFR inhibitor. In some embodiments, the anti-angiogenesis agent is a multi-kinase targeting agent. In some embodiments, the anti-angiogenesis agent is bevacizumab, ABR-215050 (tasquinimod), CHIR-258 (dovitinib), EXEL-7647, OSI-930, BIBF-1120, BAY-73-4506, BMS-582664 (brivanib), RO-4929097, JNJ-26483327, AZD-2171 (cediranib), sorafenib, aflibercept, enzastaurin, AG-013736 (axitinib), GSK-786034 (pazopanib), AP-23573, or sunitinib In some embodiments, a compound of Formula (I), (II), or (III), or a pharmaceutically acceptable salt thereof, is administered in combination with an anti-PD-1 agent. In some embodiments, the anti-PD-1 agent is MK-3475, Nivolumab, MPDL3280A, or MEDI4736.

In some embodiments, a compound of Formula (I), (II), or (III), or a pharmaceutically acceptable salt thereof, is administered in combination with an AKT inhibitor. In some embodiments, the AKT inhibitor is GDC0068, MK-2206, AT7867, GSK2110183, GSK2141795, AZD5363 or GSK690693.

In some embodiments, a compound of Formula (I), (II), or (III), or a pharmaceutically acceptable salt thereof, is administered in combination with an IGFR inhibitor. In some embodiments, the IGFR inhibitor is cixutumumab, dalotuzumab, BMS-754807, or MEDI-573

In some embodiments, a compound of Formula (I), (II), or (III), or a pharmaceutically acceptable salt thereof, is administered in combination with an FGFR inhibitor. In some embodiments, the FGFR inhibitor is CHIR-258 (dovitinib), E-3810, or AZD4547.

In some embodiments, a compound of Formula (I), (II), or (III), or a pharmaceutically acceptable salt thereof, is administered in combination with doxorubicin, cyclophosphamide, capecitabine, vinorelbine, paclitaxel, doxetaxel, or cisplatin.

Yet other anticancer agents for use in combination with the compounds of Formula (I), (II), or (III), or a pharmaceutically acceptable salt thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with the compounds of Formula (I), (II), or (III), or a pharmaceutically acceptable salt thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with the compounds of Formula (I), (II), or (III), or a pharmaceutically acceptable salt thereof, include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.).

In some embodiments, compounds of Formula (I), (II), or (III), or a pharmaceutically acceptable salt thereof, are used to treat cancer in combination with: a second antiestrogen (e.g., tamoxifen), an antiandrogen (e.g., bicalutamide, flutamide, enzalutamide), a gonadotropin releasing hormone analog (e.g., leuprolide).

Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, Isoeleutherobin A, and Z-Eleutherobin), Caribaeoside, Caribaeolin, Halichondrin B, Diazonamide A, Taccalonolide A, Diozostatin, (–)-Phenylahistin, Myoseverin B, Resverastatin phosphate sodium.

In one aspect, a compound of Formula (I), (II), or (III), or a pharmaceutically acceptable salt thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, a compound of Formula (I), (II), or (III), or a pharmaceutically acceptable salt thereof, is used in combination with anti-emetic agents to treat nausea or emesis, which may result from the use of a compound of Formula (I), (II), or (III), or a pharmaceutically acceptable salt thereof, anti-cancer agent(s) and/or radiation therapy.

Anti-emetic agents include, but are not limited to: neurokinin-1 receptor antagonists, 5HT3 receptor antagonists (such as ondansetron, granisetron, tropisetron, palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, a compound of Formula (I), (II), or (III), or a pharmaceutically acceptable salt thereof, is used in combination with an agent useful in the treatment of anemia. Such an anemia treatment agent is, for example, a continuous eythropoiesis receptor activator (such as epoetin-α).

In some embodiments, a compound of Formula (I), (II), or (III), or a pharmaceutically acceptable salt thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, a compound of Formula (I), (II), or (III), or a pharmaceutically acceptable salt thereof, is administered with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, a compound of Formula (I), (II), or (III), or a pharmaceutically acceptable salt thereof, is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745, 337 and NS398).

In some embodiments, a compound of Formula (I), (II), or (III), or a pharmaceutically acceptable salt thereof, is coadministered with an analgesic.

In some embodiments, a compound of Formula (I), (II), or (III), or a pharmaceutically acceptable salt thereof, is used in combination with radiation therapy (or radiotherapy). Radiation therapy is the treatment of cancer and other diseases with ionizing radiation. Radiation therapy can be used to treat localized solid tumors, such as cancers of the skin, tongue, larynx, brain, breast, prostate, colon, uterus and/or cervix. It can also be used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultraviolet light.

In some embodiments, a compound of Formula (I), (II), or (III), or a pharmaceutically acceptable salt thereof, is used in the treatment of breast cancer in combination with at least one additional treatment option for the breast cancer. In some embodiments, a compound of Formula (I), (II), or (III), or a pharmaceutically acceptable salt thereof, is used either alone or in combination with other agents used to treat breast cancer, including but not limited to aromatase inhibitors, anthracylines, platins, nitrogen mustard, alkylating agents, taxanes, nucleoside analogs, a phosphoinositide 3-kinase (PI3K)/mTOR pathway inhibitor, CDK 4/6 inhibitors, HER-2 inhibitors, EGFR inhibitors, PD-1 inhibitors, poly ADP-ribose polymerase (PARP) inhibitors, histone deacetylase (HDAC) inhibitors, and HSP90 inhibitors. Illustrative agents used to treat breast cancer, include, but are not limited to, fulvestrant, tamoxifen, anastrozole, letrozole, exemestane, GDC0032, goserelin, leuprolide, raloxifene, toremifene, megestrol acetate, bazedoxifene, cisplatin, carboplatin, capecitabine, cyclophosphamide, docetaxel, doxorubicin, epirubicin, eribulin, filgrastim, fluorouracil, gemcitabine, ixabepilone, LEE011, LY2835219, mitoxantrone, methotrexate, paclitaxel, pamidronate, vinorelbine, pegfilgrastim, pertuzumab, trastuzumab, lapatinib, everolimus, bevacizumab, temsirolimus and combinations thereof, as well as others described herein. Additional non-limiting exemplary agents for the treatment of breast cancer are provided elsewhere herein. In some embodiments, a compound of Formula (I), (II), or (III), or a pharmaceutically acceptable salt thereof, is used either alone or in combination with breast cancer surgery. In some embodiments, breast cancer surgery comprises lumpectomy, mastectomy, sentinel node biopsy, or axillary node dissection. In some embodiments, a compound of Formula (I), (II), or (III), or a pharmaceutically acceptable salt thereof, is used either alone or in combination with radiation therapy. In some embodiments, radiation comprises external beam radiation or brachytherapy. In some embodiments, a compound of Formula (I), (II), or (III), or a pharmaceutically acceptable salt thereof, is used either alone or in combination with hormone therapy (i.e. hormone blocking therapy). In some embodiments, hormone therapy comprises the use of a selective estrogen receptor modulator (e.g. tamoxifen), aromatase inhibitor, or fulvestrant. In some embodiments, a compound of Formula (I), (II), or (III), or a pharmaceutically acceptable salt thereof, is used either alone or in combination with surgery to remove the ovaries or medications to stop the ovaries from making estrogen. In some embodiments, a compound of Formula (I), (II), or (III), or a pharmaceutically acceptable salt thereof, is used either alone or in combination with trastuzumab, lapatinib, or bevacizumab. In some embodiments, a compound of Formula (I), (II), or (III), or a pharmaceutically acceptable salt thereof, is used either alone or in combination with bone-building drugs to prevent breast cancer recurrence (e.g. zoledronic acid (Reclast, Zometa)).

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein.

Intermediate 1

2-(3-(Fluoromethyl)azetidin-1-yl)ethanol

Step 1: tert-Butyl 3-(((methylsulfonyl)oxy)methyl)azetidine-1-carboxylate

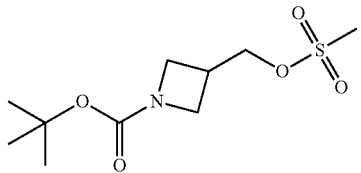 [SMILES: CC(C)(C)OC(=O)N1CC(COS(C)(=O)=O)C1]

Methanesulfonyl chloride (32 mL, 401 mmol) was added over 30 min to a solution of tert-butyl 3-(hydroxymethyl)azetidine-1-carboxylate (50 g, 267 mmol), triethylamine (74 mL, 534 mmol), and dichloromethane (500 mL) at 0° C. The resulting cloudy orange mixture was stirred at 0° C. for 1 h and then diluted with 10% aqueous citric acid (200 mL). The layers were separated, and the organic phase was washed with 10% aqueous citric acid (200 mL), sat'd sodium bicarbonate (200 mL×2), and then water (100 mL). The organic phase was dried over sodium sulfate, filtered, and concentrated to give tert-butyl 3-(((methylsulfonyl)oxy)methyl)azetidine-1-carboxylate as a dark orange oil. This material was used without further purification. $^1$H NMR (400 MHz, DMSO-$d_6$): δ 4.33 (d, 2H), 3.91 (m, 2H), 3.61 (m, 2H), 3.21 (s, 3H), 2.89 (m, 1H), 1.37 (s, 9H).

Step 2: tert-Butyl 3-(fluoromethyl)azetidine-1-carboxylate

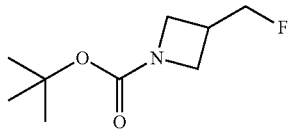

tert-Butyl 3-(((methylsulfonyl)oxy)methyl)azetidine-1-carboxylate (70 g, 267 mmol) was dissolved in a solution of TBAF (1M in THF, 500 mL, 500 mmol). The resulting orange solution was refluxed for 1 h and then cooled to rt. Half of the solvent was removed on a rotary evaporator. The resulting thick oil was diluted with ethyl acetate (300 mL) and then washed with brine (200 mL×2). The combined brine layers were extracted with ethyl acetate (200 mL). The organics were combined and washed with water (200 mL). This aqueous phase was extracted with ethyl acetate (150 mL×3). The organics were combined, dried over sodium sulfate, filtered, concentrated, and purified by silica gel chromatography (0-40% ethyl acetate/hexanes) to give 42 g of tert-butyl 3-(fluoromethyl)azetidine-1-carboxylate as a yellow oil. $^1$H NMR (400 MHz, DMSO-$d_6$): δ 4.52 (dd, 2H), 3.90 (m, 2H), 3.61 (m, 2H), 2.83 (m, 1H), 1.37 (s, 9H).

Step 3: 3-(Fluoromethyl)azetidine hydrochloride

Aqueous HCl (6M, 111 mL, 666 mmol) was added slowly to a solution of tert-butyl 3-(fluoromethyl)azetidine-1-carboxylate (42 g, 222 mmol) and methanol (450 mL) at 0° C. The reaction was stirred overnight (warming to rt as bath expired) and then concentrated. Residual water was azeotropically removed with methanol (400 mL×3) on a rotary evaporator until thick oil was obtained. This oil solidifies under high vacuum to give 27 g of 3-(fluoromethyl)azetidine hydrochloride as a hygroscopic white solid. ¹H NMR (400 MHz, DMSO-d₆) δ 9.18 (bs, 2H), 4.56 (dd, 2H), 3.98 (m, 2H), 3.75 (m, 2H), 3.11 (m, 1H).

Step 4: 2-(3-(Fluoromethyl)azetidin-1-yl)ethanol

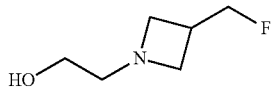

Aqueous NaOH (5M, 102 mL, 510 mmol) was added to a mixture of 3-(fluoromethyl)azetidine hydrochloride (20.0 g, 159 mmol) and THF (640 mL) at rt. After stirring for 10 min, 2-bromoethanol (12.4 mL, 175 mmol) was added dropwise. The resulting mixture was stirred overnight, and then the layers were separated. The organic layer was washed with sat'd aqueous K₂CO₃ (200 mL), dried over sodium sulfate, filtered, and concentrated to give a pale yellow oil. Distillation under reduced pressure (bp: 68-71° C. at 2 torr) gave 2-(3-(fluoromethyl)azetidin-1-yl)ethanol as a clear oil. ¹H NMR (DMSO-d₆): δ 4.49 (dd, 2H), 4.37 (br, 1H), 3.31 (t, 2H), 3.23 (t, 2H), 2.91 (t, 2H), 2.76-2.61 (m, 1H), 2.41 (t, 2H).

Note: 2-(3-(Fluoromethyl)azetidin-1-yl)ethanol can also be purified by silica gel chromatography [ethyl acetate/hexanes (10:7)→ethyl acetate/hexanes/methanol/triethylamine (10:7:2:1)].

Intermediate 2

2-(3-Methylazetidin-1-yl)ethanol

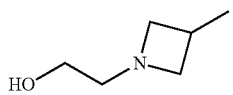

A mixture of 3-methylazetidine hydrochloride (2.5 g, 23.2 mmol), 2-bromoethanol (5.80 g, 46.4 mmol) and 1,8-diazabicyclo[5.4.0]undec-7-ene (10.61 g, 69.7 mmol) in anhydrous THF (46 mL) was stirred at room temperature for 40 hours. Resulting solids were filtered off and the filtrate was concentrated on a rotary evaporator to give a residue that was purified on a silica gel column eluted with hexanes:ethyl acetate:methanol:TEA=10:7:2:1 to afford pale yellow oil. 1H NMR (400 MHz, DMSO-d₆): δ 4.32 (br, 1H), 3.33-3.26 (m, 4H), 2.62 (t, 2H), 2.42-2.34 (m, 1H), 2.37 (t, 2H), 1.07 (d, 3H).

Example 1

2-(4-(2-(3-(Fluoromethyl)azetidin-1-yl)ethoxy)phenyl)-3-(4-fluorophenyl)-4-methyl-2H-chromen-6-ol

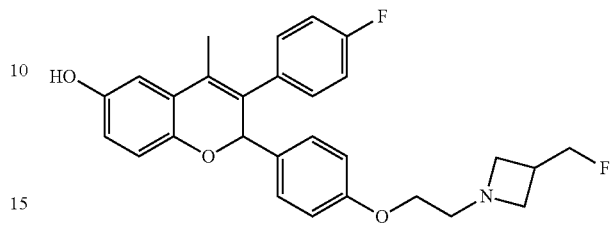

Step 1:
1-(2,5-Dimethoxyphenyl)-2-(4-fluorophenyl)ethanone

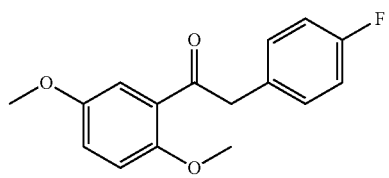 [SMILES: COc1ccc(OC)c(C(=O)Cc2ccc(F)cc2)c1]

Polyphosphoric acid (330 g) was heated at 75° C. for 4.5 h, and then 1,4-dimethoxybenzene (48.0 g, 347 mmol) and 4-fluorophenyl acetic acid (30.1 g, 195 mmol) were added. The reaction was mixed thoroughly with a spatula until homogenous, heated at 75° C. for 17 h, allowed to cool to 50° C., and then quenched by portion-wise addition of water (160 mL) while stirring with a spatula. The mixture was cooled to rt with an ice/water bath, diluted with ice water (160 mL), and then extracted with ethyl acetate (400 mL×1, 200 mL×2). The combined organic extracts were washed with brine (300 mL), dried (Mg₂SO₄), filtered, concentrated, and purified by silica gel chromatography (0-10% ethyl acetate in hexanes) to give 18.9 g of 1-(2,5-dimethoxyphenyl)-2-(4-fluorophenyl)ethanone as a pink solid. ¹H NMR (400 MHz, DMSO-d₆): δ 7.27-7.20 (m, 2H), 7.15-7.07 (m, 5H), 4.26 (s, 2H), 3.85 (s, 3H), 3.72 (s, 3H).

Step 2:
1-(2,5-Dihydroxyphenyl)-2-(4-fluorophenyl)ethanone

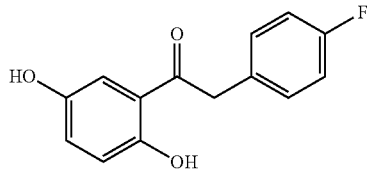 [SMILES: O=C(Cc1ccc(F)cc1)c1cc(O)ccc1O]

A solution of 1-(2,5-dimethoxyphenyl)-2-(4-fluorophenyl)ethanone (18.9 g, 68.9 mmol) and dichloromethane (275 mL) at −78° C. was degassed with three vacuum/N₂ cycles. Boron tribromide (20.0 mL, 208 mmol) was added dropwise over 40 min. The reaction was stirred at −78° C. for 20 min, stirred at 0° C. for 40 min, recooled to −78° C., and then quenched by dropwise addition of methanol (35 mL) over 55 min. The mixture was diluted with ice water (400 mL), ethyl acetate (150 mL), and then additional water (200 mL). The layers were partitioned, and the organic extract was washed with NaHCO₃ (400 mL), washed with brine (400 mL), dried (MgSO₄), filtered and concentrated. The crude material (17.1 g) was used without purification. ¹H NMR (400 MHz, DMSO-d₆): δ 11.12 (s, 1H), 9.22 (s, 1H), 7.33-7.26 (m, 3H), 7.19-7.11 (m, 2H), 7.03-6.93 (m, 1H), 6.82 (d, 1H), 4.23 (s, 2H).

Step 3: 2-(4-Fluorophenyl)-1-(2-hydroxy-5-((tetra-hydro-2H-pyran-2-yl)oxy)phenyl)ethanone

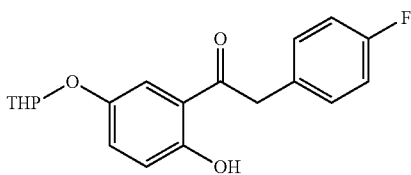

Pyridinium p-toluene sulfonate (3.50 g, 13.9 mmol) and 3,4-dihydro-2H-pyran (19.0 mL, 208 mmol) were added to a mixture of 1-(2,5-dihydroxyphenyl)-2-(4-fluorophenyl) ethanone (17.2 g, 69.6 mmol) and dichloromethane (345 mL). After stirring for 2.5 h, the solution was washed with NaHCO₃ (400 mL). The aqueous layer was back extracted with dichloromethane (100 mL). The organics were combined, dried (MgSO₄), filtered, concentrated, and purified by silica gel chromatography (0-10% EtOAc in hexanes) to give 18.8 g of 2-(4-fluorophenyl)-1-(2-hydroxy-5-((tetrahydro-2H-pyran-2-yl)oxy)phenyl)ethanone as a yellow/pink solid. ¹H NMR (400 MHz, DMSO-d₆): δ 11.31 (s, 1H), 7.58 (d, 1H), 7.33-7.27 (m, 2H), 7.25 (dd, 1H), 7.15 (t, 2H), 6.92 (d, 1H), 5.44-5.38 (m, 1H), 4.49-4.38 (m, 2H), 3.83-3.75 (m, 1H), 3.58-3.50 (m, 1H), 1.94-1.68 (m, 3H), 1.68-1.48 (m, 3H); LCMS: 329 (M–H)⁻.

Step 4: 3-(4-Fluorophenyl)-2-(4-iodophenyl)-6-((tetrahydro-2H-pyran-2-yl)oxy)chroman-4-one

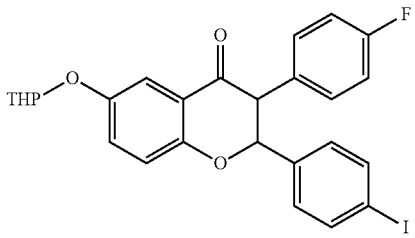

Piperidine (4.0 mL, 0.33 mmol) and 1,8-diazabicyclo[5.4.0]undec-7-ene (6.0 mL, 0.33 mmol) were added to a mixture of 2-(4-fluorophenyl)-1-(2-hydroxy-5-((tetrahydro-2H-pyran-2-yl)oxy)phenyl)ethanone (40.5 g, 123 mmol), 4-iodobenzaldehyde (28.5 g, 123 mmol), and s-butanol (130 mL). The reaction was heated at 135° C., and solvent (~42 mL) was removed via Dean-Stark trap over 2 h [Note: product started to precipitate after removing ~30 mL of solvent]. The reaction was allowed to cool to 80° C., i-propanol (130 mL) was added, and then the reaction was allowed to cool to rt. After stirring for 3 days, the precipitate was collected by filtration to give 63.8 g of 3-(4-fluorophe-nyl)-2-(4-iodophenyl)-6-((tetrahydro-2H-pyran-2-yl)oxy) chroman-4-one as a white solid. ¹H NMR (400 MHz, DMSO-d₆): δ 7.64 (d, 2H), 7.44-7.40 (m, 1H), 7.36-7.29 (m, 1H), 7.21-7.10 (m, 4H), 7.07 (d, 1H), 7.02 (t, 2H), 5.89 (dd, 1H), 5.50-5.43 (m, 1H), 4.71 (d, 1H), 3.79-3.70 (m, 1H), 3.59-3.50 (m, 1H), 1.93-1.69 (m, 3H), 1.69-1.48 (m, 3H); LCMS: 545 (M+H)⁺.

Step 5: 3-(4-Fluorophenyl)-2-(4-iodophenyl)-4-methyl-2H-chromen-6-ol

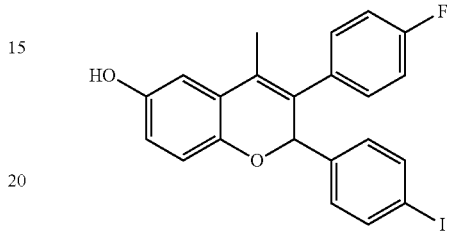

Methylmagnesium chloride (3M in THF, 120 mL, 360 mmol) was added dropwise over 2 h to a mixture of 3-(4-fluorophenyl)-2-(4-iodophenyl)-6-((tetrahydro-2H-pyran-2-yl)oxy)chroman-4-one (63.8 g, 117 mmol) and THF (330 mL) at 0° C. The reaction was stirred at 0° C. for 40 min and then allowed to warm to rt. After stirring for an additional 1.75 h, the reaction was cooled to 0° C., quenched by dropwise addition of sat'd ammonium chloride (100 mL), and then diluted with ethyl acetate (600 mL) and water (700 mL). The layers were separated, and the organic layer was washed with brine (500 mL), washed with water (500 mL), washed again with the first brine wash, dried (MgSO₄), filtered, concentrated, and then dried under high vacuum. The crude material was triturated with dichloromethane to give a white solid. A solution of this solid in acetic acid/water (4:1; 400 mL) was heated at 100° C. for 4 d, cooled to rt, concentrated, and then diluted with ethyl acetate (400 mL). This solution was washed with NaHCO₃ (300 mL×2), water (200 mL) and then brine (200 mL), dried (MgSO₄), filtered, concentrated and then purified by silica gel chromatography (0-15% EtOAc in hexanes) to give 41.1 g of 3-(4-fluorophenyl)-2-(4-iodophenyl)-4-methyl-2H-chromen-6-ol as a pink solid. ¹H NMR (400 MHz, DMSO-d₆): δ 9.02 (s, 1H), 7.60 (d, 2H), 7.37-7.31 (m, 2H), 7.18 (t, 2H), 7.08 (d, 2H), 6.76 (s, 1H), 6.55-6.50 (m, 2H), 5.98 (s, 1H), 2.01 (s, 3H); LCMS: 459 (M+H)⁺.

Step 6: 3-(4-Fluorophenyl)-2-(4-iodophenyl)-4-methyl-6-((tetrahydro-2H-pyran-2-yl)oxy)-2H-chromene

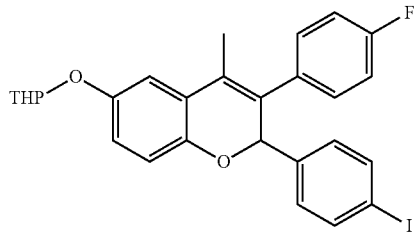

Pyridinium p-toluene sulfonate (4.50 g, 17.9 mmol) and 3,4-dihydro-2H-pyran (16.0 mL, 175 mmol) were added to a mixture of 1-(2,5-dihydroxyphenyl)-2-(4-fluorophenyl)ethanone (41.1 g, 89.7 mmol) and dichloromethane (400 mL). After stirring for 2.5 h, the reaction was diluted with dichloromethane (200 mL), washed with NaHCO$_3$ (300 mL), washed with brine (300 mL), dried (MgSO$_4$), filtered, concentrated, and purified by silica gel chromatography (0-6% EtOAc in hexanes) to give 37.1 g of 3-(4-fluorophenyl)-2-(4-iodophenyl)-4-methyl-6-((tetrahydro-2H-pyran-2-yl)oxy)-2H-chromene as a pink foam.

$^1$H NMR (400 MHz, DMSO-d$_6$): δ 7.62 (d, 2H), 7.39-7.32 (m, 2H), 7.19 (t, 2H), 7.09 (dd, 2H), 7.02-6.98 (m, 1H), 6.82 (dd, 1H), 6.64 (dd, 1H), 6.06 (s, 1H), 5.36 (s, 1H), 3.84-3.76 (m, 1H), 3.59-3.50 (m, 1H), 2.04 (s, 3H), 1.92-1.65 (m, 3H), 1.65-1.45 (m, 3H); LCMS: 543 (M+H)$^+$.

Step 7: 3-(Fluoromethyl)-1-(2-(4-(3-(4-fluorophenyl)-4-methyl-6-((tetrahydro-2H-pyran-2-yl)oxy)-2H-chromen-2-yl)phenoxy)ethyl)azetidine

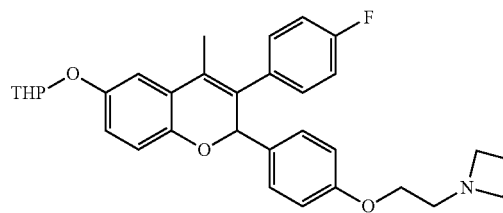

A mixture of 3-(4-fluorophenyl)-2-(4-iodophenyl)-4-methyl-6-((tetrahydro-2H-pyran-2-yl)oxy)-2H-chromene (22.1 g, 40.8 mmol), Intermediate 1 (8.23 g, 61.8 mmol), CuI (1.56 g, 8.19 mmol), K$_2$CO$_3$ (11.3 g, 81.6 mmol), and butyronitrile (82 mL) was degassed with three vacuum/N$_2$ cycles, heated at reflux for 22 h, and then allowed to cool to rt. Additional CuI (775 mg, 4.07 mmol) was added. The reaction was degassed with three vacuum/N$_2$ cycles, heated at reflux for 15 h, allowed to cool to rt, diluted with ethyl acetate (300 mL), and then filtered through Celite with additional ethyl acetate (500 mL). The filtrate was washed with water (250 mL×3), washed with brine (250 mL), dried (MgSO$_4$), filtered, concentrated, and purified by silica gel chromatography (40-100% EtOAc in hexanes) to give 17.9 g of 3-(fluoromethyl)-1-(2-(4-(3-(4-fluorophenyl)-4-methyl-6-((tetrahydro-2H-pyran-2-yl)oxy)-2H-chromen-2-yl)phenoxy)ethyl)azetidine as an orange foam. $^1$H NMR (400 MHz, DMSO-d$_6$): δ 7.37-7.30 (m, 2H), 7.22-7.14 (m, 4H), 7.02-6.98 (m, 1H), 6.82-6.74 (m, 3H), 6.60 (dd, 1H), 5.98 (s, 1H), 5.37-5.33 (m, 1H), 4.47 (dd, 2H), 3.86-3.75 (m, 3H), 3.58-3.50 (m, 1H), 3.27 (t, 2H), 2.95 (t, 2H), 2.75-2.61 (m, 3H), 2.04 (s, 3H), 1.92-1.66 (m, 3H), 1.66-1.48 (m, 3H); LCMS: 548 (M+H)$^+$.

Step 8: 2-(4-(2-(3-(Fluoromethyl)azetidin-1-yl)ethoxy)phenyl)-3-(4-fluorophenyl)-4-methyl-2H-chromen-6-ol

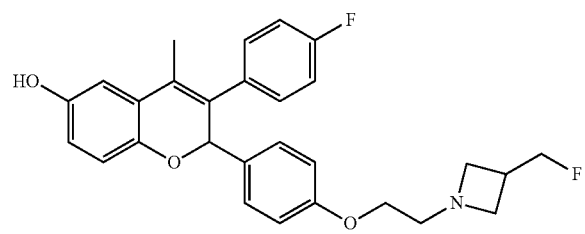 [SMILES: CC1=C(c2ccc(F)cc2)C(c2ccc(OCCN3CC(CF)C3)cc2)Oc2ccc(O)cc21]

A solution of 3-(fluoromethyl)-1-(2-(4-(3-(4-fluorophenyl)-4-methyl-6-((tetrahydro-2H-pyran-2-yl)oxy)-2H-chromen-2-yl)phenoxy)ethyl)azetidine (12.7 g, 23.1 mmol) in acetic acid/water (4:1, 230 mL) was stirred at rt for 15 h, concentrated, and then diluted with ethyl acetate (300 mL). This solution was washed with NaHCO$_3$ (150 mL×3), washed with brine (150 mL), dried (MgSO$_4$), filtered, concentrated, and purified by silica gel chromatography (0-7% CH$_3$OH in dichloromethane) to give 6.9 g of 2-(4-(2-(3-(fluoromethyl)azetidin-1-yl)ethoxy)phenyl)-3-(4-fluorophenyl)-4-methyl-2H-chromen-6-ol as a tan foam. $^1$H NMR (400 MHz, DMSO-d$_6$): δ 8.96 (s, 1H), 7.35-7.29 (m, 2H), 7.20-7.14 (m, 4H), 6.77-6.73 (m, 3H), 6.51-6.46 (m, 2H), 5.91 (s, 1H), 4.47 (dd, 2H), 3.81 (t, 2H), 3.27 (t, 2H), 2.95 (t, 2H), 2.74-2.62 (m, 3H), 2.01 (s, 3H); LCMS: 464 (M+H)$^+$.

Example 2

(R)-2-(4-(2-(3-(Fluoromethyl)azetidin-1-yl)ethoxy)phenyl)-3-(4-fluorophenyl)-4-methyl-2H-chromen-6-ol The title compound was the 1$^{st}$ eluting enantiomer when Example 1 was separated on a RegisCell column [CO$_2$/methanol+0.5% diethylamine (80/20)]. $^1$H NMR (400 MHz, DMSO-d$_6$): δ 8.97 (s, 1H), 7.35-7.28 (m, 2H), 7.21-7.14 (m, 4H), 6.78-6.73 (m, 3H), 6.52-6.46 (m, 2H), 5.91 (s, 1H), 4.47 (dd, 2H), 3.81 (t, 2H), 3.27 (t, 2H), 2.95 (t, 2H), 2.74-2.61 (m, 3H), 2.01 (s, 3H); LCMS: 464 (M+H)$^+$; Enantiomeric ratio: 99:1.

Example 3

(S)-2-(4-(2-(3-(Fluoromethyl)azetidin-1-yl)ethoxy)phenyl)-3-(4-fluorophenyl)-4-methyl-2H-chromen-6-ol The title compound was the 2$^{nd}$ eluting enantiomer when Example 1 was separated on a RegisCell column [CO$_2$/methanol+0.5% diethylamine (80/20)]. $^1$H NMR (400 MHz, DMSO-d$_6$): δ 8.96 (s, 1H), 7.35-7.28 (m, 2H), 7.21-7.13 (m, 4H), 6.78-6.73 (m, 3H), 6.52-6.46 (m, 2H), 5.91 (s, 1H), 4.47 (dd, 2H), 3.81 (t, 2H), 3.27 (t, 2H), 2.95 (t, 2H), 2.75-2.62 (m, 3H), 2.01 (s, 3H); LCMS: 464 (M+H)$^+$; Enantiomeric ratio: 99:1.

Example 4

3-(4-Chlorophenyl)-2-(4-(2-(3-(fluoromethyl)azetidin-1-yl)ethoxy)phenyl)-4-methyl-2H-chromen-6-ol

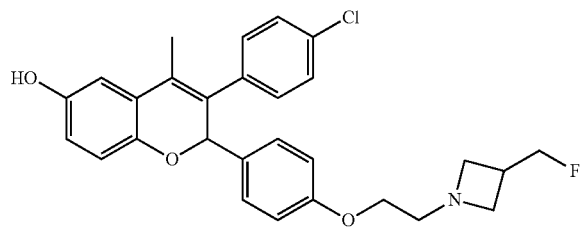 [SMILES: CC1=C(c2ccc(Cl)cc2)C(c2ccc(OCCN3CC(CF)C3)cc2)Oc2ccc(O)cc21]

The title compound was prepared from 4-chlorophenylacetic acid following the procedures outlined for Example 1. $^1$H NMR (400 MHz, DMSO-$d_6$): δ 8.97 (s, 1H), 7.39 (d, 2H), 7.30 (d, 2H), 7.17 (d, 2H), 6.75 (m, 3H), 6.5 (m, 2H), 5.91 (s, 1H), 4.46 (dd, 2H), 3.81 (t, 2H), 3.27 (t, 2H), 2.95 (t, 2H), 2.68 (m, 1H), 2.66 (t, 2H), 2.01 (s, 3H); LCMS: 480 (M+H)$^+$.

Example 5

(R)-3-(4-Chlorophenyl)-2-(4-(2-(3-(fluoromethyl)azetidin-1-yl)ethoxy)phenyl)-4-methyl-2H-chromen-6-ol

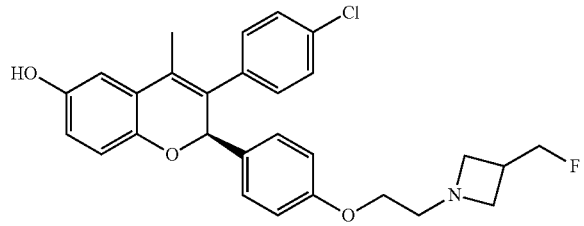

Separation of the enantiomers from the racemic mixture of Example 4 provides the title compound. Suitable separation techniques include chiral chromatography (e.g. Regis-Cell column [CO$_2$/methanol w/ diethylamine] or CHIRAL-PAK IA column [hexane/ethanol/tetrahydrofuran w/ diethylamine]).

Example 6

(S)-3-(4-Chlorophenyl)-2-(4-(2-(3-(fluoromethyl)azetidin-1-yl)ethoxy)phenyl)-4-methyl-2H-chromen-6-ol

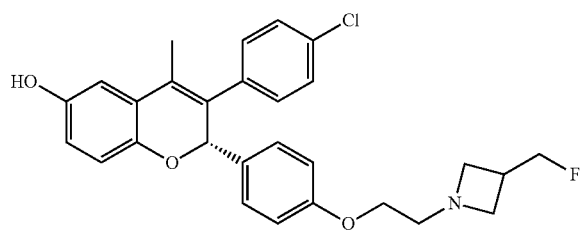 [SMILES: CC1=C(c2ccc(Cl)cc2)[C@H](c2ccc(OCCN3CC(CF)C3)cc2)Oc2ccc(O)cc21]

Separation of the enantiomers from the racemic mixture of Example 4 provides the title compound. Suitable separation techniques include chiral chromatography (e.g. Regis-Cell column [CO$_2$/methanol w/ diethylamine] or CHIRAL-PAK IA column [hexane/ethanol/tetrahydrofuran w/ diethylamine]).

Example 7

4-(2-(4-(2-(3-(Fluoromethyl)azetidin-1-yl)ethoxy)phenyl)-6-hydroxy-4-methyl-2H-chromen-3-yl)benzonitrile

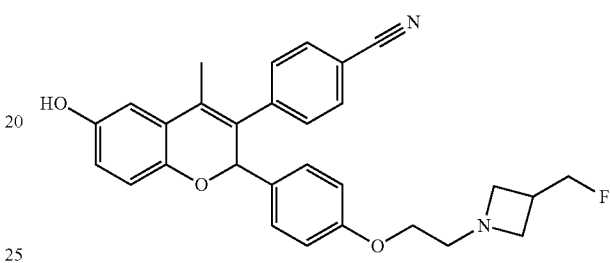

Step 1: 4-(2-(4-(2-(3-(Fluoromethyl)azetidin-1-yl)ethoxy)phenyl)-4-methyl-6-((tetrahydro-2H-pyran-2-yl)oxy)-2H-chromen-3-yl)benzonitrile

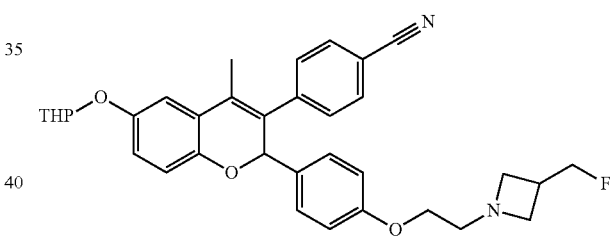

A mixture of 1-(2-(4-(3-(4-chlorophenyl)-4-methyl-6-((tetrahydro-2H-pyran-2-yl)oxy)-2H-chromen-2-yl)phenoxy)ethyl)-3-(fluoromethyl)azetidine (240 mg, 0.43 mmol, Intermediate of Example 4), racemic-2-di-t-butylphosphino-1,1'-binaphthyl (170 mg, 0.43 mmol), zinc powder (20 mg, 0.31 mmol), zinc cyanide (105 mg, 0.89 mmol), and DMA (2.9 mL) was degassed with three vacuum/N$_2$ cycles, and then palladium (II) acetate (141 mg, 0.43 mmol) was added. The reaction was degassed with three additional vacuum/N$_2$ cycles, heated at 95° C. overnight, allowed to cool to rt, and then diluted with ethyl acetate. This mixture was washed with water (×2), washed with brine, dried (Na$_2$SO$_4$), filtered, concentrated, and purified by silica gel chromatography (0-100% EtOAc in hexanes) to give 158 mg of 4-(2-(4-(2-(3-(fluoromethyl)azetidin-1-yl)ethoxy)phenyl)-4-methyl-6-((tetrahydro-2H-pyran-2-yl)oxy)-2H-chromen-3-yl)benzonitrile as a yellow solid. $^1$H NMR (400 MHz, DMSO-$d_6$): δ 7.81 (d, 2H), 7.52-7.48 (m, 2H), 7.20-7.17 (m, 2H), 7.03-7.02 (m, 1H), 6.83-6.75 (m, 3H), 6.62 (dd, 1H), 6.05 (s, 1H), 5.35 (s, 1H), 4.47 (dd, 2H), 3.82-3.77 (m, 3H), 3.55-3.51 (m, 1H), 3.25 (t, 2H), 2.93 (m, 2H), 2.69-2.63 (m, 3H), 2.05 (s, 3H), 1.95-1.66 (m, 3H), 1.65-1.47 (m, 3H); LCMS: 555 (M+H)$^+$.

Step 2: 4-(2-(4-(2-(3-(Fluoromethyl)azetidin-1-yl)ethoxy)phenyl)-6-hydroxy-4-methyl-2H-chromen-3-yl)benzonitrile

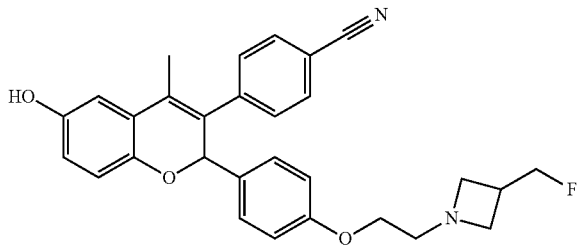 [SMILES: CC1=C(c2ccc(C#N)cc2)C(c2ccc(OCCN3CC(CF)C3)cc2)Oc2ccc(O)cc21]

The title compound was prepared from 4-(2-(4-(2-(3-(fluoromethyl)azetidin-1-yl)ethoxy)phenyl)-4-methyl-6-((tetrahydro-2H-pyran-2-yl)oxy)-2H-chromen-3-yl)benzonitrile following the procedure from Example 1, Step 8. $^1$H NMR (400 MHz, DMSO-$d_6$): δ 9.01 (s, 1H), 7.81 (d, 2H), 7.49 (d, 2H), 7.18 (d, 2H), 6.77-6.74 (m, 3H), 6.54-6.49 (m, 2H), 5.98 (s, 1H), 4.47 (dd, 2H), 3.81 (t, 2H), 3.27 (t, 2H), 2.96 (t, 2H), 2.74-2.66 (m, 3H), 2.03 (s, 3H); LCMS: 471 (M+H)$^+$.

Example 8

(R)-4-(2-(4-(2-(3-(Fluoromethyl)azetidin-1-yl)ethoxy)phenyl)-6-hydroxy-4-methyl-2H-chromen-3-yl)benzonitrile

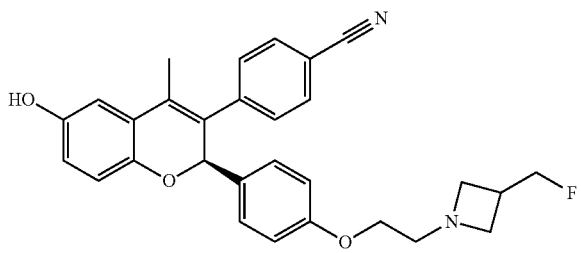

Separation of the enantiomers from the racemic mixture of Example 7 provides the title compound. Suitable separation techniques include chiral chromatography (e.g. Regis-Cell column [CO$_2$/methanol w/ diethylamine] or CHIRAL-PAK IA column [hexane/ethanol/tetrahydrofuran w/ diethylamine]).

Example 9

(S)-4-(2-(4-(2-(3-(Fluoromethyl)azetidin-1-yl)ethoxy)phenyl)-6-hydroxy-4-methyl-2H-chromen-3-yl)benzonitrile

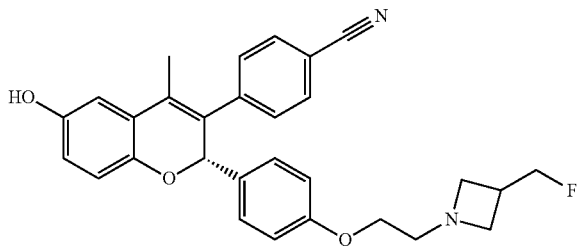 [SMILES: CC1=C(c2ccc(C#N)cc2)C(c2ccc(OCCN3CC(CF)C3)cc2)Oc2ccc(O)cc21]

Separation of the enantiomers from the racemic mixture of Example 7 provides the title compound. Suitable separation techniques include chiral chromatography (e.g. Regis-Cell column [CO$_2$/methanol w/ diethylamine] or CHIRAL-PAK IA column [hexane/ethanol/tetrahydrofuran w/ diethylamine]).

Example 10

3-(3,4-Difluorophenyl)-2-(4-(2-(3-(fluoromethyl)azetidin-1-yl)ethoxy)phenyl)-4-methyl-2H-chromen-6-ol

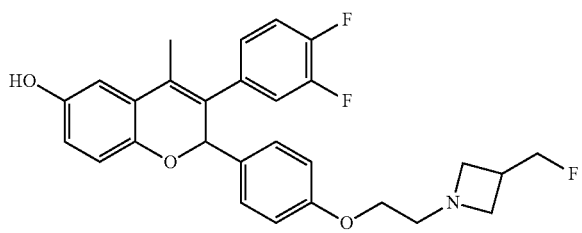

The title compound was prepared from 3,4-difluorophenylacetic acid following the procedures outlined for Example 1. $^1$H NMR (400 MHz, DMSO-$d_6$): δ 8.98 (s, 1H), 7.46-7.36 (m, 2H), 7.18 (d, 2H), 7.15-7.10 (m, 1H), 6.78-6.73 (m, 3H), 6.54-6.47 (m, 2H), 5.95 (s, 1H), 4.47 (dd, 2H), 3.82 (t, 2H), 3.27 (t, 2H), 2.95 (t, 2H), 2.76-2.62 (m, 3H), 2.03 (s, 3H); LCMS: 482 (M+H)$^+$.

Example 11

(R)-3-(3,4-Difluorophenyl)-2-(4-(2-(3-(fluoromethyl)azetidin-1-yl)ethoxy)phenyl)-4-methyl-2H-chromen-6-ol

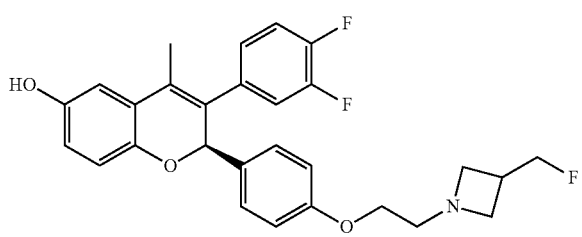

Separation of the enantiomers from the racemic mixture of Example 10 provides the title compound. Suitable separation techniques include chiral chromatography (e.g. Regis-Cell column [CO$_2$/methanol w/ diethylamine] or CHIRAL-PAK IA column [hexane/ethanol/tetrahydrofuran w/ diethylamine]).

Example 12

(S)-3-(3,4-Difluorophenyl)-2-(4-(2-(3-(fluoromethyl)azetidin-1-yl)ethoxy)phenyl)-4-methyl-2H-chromen-6-ol

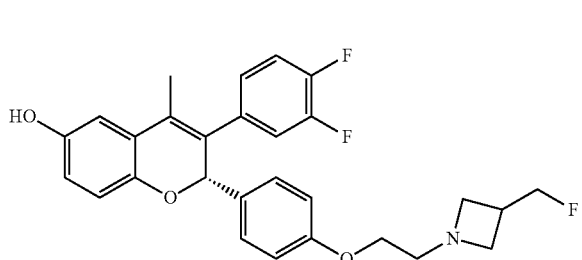

Separation of the enantiomers from the racemic mixture of Example 10 provides the title compound. Suitable separation techniques include chiral chromatography (e.g. Regis-Cell column [CO₂/methanol w/ diethylamine] or CHIRALPAK IA column [hexane/ethanol/tetrahydrofuran w/ diethylamine]).

Example 13

3-(3-Chloro-4-fluorophenyl)-2-(4-(2-(3-(fluoromethyl)azetidin-1-yl)ethoxy)phenyl)-4-methyl-2H-chromen-6-ol

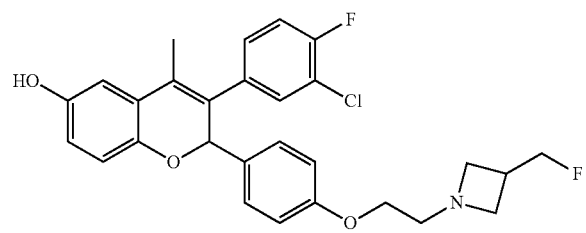 [SMILES: CC1=C(c2ccc(F)c(F)c2)C(c2ccc(OCCN3CC(CF)C3)cc2)Oc2ccc(O)cc21]

Step 1: 2-(3-Chloro-4-fluorophenyl)-1-(2,5-dimethoxyphenyl)ethanone

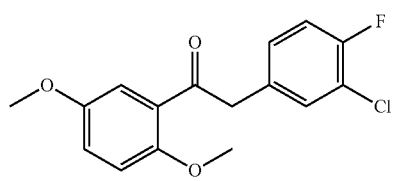

2,5-Dimethoxyacetophenone (8.1 g, 45.1 mmol) and 1-bromo-3-chloro-4-fluorobenzene (9.4 g, 45.1 mmol) were added to a mixture of tris(dibenzylideneacetone)dipalladium (0) (620 mg, 0.68 mmol), 2,2'-bis(diphenylphosphino)-1,1'-binaphthalene (1012 mg, 1.63 mmol), sodium tert-butoxide (5.9 g, 61.7 mmol), and THF (110 mL). After degassing with three vacuum/N₂ cycles, the mixture was stirred at 70° C. overnight, allowed to cool to rt, diluted with water, and extracted with ether (×2). The combined organic extracts were washed with brine, dried (Na₂SO₄), filtered, concentrated, and purified by silica gel chromatography (0-15% EtOAc in hexanes) to give 4.7 g of 2-(3-chloro-4-fluorophenyl)-1-(2,5-dimethoxyphenyl)ethanone as a pale yellow solid. $^1$H NMR (400 MHz, DMSO-$d_6$): δ 7.44 (dd, 1H), 7.36-7.31 (m, 1H), 7.23-7.19 (m, 1H), 7.14-7.11 (m, 3H), 4.29 (s, 2H), 3.86 (s, 3H), 3.72 (s, 3H).

Step 2: 3-(3-Chloro-4-fluorophenyl)-2-(4-(2-(3-(fluoromethyl)azetidin-1-yl)ethoxy)phenyl)-4-methyl-2H-chromen-6-ol

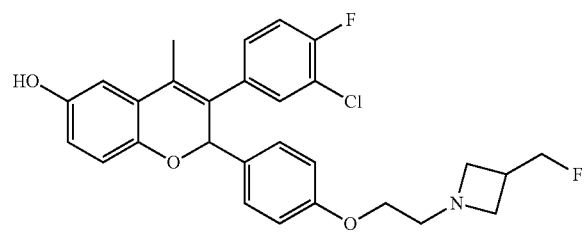

The title compound was prepared from 2-(3-chloro-4-fluorophenyl)-1-(2,5-dimethoxyphenyl)ethanone following the procedures outlined for Example 1, Steps 2-8. $^1$H NMR (400 MHz, DMSO-$d_6$): δ 8.98 (s, 1H), 7.52 (dd, 1H), 7.38 (t, 1H), 7.30-7.26 (m, 1H), 7.18 (d, 2H), 6.76-6.74 (m, 3H), 6.52-6.47 (m, 2H), 5.94 (s, 1H), 4.47 (dd, 2H), 3.81 (t, 2H), 3.26 (t, 2H), 2.94 (t, 2H), 2.71-2.63 (m, 3H), 2.01 (s, 3H); LCMS: 498 (M+H)⁺.

Example 14

(R)-3-(3-Chloro-4-fluorophenyl)-2-(4-(2-(3-(fluoromethyl)azetidin-1-yl)ethoxy)phenyl)-4-methyl-2H-chromen-6-ol

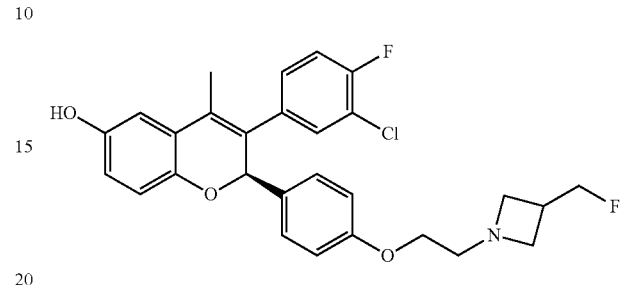

Separation of the enantiomers from the racemic mixture of Example 13 provides the title compound. Suitable separation techniques include chiral chromatography (e.g. Regis-Cell column [CO₂/methanol w/ diethylamine] or CHIRALPAK IA column [hexane/ethanol/tetrahydrofuran w/ diethylamine]).

Example 15

(S)-3-(3-Chloro-4-fluorophenyl)-2-(4-(2-(3-(fluoromethyl)azetidin-1-yl)ethoxy)phenyl)-4-methyl-2H-chromen-6-ol

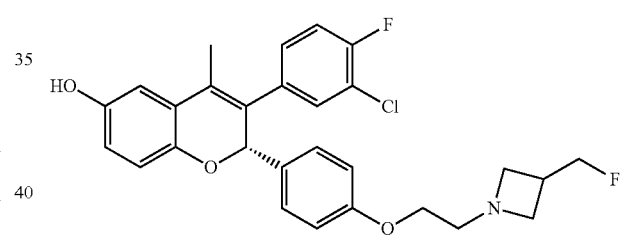

Separation of the enantiomers from the racemic mixture of Example 13 provides the title compound. Suitable separation techniques include chiral chromatography (e.g. Regis-Cell column [CO₂/methanol w/ diethylamine] or CHIRALPAK IA column [hexane/ethanol/tetrahydrofuran w/ diethylamine]).

Example 16

3-(4-Chloro-3-fluorophenyl)-2-(4-(2-(3-(fluoromethyl)azetidin-1-yl)ethoxy)phenyl)-4-methyl-2H-chromen-6-ol

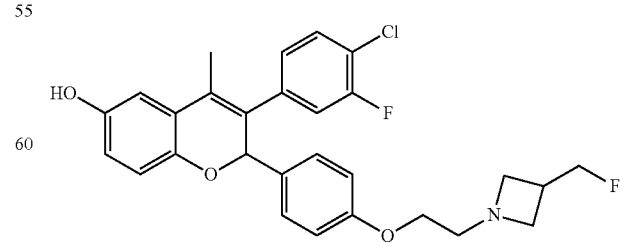

The title compound was prepared from 4-bromo-1-chloro-2-fluorobenzene following the procedures outlined for Example 13. $^1$H NMR (400 MHz, DMSO-$d_6$): δ 8.99 (s, 1H), 7.54 (t, 1H), 7.41 (dd, 1H), 7.19-7.13 (m, 3H), 6.76-6.74 (m, 3H), 6.53-6.48 (m, 2H), 5.96 (s, 1H), 4.47 (dd, 2H), 3.82 (t, 2H), 3.29-3.28 (m, 2H), 2.98 (m, 2H), 2.73-2.67 (m, 3H), 2.04 (s, 3H); LCMS: 498 (M+H)+.

Example 17

(R)-3-(4-Chloro-3-fluorophenyl)-2-(4-(2-(3-(fluoromethyl)azetidin-1-yl)ethoxy)phenyl)-4-methyl-2H-chromen-6-ol

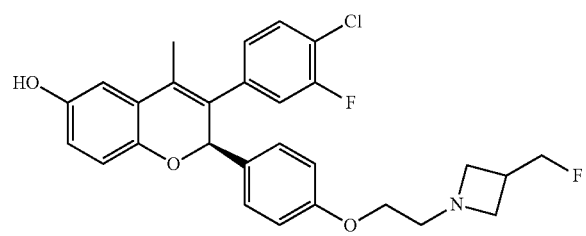 [SMILES: CC1=C(c2ccc(F)c(F)c2)[C@@H](c2ccc(OCCN3CC(CF)C3)cc2)Oc2ccc(O)cc21]

Separation of the enantiomers from the racemic mixture of Example 16 provides the title compound. Suitable separation techniques include chiral chromatography (e.g. Regis-Cell column [CO$_2$/methanol w/ diethylamine] or CHIRAL-PAK IA column [hexane/ethanol/tetrahydrofuran w/ diethylamine]).

Example 18

(S)-3-(4-Chloro-3-fluorophenyl)-2-(4-(2-(3-(fluoromethyl)azetidin-1-yl)ethoxy)phenyl)-4-methyl-2H-chromen-6-ol

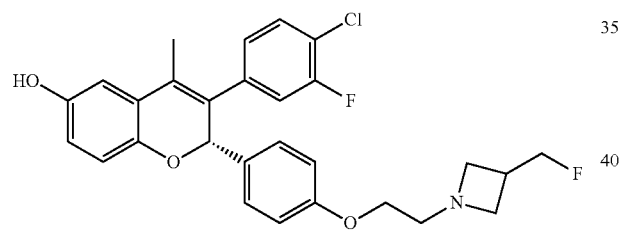

Separation of the enantiomers from the racemic mixture of Example 16 provides the title compound. Suitable separation techniques include chiral chromatography (e.g. Regis-Cell column [CO$_2$/methanol w/ diethylamine] or CHIRAL-PAK IA column [hexane/ethanol/tetrahydrofuran w/ diethylamine]).

Example 19

2-(4-(2-(3-(Fluoromethyl)azetidin-1-yl)ethoxy)phenyl)-4-methyl-3-(3,4,5-trifluorophenyl)-2H-chromen-6-ol

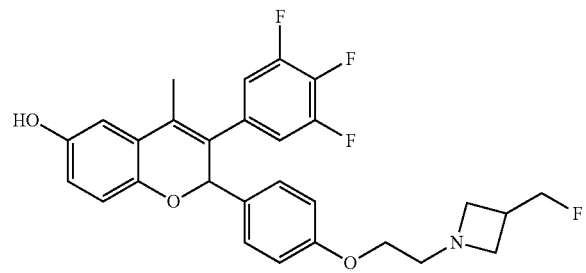 [SMILES: CC1=C(c2cc(F)c(F)c(F)c2)C(c2ccc(OCCN3CC(CF)C3)cc2)Oc2ccc(O)cc21]

The title compound was prepared from 5-bromo-1,2,3-trifluorobenzene following the procedures outlined for Example 13. $^1$H NMR (400 MHz, DMSO-d$_6$): δ 9.01 (s, 1H), 7.39-7.30 (m, 2H), 7.19 (d, 2H), 6.79-6.73 (m, 3H), 6.55-6.48 (m, 2H), 5.99 (s, 1H), 4.47 (dd, 2H), 3.82 (t, 2H), 3.27 (t, 2H), 2.95 (t, 2H), 2.74-2.62 (m, 3H), 2.05 (s, 3H); LCMS: 500 (M+H)+.

Example 20

(R)-2-(4-(2-(3-(Fluoromethyl)azetidin-1-yl)ethoxy)phenyl)-4-methyl-3-(3,4,5-trifluorophenyl)-2H-chromen-6-ol

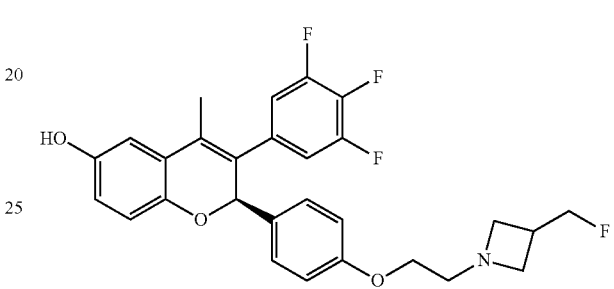

Separation of the enantiomers from the racemic mixture of Example 19 provides the title compound. Suitable separation techniques include chiral chromatography (e.g. Regis-Cell column [CO$_2$/methanol w/ diethylamine] or CHIRAL-PAK IA column [hexane/ethanol/tetrahydrofuran w/ diethylamine]).

Example 21

(S)-2-(4-(2-(3-(Fluoromethyl)azetidin-1-yl)ethoxy)phenyl)-4-methyl-3-(3,4,5-trifluorophenyl)-2H-chromen-6-ol

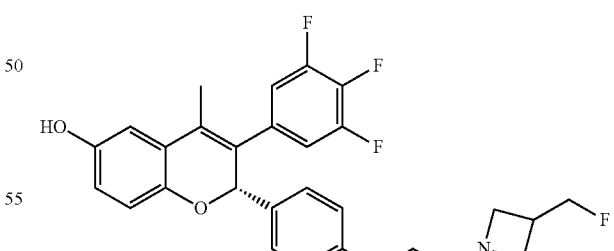

Separation of the enantiomers from the racemic mixture of Example 19 provides the title compound. Suitable separation techniques include chiral chromatography (e.g. Regis-Cell column [CO$_2$/methanol w/ diethylamine] or CHIRAL-PAK IA column [hexane/ethanol/tetrahydrofuran w/ diethylamine]).

Example 22

2-(4-(2-(3-(Fluoromethyl)azetidin-1-yl)ethoxy)phenyl)-4-methyl-3-(4-(trifluoromethyl)phenyl)-2H-chromen-6-ol

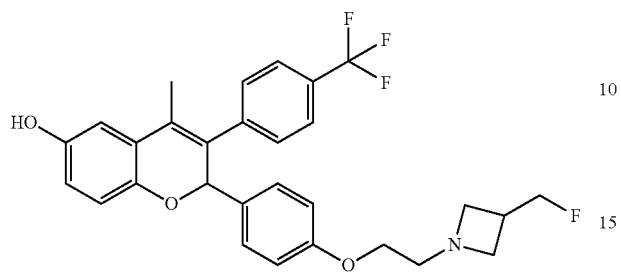

The title compound was prepared from 1-bromo-4-(trifluoromethyl)benzene following the procedures outlined for Example 13. $^1$H NMR (400 MHz, DMSO-d$_6$): δ 9.01 (s, 1H), 7.71 (d, 2H), 7.52 (d, 2H), 7.20 (d, 2H), 6.80-6.74 (m, 3H), 6.56-6.49 (m, 2H), 5.98 (s, 1H), 4.47 (dd, 2H), 3.81 (t, 2H), 3.26 (t, 2H), 2.95 (t, 2H), 2.75-2.62 (m, 3H), 2.04 (s, 3H); LCMS: 514 (M+H)$^+$.

Example 23

(R)-2-(4-(2-(3-(Fluoromethyl)azetidin-1-yl)ethoxy)phenyl)-4-methyl-3-(4-(trifluoromethyl)phenyl)-2H-chromen-6-ol

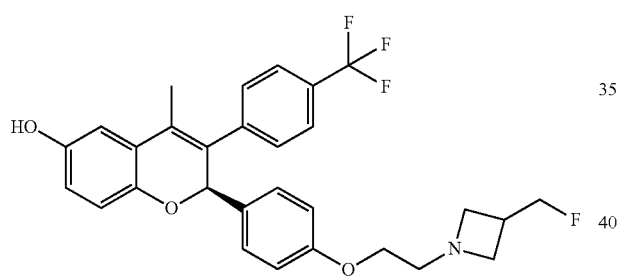

Separation of the enantiomers from the racemic mixture of Example 22 provides the title compound. Suitable separation techniques include chiral chromatography (e.g. Regis-Cell column [CO$_2$/methanol w/ diethylamine] or CHIRALPAK IA column [hexane/ethanol/tetrahydrofuran w/ diethylamine]).

Example 24

(S)-2-(4-(2-(3-(Fluoromethyl)azetidin-1-yl)ethoxy)phenyl)-4-methyl-3-(4-(trifluoromethyl)phenyl)-2H-chromen-6-ol

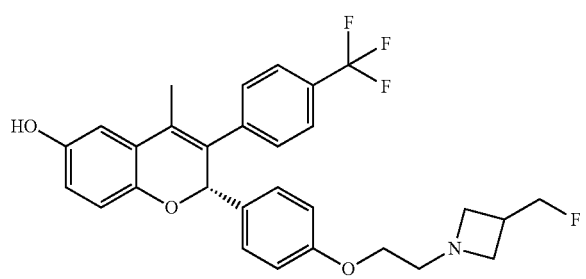 [SMILES: CC1=C(c2ccc(C(F)(F)F)cc2)[C@H](c2ccc(OCCN3CC(CF)C3)cc2)Oc2ccc(O)cc21]

Separation of the enantiomers from the racemic mixture of Example 22 provides the title compound. Suitable separation techniques include chiral chromatography (e.g. Regis-Cell column [CO$_2$/methanol w/ diethylamine] or CHIRALPAK IA column [hexane/ethanol/tetrahydrofuran w/ diethylamine]).

Example 25

2-(4-(2-(3-(Fluoromethyl)azetidin-1-yl)ethoxy)phenyl)-3-(4-fluorophenyl)-4-methyl-2H-chromen-7-ol

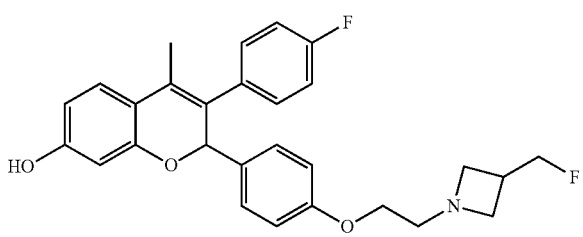 [SMILES: CC1=C(c2ccc(F)cc2)C(c2ccc(OCCN3CC(CF)C3)cc2)Oc2cc(O)ccc21]

Step 1:
1-(2,4-Dihydroxyphenyl)-2-(4-fluorophenyl)ethanone

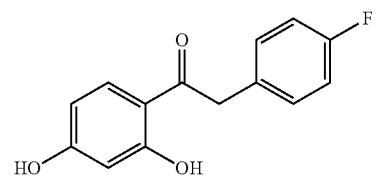 [SMILES: O=C(Cc1ccc(F)cc1)c1ccc(O)cc1O]

Anhydrous resorcinol (110 g, 1.0 mol) and (4-fluorophenyl)acetic acid (130.0 g, 0.9 mol) in BF$_3$.Et$_2$O (355 mL, 3.0 mol) were stirred under reflux for 1.5 h under N$_2$. The reaction vessel was then cooled in an ice bath and the reaction mixture poured into excess ice-water. The resulting mixture was extracted with ethyl acetate (3×300 mL). The combined organic phase was washed with water, saturated NaHCO$_3$, dried over Na$_2$SO$_4$ and filtered. Filtrate was concentrated to give the title compound (230 g, crude, yield 100%). $^1$H-NMR (DMSO-d$_6$, 400 MHz): δ 12.45 (s, 1H), 10.66 (s, 1H), 7.94 (d, 1H), 7.32 (m, 2H), 7.14 (t, 2H), 6.40 (dd, 1H), 6.27 (d, 1H), 4.08 (d, 2H).

Step 2: 2-(4-Fluorophenyl)-1-(2-hydroxy-4-((tetrahydro-2H-pyran-2-yl)oxy)phenyl)ethanone

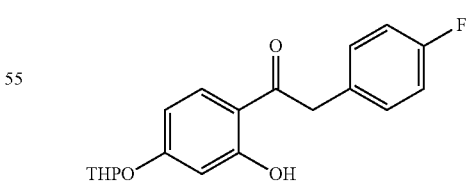

3,4-Dihydro-2H-pyran (265 g, 3.15 mol) was added into a solution of 1-(2,4-dihydroxyphenyl)-2-(4-fluorophenyl)ethanone (230 g, 0.9 mol) in DCM (500 mL) followed by slow addition of PPTS (37.7 g, 0.151 mol) at 5-8° C. over 30 min. The resulting mixture was stirred at room temperature for 24 h. The reaction mixture was concentrated on a rotary evaporator and the residue was purified by column chromatography (PE/EA=20/1) to afford the title compound as white solid (110 g, yield 37%). $^1$H-NMR (DMSO-$d_6$, 400 MHz): δ 12.30 (s, 1H), 8.02 (d, 1H), 7.32 (dd, 2H), 7.14 (t, 2H), 6.62 (dd, 1H), 6.56 (d, 1H), 5.62 (d, 1H), 4.37 (s, 2H), 3.75-3.58 (m, 2H), 1.90-1.49 (m, 6H).

Step 3: 3-(4-Fluorophenyl)-2-(4-iodophenyl)-7-((tetrahydro-2H-pyran-2-yl)oxy)chroman-4-one

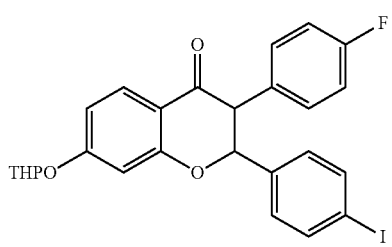

To a solution of 2-(4-fluorophenyl)-1-(2-hydroxy-4-((tetrahydro-2H-pyran-2-yl)oxy)phenyl)ethanone (64 g, 0.194 mol) in n-BuOH (600 mL) were added 1,8-diazabicyclo[5.4.0]undec-7-ene (8.96 g, 0.06 mol), 4-iodobenzaldehyde (49.5 g, 0.21 mol) and piperidine (5.2 g, 0.06 mol). The mixture was heated at 120° C. for 7 h and then cooled to room temperature. The reaction mixture was stirred at room temperature for 72 h to afford a precipitate. The precipitate was filtered to give the title compound as white solid (64.0 g, yield 60.7%). $^1$H-NMR (DMSO-$d_6$, 400 MHz): δ 7.77 (d, 1H), 7.64 (d, 2H), 7.19 (d, 2H), 7.16-7.09 (m, 2H), 7.02 (t, 2H), 6.78 (dt, 1H), 6.69 (d, 1H), 5.95-5.87 (m, 1H), 5.65-5.60 (m, 1H), 4.65 (d, 1H), 3.74-3.55 (m, 2H), 1.92-1.48 (m, 6H).

Step 4: 3-(4-Fluorophenyl)-2-(4-iodophenyl)-4-methyl-7-((tetrahydro-2H-pyran-2-yl)oxy)chroman-4-ol

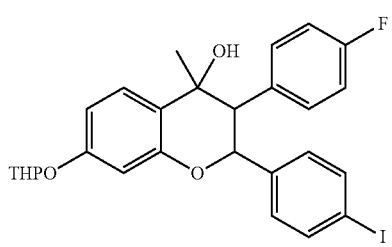

A solution of methylmagnesium chloride (3 M in THF, 154 mL, 460 mmol) was added into a solution of 3-(4-fluorophenyl)-2-(4-iodophenyl)-7-((tetrahydro-2H-pyran-2-yl)oxy)chroman-4-one (72 g, 132 mmol) in anhydrous THF (600 mL) at 0° C. under N$_2$ while keeping the internal temperature around 0° C. (Exothermic reaction). The mixture was stirred at 0° C. for 30 minutes and then at room temperature for 4 h. Reaction mixture was cooled to 0° C. and saturated NH$_4$Cl (200 mL) was added over 30 min. The mixture was extracted with ethyl acetate (3×300 mL). The combined organic layers were dried over Na$_2$SO$_4$ and concentrated in vacuo. The residue was purified by column chromatography (PE/EA=10/1) to afford the title compound as yellow solid (58 g, yield 78.2%).

Step 5: 3-(4-Fluorophenyl)-2-(4-iodophenyl)-4-methyl-2H-chromen-7-ol

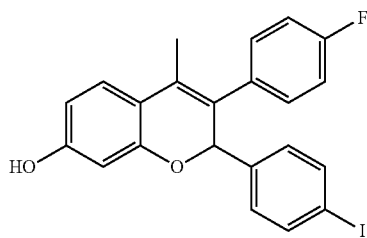 [SMILES: CC1=C(c2ccc(F)cc2)C(c2ccc(I)cc2)Oc2cc(O)ccc21]

To a suspension of 3-(4-fluorophenyl)-2-(4-iodophenyl)-4-methyl-7-((tetrahydro-2H-pyran-2-yl)oxy)chroman-4-ol (26 g, 46 mmol) in H$_2$O (50 mL) was added AcOH (200 mL) in one portion and the reaction mixture was stirred at room temperature for 60 h. The reaction mixture was poured into ice-water and extracted with ethyl acetate (3×250 mL). The combined organic layers were washed with saturated aqueous NaHCO$_3$ (3×100 mL), brine (200 mL), dried over Na$_2$SO$_4$ and concentrated in vacuo. The residue was purified by column chromatography (PE/EA=15/1) to afford the title compound as orange solid (15.5 g, yield 72.8%). $^1$H-NMR (DMSO-$d_6$, 400 MHz): δ 9.56 (s, 1H), 7.62 (d, 2H), 7.32-7.27 (m, 2H), 7.19-7.14 (m, 3H), 7.08 (d, 2H), 6.36 (dd, 1H), 6.12 (d, 1H), 6.01 (s, 1H), 1.24 (s, 3H).

Step 6: 3-(4-Fluorophenyl)-2-(4-iodophenyl)-4-methyl-7-((tetrahydro-2H-pyran-2-yl)oxy)-2H-chromene

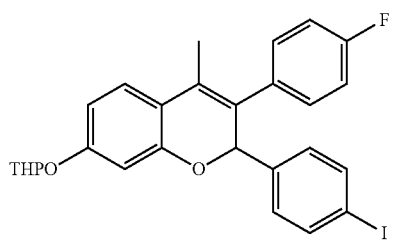

To a suspension of 3-(4-fluorophenyl)-2-(4-iodophenyl)-4-methyl-2H-chromen-7-ol (15.5 g, 34 mmol) in DCM (180 mL) was added neat 3,4-dihydro-2H-pyran (8.5 g, 101 mmol), followed by slow addition of PPTS (2.54 g, 10 mmol) at 5~8° C. over 10 min in an ice-bath. The resulting mixture was stirred at room temperature for 12 h. Then, the mixture was concentrated in vacuo and the residue was purified by column chromatography (PE/EA=40/1) to afford the title compound as white solid (10.8 g, yield 59%). $^1$H-NMR (DMSO-$d_6$, 400 MHz): δ 7.55 (dd, 2H), 7.19 (d, 1H), 7.12-7.07 (m, 2H), 7.04-6.96 (m, 4H), 6.67-6.61 (m, 1H), 6.50 (dd, 1H), 5.81 (m, 1H), 5.38-5.33 (m, 1H), 3.93-3.83 (m, 1H), 3.62-3.55 (m, 1H), 2.03 (s, 3H), 2.00-1.57 (m, 6H)

Step 7: 3-(Fluoromethyl)-1-(2-(4-(3-(4-fluorophenyl)-4-methyl-7-((tetrahydro-2H-pyran-2-yl)oxy)-2H-chromen-2-yl)phenoxy)ethyl)azetidine

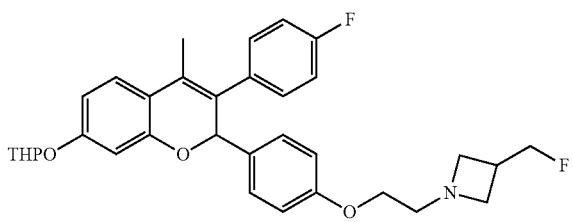

A mixture of 3-(4-fluorophenyl)-2-(4-iodophenyl)-4-methyl-7-((tetrahydro-2H-pyran-2-yl)oxy)-2H-chromene (550 mg, 1.01 mmol), 2-(3-(fluoromethyl)azetidin-1-yl)ethanol (266 mg, 2.00 mmol; Intermediate 1), CuI (40 mg, 0.21 mmol), $K_2CO_3$ (300 mg, 2.17 mmol), and butyronitrile (2 mL) was degassed with three vacuum/$N_2$ cycles and then heated at 130° C. for 65 h. After cooling, the reaction mixture was concentrated directly onto silica gel and purified by silica gel chromatography (1:0→0:1; hexanes:ethyl acetate containing 4% triethylamine) to give 508 mg of 3-(fluoromethyl)-1-(2-(4-(3-(4-fluorophenyl)-4-methyl-7-((tetrahydro-2H-pyran-2-yl)oxy)-2H-chromen-2-yl)phenoxy)ethyl)azetidine: $^1$H NMR (400 MHz, DMSO-$d_6$): δ 7.32-7.24 (m, 3H), 7.21 (d, 2H), 7.16 (app t, 2H), 6.77 (d, 2H), 6.59 (app dt, 1H), 6.34 (app dd, 1H), 6.00 (s, 1H), 5.42-5.34 (m, 1H), 4.47 (dd, 2H), 3.82 (t, 2H), 3.75-3.65 (m, 1H), 3.56-3.47 (m, 1H), 3.27 (t, 2H), 2.95 (t, 2H), 2.76-2.62 (m, 1H), 2.64 (t, 2H), 2.03 (s, 3H), 1.88-1.69 (m, 2H), 1.69-1.42 (m, 4H); LCMS: 548.1 [M+H]$^+$.

Step 8: 2-(4-(2-(3-(Fluoromethyl)azetidin-1-yl)ethoxy)phenyl)-3-(4-fluorophenyl)-4-methyl-2H-chromen-7-ol

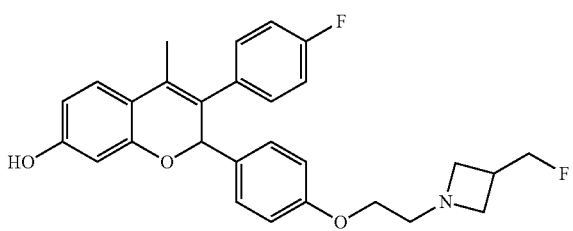

The title compound was prepared from 3-(fluoromethyl)-1-(2-(4-(3-(4-fluorophenyl)-4-methyl-7-((tetrahydro-2H-pyran-2-yl)oxy)-2H-chromen-2-yl)phenoxy)ethyl)azetidine following the procedure outlined for Example 1, Step 8 except reverse-phase HPLC was used for purification. $^1$H NMR (400 MHz, DMSO-$d_6$): δ 9.51 (s, 1H), 7.30-7.25 (m, 2H), 7.19 (d, 2H), 7.18-7.12 (m, 3H), 6.77 (d, 2H), 6.34 (dd, 1H), 6.08 (d, 1H), 5.93 (s, 1H), 4.47 (dd, 2H), 3.82 (t, 2H), 3.28 (t, 2H), 2.96 (t, 2H), 2.76-2.62 (m, 1H), 2.67 (t, 2H), 2.00 (s, 3H); LCMS: 464.1 [M+H]$^+$.

Example 26

(S)-2-(4-(2-(3-(Fluoromethyl)azetidin-1-yl)ethoxy)phenyl)-3-(4-fluorophenyl)-4-methyl-2H-chromen-7-ol

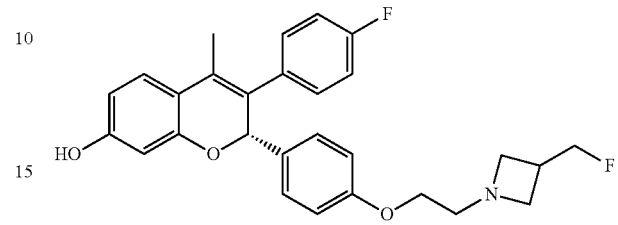

Separation of the enantiomers from the racemic mixture of Example 25 provides the title compound. Suitable separation techniques include chiral chromatography (e.g. Regis-Cell column [$CO_2$/methanol w/ diethylamine] or CHIRALPAK IA column [hexane/ethanol/tetrahydrofuran w/ diethylamine]).

Example 27

(R)-2-(4-(2-(3-(Fluoromethyl)azetidin-1-yl)ethoxy)phenyl)-3-(4-fluorophenyl)-4-methyl-2H-chromen-7-ol

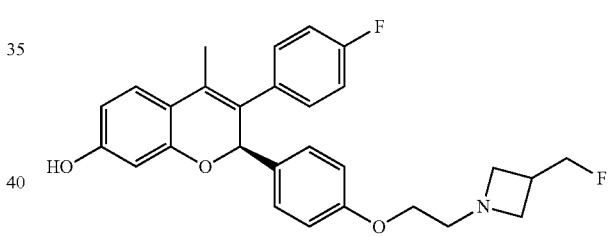

Separation of the enantiomers from the racemic mixture of Example 25 provides the title compound. Suitable separation techniques include chiral chromatography (e.g. Regis-Cell column [$CO_2$/methanol w/ diethylamine] or CHIRALPAK IA column [hexane/ethanol/tetrahydrofuran w/ diethylamine]).

Example 28

3-(4-Chlorophenyl)-2-(4-(2-(3-(fluoromethyl)azetidin-1-yl)ethoxy)phenyl)-4-methyl-2H-chromen-7-ol

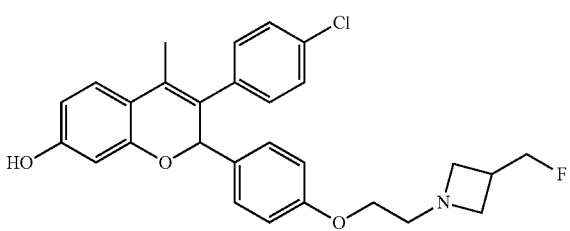 [SMILES: CC1=C(c2ccc(F)cc2)C(c2ccc(OCCN3CC(CF)C3)cc2)Oc2cc(O)ccc21]

The title compound was prepared from resorcinol and 4-chlorophenyl acetic acid following the procedures outlined for Example 25. ¹H NMR (400 MHz, DMSO-d₆): δ 9.53 (s, 1H), 7.37 (m, 2H), 7.27 (m, 2H), 7.19-7.14 (m, 3H), 6.77 (m, 2H), 6.34 (dd, 1H), 6.08 (d, 1H), 5.95 (s, 1H), 4.47 (dd, 2H), 3.82 (t, 2H), 3.27 (t, 2H), 2.95 (t, 2H), 2.77-2.64 (m, 3H), 2.01 (s, 3H); LCMS: 480.0 [M+H]⁺.

Example 29

(S)-3-(4-Chlorophenyl)-2-(4-(2-(3-(fluoromethyl)azetidin-1-yl)ethoxy)phenyl)-4-methyl-2H-chromen-7-ol

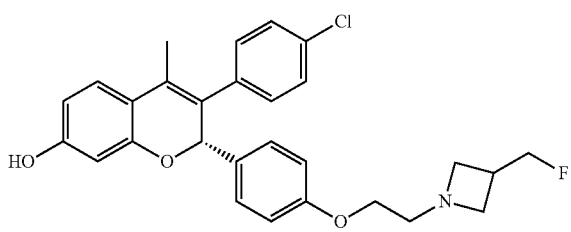 [SMILES: CC1=C(c2ccc(Cl)cc2)[C@H](c2ccc(OCCN3CC(CF)C3)cc2)Oc2cc(O)ccc21]

Separation of the enantiomers from the racemic mixture of Example 28 provides the title compound. Suitable separation techniques include chiral chromatography (e.g. Regis-Cell column [CO₂/methanol w/ diethylamine] or CHIRAL-PAK IA column [hexane/ethanol/tetrahydrofuran w/ diethylamine]).

Example 30

(R)-3-(4-Chlorophenyl)-2-(4-(2-(3-(fluoromethyl)azetidin-1-yl)ethoxy)phenyl)-4-methyl-2H-chromen-7-ol

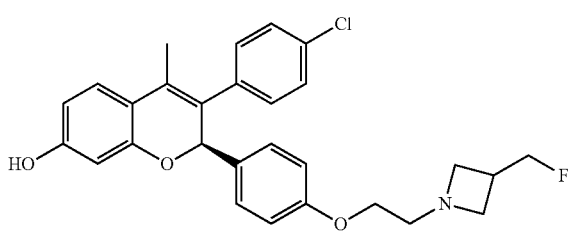 [SMILES: CC1=C(c2ccc(Cl)cc2)[C@@H](c2ccc(OCCN3CC(CF)C3)cc2)Oc2cc(O)ccc21]

Separation of the enantiomers from the racemic mixture of Example 28 provides the title compound. Suitable separation techniques include chiral chromatography (e.g. Regis-Cell column [CO₂/methanol w/ diethylamine] or CHIRAL-PAK IA column [hexane/ethanol/tetrahydrofuran w/ diethylamine]).

Example 31

3-(3-Hydroxyphenyl)-4-methyl-2-(4-(2-(3-methyl-azetidin-1-yl)ethoxy)phenyl)-2H-chromen-6-ol

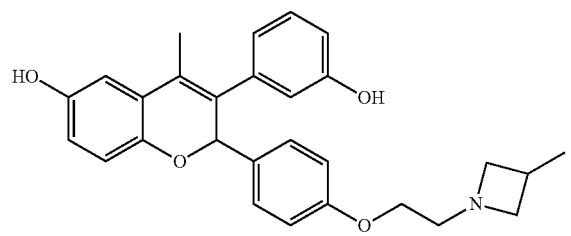 [SMILES: CC1=C(c2cccc(O)c2)C(c2ccc(OCCN3CC(C)C3)cc2)Oc2ccc(O)cc21]

Step 1: 2-(3-Methoxyphenyl)acetyl chloride

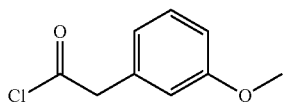

Thionyl chloride (1 L) was added over 30 min to a suspension of 2-(3-methoxyphenyl)acetic acid (530 g, 3.19 mol) and dry dichloromethane (3 L) in an ice bath. N,N-Dimethylformamide (15 mL) was added dropwise over 10 min keeping the internal temperature below 20° C. The ice bath was removed, and the reaction mixture was stirred until gas evolution has ceased. The mixture was heated at reflux (~50° C.) for 3 h, stirred at room temperature overnight, and then concentrated to give a yellow oil which was used directly in the next step.

Step 2: 1-(2,5-Dimethoxyphenyl)-2-(3-methoxyphenyl)ethanone

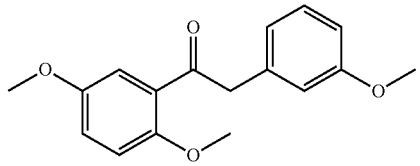

1,4-Dimethoxybenzene (400 g, 3.19 mol) was added to a suspension of AlCl₃ (400 g, 3.5 mol) and dry dichloromethane (10 L) in an ice/dry ice bath. A solution of 2-(3-methoxyphenyl)acetyl chloride (606 g, 3.19 mol) in dichloromethane (1 L) was added dropwise over 3 h keeping the internal temperature below 0° C. The resulting mixture was stirred at 0° C. for 1 h, poured into ice water (5 L) over 30 min with stirring (exothermic), and then extracted with dichloromethane (5 L×2). The combined organic layers were washed with 1 N aqueous HCl (2 L), saturated aqueous NaHCO₃ (2 L), and then brine (2 L). The resulting solution was dried (MgSO₄), concentrated, and purified by silica gel chromatography [petroleumether (bp: 60-90° C.)/EtOAc-5:1] to give 1-(2,5-dimethoxyphenyl)-2-(3-methoxyphenyl)ethanone (500 g). ¹H NMR (DMSO-d₆, 300 MHz): δ 7.19 (dd, 1H), 7.05-7.10 (m, 3H), 6.74-6.79 (m, 3H), 4.22 (s, 2H), 3.85 (s, 3H), 3.71 (s, 6H).

Step 3: 1-(2,5-Dihydroxyphenyl)-2-(3-hydroxyphenyl)ethanone

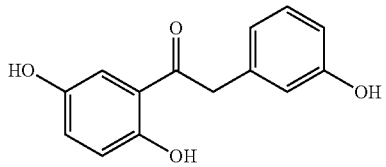 [SMILES: O=C(Cc1cccc(O)c1)c1cc(O)ccc1O]

Boron tribromide (332 mL, 3.5 mol) was added dropwise (internal temperature<−60° C.) to a solution of 1-(2,5-dimethoxyphenyl)-2-(3-methoxyphenyl)ethanone (264 g, 0.92 mol) in dry dichloromethane (1 L) at −78° C. The mixture was stirred at −78° C. for 30 min, warmed to 0° C. over 30 min, and then stirred at 0° C. for an additional hour. Methanol (100 mL) and then water (100 mL) were added dropwise keeping the internal temperature below 20° C., and the mixture was stirred at room temperature for 1 h. The resulting precipitate was collected by filtration, washed with water (500 mL), and dried to afford 1-(2,5-dihydroxyphenyl)-2-(3-hydroxyphenyl)ethanone (125 g). ¹H NMR (DMSO-d₆, 300 MHz): δ 11.50 (br, 1H), 9.29 (br, 2H), 7.27 (d, 1H), 7.10 (t, 1H), 6.99 (dd, 1H), 6.81 (d, 1H), 6.70-6.62 (m, 3H), 4.24 (s, 2H). LCMS: 243.0 [M−H]⁻.

Step 4: 1-(2-Hydroxy-5-((tetrahydro-2H-pyran-2-yl)oxy)phenyl)-2-(3-((tetrahydro-2H-pyran-2-yl)oxy)phenyl)ethanone

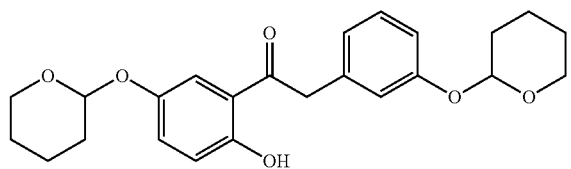 [SMILES: O=C(Cc1cccc(OC2CCCCO2)c1)c1cc(OC2CCCCO2)ccc1O]

Pyridinium p-toluenesulfonate (53.6 g, 0.2 mol) was added over 1 h to a solution of 1-(2,5-dihydroxyphenyl)-2-(3-hydroxyphenyl)ethanone (280 g, 1.06 mol), 3,4-dihydro-2H-pyran (628 g, 7.48 mol), and dichloromethane (2.5 L) at 5-8° C. The mixture was stirred at rt for 4 h, concentrated, and then purified by silica gel chromatography [petroleumether (bp: 60-90° C.)/EtOAc-10:1] to give 1-(2-hydroxy-5-((tetrahydro-2H-pyran-2-yl)oxy)phenyl)-2-(3-((tetrahydro-2H-pyran-2-yl)oxy)phenyl)ethanone (305 g). ¹H NMR (DMSO-d₆, 300 MHz): δ 11.37 (s, 1H), 7.58 (d, 1H), 7.19-7.27 (m, 2H), 6.87-6.94 (m, 4H), 5.39-5.42 (m, 2H), 4.37 (s, 2H), 3.75-3.79 (m, 2H), 3.51-3.56 (m, 2H), 1.46-1.85 (m, 12H); LCMS: 413.2 [M+H]⁺.

Step 5: 2-(4-Iodophenyl)-6-((tetrahydro-2H-pyran-2-yl)oxy)-3-(3-((tetrahydro-2H-pyran-2-yl)oxy)phenyl)chroman-4-one

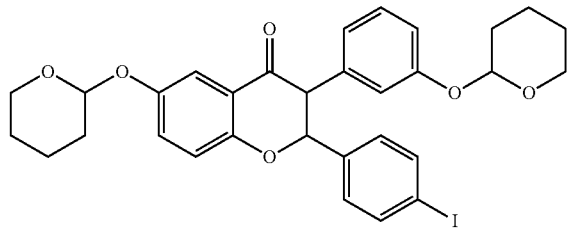 [SMILES: O=C1c2cc(OC3CCCCO3)ccc2OC(c2ccc(I)cc2)C1c1cccc(OC2CCCCO2)c1]

1,8-Diazabicyclo[5.4.0]undec-7-ene (54.3 g, 0.32 mol), 4-iodobenzaldehyde (264 g, 1.09 mol), and piperidine (30.3 g, 0.32 mol) were added to a solution of 1-(2-hydroxy-5-((tetrahydro-2H-pyran-2-yl)oxy)phenyl)-2-(3-((tetrahydro-2H-pyran-2-yl)oxy)phenyl)ethanone (446 g, 1.08 mol) in n-BuOH (600 mL). The mixture was heated at 120° C. for 6 h, stirred at rt for 2 d, and then concentrated. Petroleumether (2 L) was added to the residue, the mixture was stirred for 30 min, and the resulting precipitate was collected by filtration to give 2-(4-iodophenyl)-6-((tetrahydro-2H-pyran-2-yl)oxy)-3-(3-((tetrahydro-2H-pyran-2-yl)oxy)phenyl)chroman-4-one (400 g). The filtrate was concentrated and purified by silica gel chromatography [petroleumether (bp: 60-90° C.)/EtOAc-20:1] to give an additional 110 g. ¹H NMR (DMSO-d₆, 300 MHz): δ 7.62 (d, 2H), 7.41-7.43 (m, 1H), 7.32-7.33 (m, 1H), 7.05-7.30 (m, 4H), 6.71-6.81 (m, 3H), 5.83-5.87 (m, 1H), 5.46-5.48 (m, 1H), 5.30-5.32 (m, 1H), 4.58 (d, 1H), 3.51-3.75 (m, 4H), 1.51-1.85 (m, 12H).

Step 6: 2-(4-Iodophenyl)-4-methyl-6-((tetrahydro-2H-pyran-2-yl)oxy)-3-(3-((tetrahydro-2H-pyran-2-yl)oxy)phenyl)chroman-4-ol

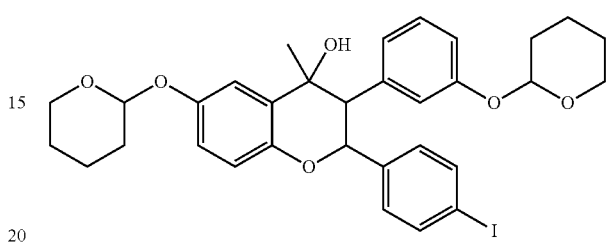

Methylmagnesium chloride (3 M in THF, 485 mL, 1.42 mol) was added over 1 h (internal temperature<0° C.) to a solution of 2-(4-iodophenyl)-6-((tetrahydro-2H-pyran-2-yl)oxy)-3-(3-((tetrahydro-2H-pyran-2-yl)oxy)phenyl)chroman-4-one (230 g, 0.367 mol) and dry tetrahydrofuran (1 L) in an ice/dry ice bath under N₂. The mixture was stirred at 0° C. for 30 min, stirred at room temperature for 4 h, and then re-cooled in an ice bath. Saturated aqueous NH₄Cl (300 mL) was added over 30 min, and the mixture was extracted with EtOAc (300 mL×3). The combined organic layers were dried (MgSO₄), concentrated, and then purified by silica gel chromatography [petroleumether (bp: 60-90° C.)/EtOAc-20:1] to give 2-(4-iodophenyl)-4-methyl-6-((tetrahydro-2H-pyran-2-yl)oxy)-3-(3-((tetrahydro-2H-pyran-2-yl)oxy)phenyl)chroman-4-ol (230 g). LCMS: 643.0 [M+H]⁺.

Step 7: 3-(3-Hydroxyphenyl)-2-(4-iodophenyl)-4-methyl-2H-chromen-6-ol

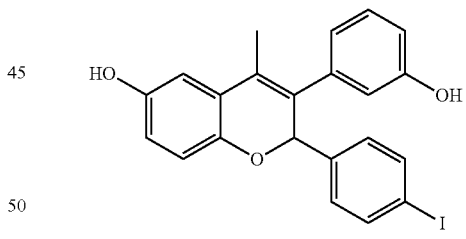

Acetic acid (3.2 L) was added to a suspension of 2-(4-iodophenyl)-4-methyl-6-((tetrahydro-2H-pyran-2-yl)oxy)-3-(3-((tetrahydro-2H-pyran-2-yl)oxy)phenyl)chroman-4-ol (200 g, 0.31 mol) in water (0.8 L). The reaction mixture was heated at 90° C. for 48 h and then concentrated to remove most of the AcOH. The aqueous residue was extracted with EtOAc (1 L×2). The combined organic layers were washed with saturated aqueous NaHCO₃ (500 mL), washed with brine (500 mL), dried (Na₂SO₄), concentrated, and then purified by silica gel chromatography [petroleumether (bp: 60-90° C.)/EtOAc-4:1] to afford 3-(3-hydroxyphenyl)-2-(4-iodophenyl)-4-methyl-2H-chromen-6-ol (95 g). ¹H NMR (DMSO-d₆, 400 MHz): δ 9.46 (s, 1H), 8.99 (s, 1H), 7.61 (d, 2H), 7.14 (t, 1H), 7.08 (d, 2H), 6.75-6.62 (m, 4H), 6.51 (s, 2H), 5.90 (s, 1H), 2.03 (s, 3H). LCMS: 455.0 [M−H]⁻.

Step 8: 2-(4-Iodophenyl)-4-methyl-6-((tetrahydro-2H-pyran-2-yl)oxy)-3-(3-((tetrahydro-2H-pyran-2-yl)oxy)phenyl)-2H-chromene

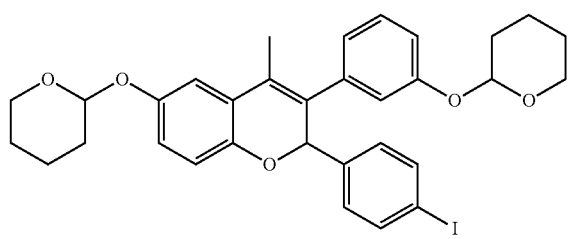 [SMILES: CC1=C(c2cccc(OC3CCCCO3)c2)C(c2ccc(I)cc2)Oc2ccc(OC3CCCCO3)cc21]

Pyridinium p-toluenesulfonate (32 g, 0.13 mol) was added over 10 min (5-8° C.) to a solution of 3-(3-hydroxyphenyl)-2-(4-iodophenyl)-4-methyl-2H-chromen-6-ol (150 g, 0.42 mol), 3,4-dihydro-2H-pyran (218 g, 2.53 mol), and dichloromethane (3.5 L) in an ice bath. The resulting mixture was stirred at rt for 2 h, concentrated, and purified by silica gel chromatography [petroleumether (bp: 60-90° C.)/EtOAc-40:1→20:1] to give 2-(4-iodophenyl)-4-methyl-6-((tetrahydro-2H-pyran-2-yl)oxy)-3-(3-((tetrahydro-2H-pyran-2-yl)oxy)phenyl)-2H-chromene (145 g). $^1$H NMR (DMSO-d$_6$, 400 MHz): δ 7.62 (dd, 2H), 7.27 (t, 1H), 7.10 (d, 2H), 7.00 (t, 1H), 6.90-6.94 (m, 3H), 6.80 (dd, 1H), 6.64 (dd, 1H), 6.04 (d, 1H), 5.39-5.45 (m, 1H), 5.35 (t, 1H), 3.70-3.81 (m, 2H), 3.50-3.58 (m, 2H), 2.06 (s, 3H), 1.52-1.87 (m, 12H).

Step 9: 3-(3-Hydroxyphenyl)-4-methyl-2-(4-(2-(3-methylazetidin-1-yl)ethoxy)phenyl)-2H-chromen-6-ol

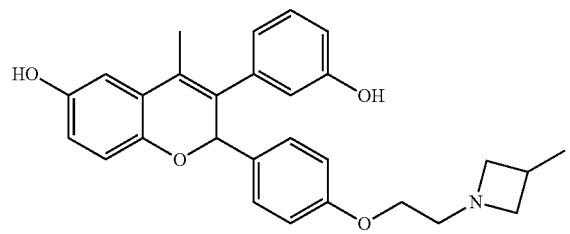 [SMILES: CC1=C(c2cccc(O)c2)C(c2ccc(OCCN3CC(C)C3)cc2)Oc2ccc(O)cc21]

A mixture of from 2-(4-iodophenyl)-4-methyl-6-((tetrahydro-2H-pyran-2-yl)oxy)-3-(3-((tetrahydro-2H-pyran-2-yl)oxy)phenyl)-2H-chromene (620 mg, 1.0 mmol), 2-(3-methylazetidin-1-yl)ethanol (0.17 g, 1.5 mmol, Intermediate 2), CuI (38 mg, 0.2 mmol), K$_2$CO$_3$ (280 mg, 2.0 mmol), and butyronitrile (2 mL) was degassed with three vacuum/N$_2$ cycles and then heated at 130° C. for 2 days. After cooling, the reaction mixture was diluted with ethyl acetate and filtered through Celite. The filtrate was diluted with water and extracted with ethyl acetate. The organic layer was washed with water, brine and dried over sodium sulfate, and filtered. The filtrate was concentrated to give the crude 3-methyl-1-(2-(4-(4-methyl-6-((tetrahydro-2H-pyran-2-yl)oxy)-3-(3-((tetrahydro-2H-pyran-2-yl)oxy)phenyl)-2H-chromen-2-yl)phenoxy)ethyl)azetidine as thick gum. This crude material was suspended in 80% acetic acid in water (10 mL) and stirred at room temperature for 16 h. Excess solvent was removed on a rotary evaporator to give a residue that was redissolved in ethyl acetate, washed with water, sat'd sodium bicarbonate, brine and dried over sodium sulfate, filtered and concentrated. The crude material was purified on silica gel eluted with 0-10% methanol in dichloromethane to afford 3-(3-hydroxyphenyl)-4-methyl-2-(4-(2-(3-methylazetidin-1-yl)ethoxy)phenyl)-2H-chromen-6-ol:
$^1$H NMR (400 MHz, DMSO-d$_6$) δ: 9.43 (s, 1H), 8.94 (s, 1H), 7.18 (m, 2H), 7.12 (t, 1H), 6.80-6.73 (m, 3H), 6.69-6.60 (m, 3H), 6.52-6.45 (m, 2H), 5.76 (s, 1H), 3.81 (t, 2H), 3.37 (t, 2H), 2.72 (t, 2H), 2.66 (t, 2H), 2.44-2.36 (m, 1H), 2.02 (s, 3H), 1.06 (d, 3H); LCMS: 444.0 [M+H]$^+$.

Example 32

(S)-3-(3-Hydroxyphenyl)-4-methyl-2-(4-(2-(3-methylazetidin-1-yl)ethoxy)phenyl)-2H-chromen-6-ol

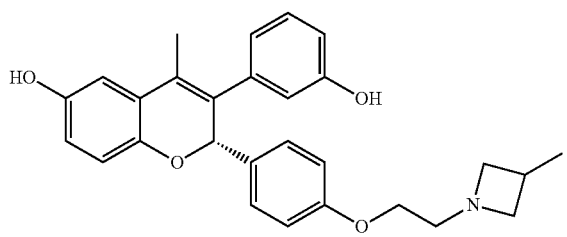 [SMILES: CC1=C(c2cccc(O)c2)[C@H](c2ccc(OCCN3CC(C)C3)cc2)Oc2ccc(O)cc21]

Separation of the enantiomers from the racemic mixture of Example 31 provides the title compound. Suitable separation techniques include chiral chromatography (e.g. Regis-Cell column [CO$_2$/methanol w/ diethylamine] or CHIRAL-PAK IA column [hexane/ethanol/tetrahydrofuran w/ diethylamine]).

Example 33

(R)-3-(3-Hydroxyphenyl)-4-methyl-2-(4-(2-(3-methylazetidin-1-yl)ethoxy)phenyl)-2H-chromen-6-ol

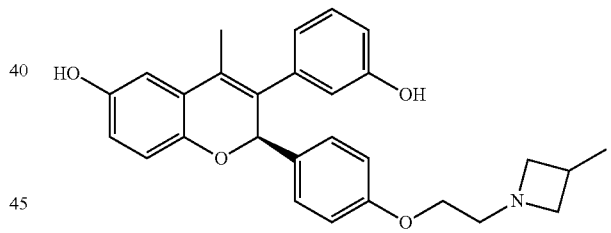

Separation of the enantiomers from the racemic mixture of Example 31 provides the title compound. Suitable separation techniques include chiral chromatography (e.g. Regis-Cell column [CO$_2$/methanol w/ diethylamine] or CHIRAL-PAK IA column [hexane/ethanol/tetrahydrofuran w/ diethylamine]).

Example 34

3×ERE MCF-7 Reporter Assay

MCF7 cells were maintained in RPMI 1640 supplemented with 10% FCS. Transcriptional assays were performed by seeding 100 μL of cells at a density of 250,000 cells/mL into 96-well cell culture plates in RPMI 1640 supplemented with 10% charcoal stripped serum and allowed to attach overnight. Cells were transiently transfected using Lipofectin (Life Technologies) according to the manufacturer's protocol. Triplicate transfections were performed using 300 ng 3×ERE-TK-Luc (reporter vector), 50 ng CMVpRL (normalization vector), and 130 ng pCMX (filler DNA). Transfected cells were incubated overnight then treated with ligand. For ER agonist assays, the compounds were serially diluted and 50 μL of compound plus RPMI 1640 supplemented with charcoal stripped serum was added to the cells. For ER antagonist assays, the compounds were serially diluted and 50 μL of compound with RPMI plus 17β-estradiol supplemented with charcoal stripped serum were added to the cells. The final 17β-estradiol concentration used in the antagonist assays was 0.1 nM. Following 24 hour incubation the medium was removed and the cells were lysed in 40 μL of lysis buffer (25 mM Tris Phosphate, 2 mM CDTA, 10% Glycerol, 0.5% Triton X-100, 2 mM DTT). Firefly luciferase activity was measured immediately following the addition of 40 μL luciferase buffer (20 mM tricine, 0.1 mM EDTA, 1.07 mM $(MgCO_3)_4Mg(OH)_2 \cdot 5H_2O$, 2.67 mM $MgSO_4$, 33.3 mM DTT, 270 Coenzyme A, 470 μM luciferin, 530 μM ATP). Renilla luciferase was measured following the addition of 40 μL colelenterazine buffer (1.1 M NaCl, 2.2 mM $Na_2EDTA$, 0.22 M $KxPO_4$ (pH 5.1), 0.44 mg/mL BSA, 1.3 mM $NaN_3$, 1.43 μM coelenterazine, final pH adjusted to 5.0).

Example 35

Breast Cancer Cell Viability Assays

MCF-7 cells were adjusted to a concentration of 40,000 cells per mL in RPMI containing 10% FBS and 20 mM HEPES. 16 microliters of the cell suspension (640 cells) was added to each well of a 384 well plate, and the cells were incubated overnight to allow the cells to adhere. The following day a 10 point, serial 1:5 dilution of each compound was added to the cells in 16 μL at a final concentration ranging from 10-0.000005 μM. After 5 days' compound exposure, 16 μL of CellTiter-GLo (Promega, Madison Wis.) was added to the cells, and the relative luminescence units (RLUs) of each well were determined. CellTiter-Glo added to 32 μL of medium without cells was used to obtain a background value. The Percent viability of each sample was determined as follows:

(RLU sample−RLU background/RLU untreated cells-RLU background)×100=% viability.

"% Viability relative to Fulvestrant" is calculated as follows:

100−{100*[(100−% viability of Example)/(100−% viability of Fulvestrant)]}.

Viability effects in additional ER+ breast cancer cell lines, including BT474, CAMA1, MDA-MB-361, ZR-75-1, T47D, can be profiled in assays similar to Example 35.

Illustrative biological data for representative compounds disclosed herein is presented in the following table:

TABLE 1

| Example | MCF7 Viability Assay $IC_{50}$ | MCF7 Viability Assay: % Viability relative to Fulvestrant |
|---|---|---|
| 1 | 0.36 nM | 3 |
| 2 | 26 nM | 3 |
| 3 | 0.17 nM | 8 |
| 4 | 1.2 nM | 3 |
| 7 | 3.5 nM | 0 |

TABLE 1-continued

| Example | MCF7 Viability Assay $IC_{50}$ | MCF7 Viability Assay: % Viability relative to Fulvestrant |
|---|---|---|
| 10 | 0.41 nM | 2 |
| 13 | 0.53 nM | 1 |
| 16 | 0.71 nM | 1 |
| 19 | 0.42 nM | 0 |
| 22 | 12 nM | 6 |
| 25 | 0.3 nM | 7 |
| 28 | 0.8 nM | 6 |
| 31 | 0.2 nM | 13 |
| 3-(4-fluorophenyl)-4-methyl-2-(4-((S)-2-((R)-3-methylpyrrolidin-1-yl)propoxy)phenyl)-2H-chromen-6-ol | 0.4 nM | 17 |
| (R)-3-(4-fluorophenyl)-4-methyl-2-(4-((S)-2-((R)-3-methylpyrrolidin-1-yl)propoxy)phenyl)-2H-chromen-6-ol | Not tested | Not tested |
| (S)-3-(4-fluorophenyl)-4-methyl-2-(4-((S)-2-((R)-3-methylpyrrolidin-1-yl)propoxy)phenyl)-2H-chromen-6-ol | 0.3 | 14 |
| 3-(4-chlorophenyl)-4-methyl-2-(4-((S)-2-((R)-3-methylpyrrolidin-1-yl)propoxy)phenyl)-2H-chromen-6-ol | 1.9 nM | 14 |
| 4-(6-hydroxy-4-methyl-2-(4-((S)-2-((R)-3-methylpyrrolidin-1-yl)propoxy)phenyl)-2H-chromen-3-yl)benzonitrile | 10 nM | 15 |
| 3-(3,4-difluorophenyl)-4-methyl-2-(4-((S)-2-((R)-3-methylpyrrolidin-1-yl)propoxy)phenyl)-2H-chromen-6-ol | 0.7 nM | 19 |
| (S)-3-(3-Hydroxyphenyl)-4-methyl-2-(4-((S)-2-((R)-3-methylpyrrolidin-1-yl)propoxy)phenyl)-2H-chromen-6-ol | 0.13 nM | 8 |
| Fulvestrant | 0.57 nM | 0 |

Example 36

Breast Cancer Cell ER-α in Cell Western Assay (SP1)

MCF7 cells were trypsinized and washed twice in Phenol Red Free RPMI containing 5% Charcoal Dextran Stripped serum with 20 mM HEPES and NEAA, then adjusted to a concentration of 200,000 cells per mL with the same medium. Next, 16 μL of the cell suspension (3200 cells) was added to each well of a poly-D-lysine coated 384 well plate, and the cells were incubated at 37° C. over 4 days to allow the cells to adhere and grow. On day 4, a ten point, serial 1:5 dilution of each compound was added to the cells in 16 μL at a final concentration ranging from $10^{-5}$M to $5.12 \times 10^{-12}$M or $10^{-6}$M to $5.12 \times 10^{-13}$M for fulvestrant. At 4 hours post compound addition, the cells were fixed by adding 16 μL of 30% formalin to the 32 μL of cells and compound (10% formalin final concentration) for 20 minutes. Cells were then washed twice with PBS Tween 0.1% and then permeabilized in PBS 0.1% Triton (50 μl/well) for additional 15 minutes. The PBS 0.1% triton was decanted, and the cells were washed: LI-COR blocking buffer (50 μL/well) was added, the plate was spun at 3000 rpm, and then the blocking buffer was decanted. Additional LI-COR blocking buffer (50 μL/well) was added, and the cells were incubated overnight at 4° C. The blocking buffer was decanted, and the cells were incubated overnight at 4° C. with SP1 (Thermo Scientific) anti-ER rabbit monoclonal antibody diluted 1:1000 in LI-COR blocking buffer/0.1% Tween-20. Wells which were treated with blocking buffer with Tween but no antibody were used as a background control. Wells were washed twice with PBS Tween 0.1% to remove free SP1 antibodies, and the cells were incubated at room temp for 60-90 minutes in LI-COR goat anti-rabbit IRDye™ 800 CW (1:1000) and DRAQ5 DNA dye (1:10000 of 5 mM stock solution) diluted in LI-COR blocking buffer containing 0.1% Tween-20 and 0.01% SDS. Cells were then washed with 0.1% Tween-20/PBS three times. Plates were scanned on a LI-COR Odyssey infrared imaging system. Integrated intensities in the 800 nm channel and 700 nm channel were measured to determine levels of ER-α and DNA respectively. Percent ER levels were determined as follows:

(Integrated intensity 800 nm sample/integrated intensity 700 nm sample)/(Integrated intensity 800 nm untreated cells/integrated intensity 700 nm untreated cells)×100=% ER-α levels.

"% ER-α remaining relative to Fulvestrant" is calculated as follows:

100−{100*[(100−% ER level of Example)/(100−% ER level of Fulvestrant)]}.

Effects on steady state levels of ER-α in additional ER+ breast cancer cell lines, including BT474, CAMA1, MDA-MB-361, ZR-75-1, T47D, can be profiled in assays similar to Example 36.

Illustrative biological data for representative compounds disclosed herein is presented in the following table:

TABLE 2

| Example | ER-α In-Cell Western Assay (SP1); IC$_{50}$ | ER-α In-Cell Western Assay (SP1): % ER-α remaining relative to Fulvestrant |
|---|---|---|
| 1 | 0.41 nM | 2 |
| 2 | 15 nM | 2 |
| 3 | 0.14 nM | 3 |
| 4 | 1.1 nM | 3 |
| 7 | 1.8 nM | 2 |
| 10 | 0.51 nM | 1 |
| 13 | 0.52 nM | 2 |
| 16 | 1.1 nM | 1 |
| 19 | 0.60 nM | 0 |
| 22 | 4.9 nM | 8 |
| 25 | 0.3 nM | 2 |
| 28 | 0.9 nM | 3 |
| 31 | 0.3 nM | 14 |
| 3-(4-fluorophenyl)-4-methyl-2-(4-((S)-2-((R)-3-methylpyrrolidin-1-yl)propoxy)phenyl)-2H-chromen-6-ol | 0.4 nM | 18 |
| (R)-3-(4-fluorophenyl)-4-methyl-2-(4-((S)-2-((R)-3-methylpyrrolidin-1-yl)propoxy)phenyl)-2H-chromen-6-ol | 18 nM | 13 |
| (S)-3-(4-fluorophenyl)-4-methyl-2-(4-((S)-2-((R)-3-methylpyrrolidin-1-yl)propoxy)phenyl)-2H-chromen-6-ol | 0.4 nM | 16 |
| 3-(4-chlorophenyl)-4-methyl-2-(4-((S)-2-((R)-3-methylpyrrolidin-1-yl)propoxy)phenyl)-2H-chromen-6-ol | 1.4 nM | 15 |
| 4-(6-hydroxy-4-methyl-2-(4-((S)-2-((R)-3-methylpyrrolidin-1-yl)propoxy)phenyl)-2H-chromen-3-yl)benzonitrile | 1.5 nM | 16 |
| 3-(3,4-difluorophenyl)-4-methyl-2-(4-((S)-2-((R)-3-methylpyrrolidin-1-yl)propoxy)phenyl)-2H-chromen-6-ol | 1.5 nM | 14 |
| (S)-3-(3-Hydroxyphenyl)-4-methyl-2-(4-((S)-2-((R)-3-methylpyrrolidin-1-yl)propoxy)phenyl)-2H-chromen-6-ol | 0.11 nM | 9 |
| Fulvestrant | 0.39 nM | 0 |

Example 37

Ishikawa Uterine Cell Alkaline Phosphatase Assay

Subconfuent Ishikawa cells in a T225 are incubated 24 hours in an estrogen free basal medium (EFBM) consisting of DMEM:Ham's F-12 50:50 phenol red free basal medium containing 5% Charcoal Dextran treated FBS and 20 mM HEPES. Cells are plated the following day in EFBM in clear 384 well plates at a concentration of 2.5×105 cells per mL, 16 µL per well (4000 cells per well). A 12 point semi log dilution of each compound is carried out in DMSO and subsequently diluted in EFBM. An equal volume of compound in EFBM is added immediately after plating cells, and the cells are incubated for 3 days. The cells are fixed with 5% formalin, and rinsed with PBS. Alkaline Phosphatase substrate 4-Nitrophenyl phosphate disodium salt hexahydrate is added (1 mg/mL final concentration) to a solution containing 2 mM MgCl$_2$, 1 M diethanolamine, and adjusted to pH 9.0. The substrate solution is added to the cell cultures (16 µL per well), and OD405 is measured in a multiwall plate spectrophotometer when the optical density at 405 nm wavelength of cells treated with 17β-estradiol in the concentration range of 1-30 nM reaches 1.0-1.2 absorbance units. Cells treated with DMSO alone serve as a background control. Percent activity in background subtracted samples is measured as follows:

% activity=OD405 sample/OD405 max of 17β-estradiol treated cells×100.

Example 38

Ovarian Cancer Cell Viability Assays

BG-1 cells are diluted in RPMI containing 10% FBS and 20 mM HEPES. 16 microliters of the cell suspension is added to each well of a 384 well plate, and the cells are incubated overnight. The following day an eleven point, serial semi log dilution of each compound is added to the cells in 16 µL at a final concentration ranging from 0.3-0.000003 µM. After 5 to 7 days' compound exposure, 16 µL of CellTiter-GLo (Promega, Madison Wis.) is added to the cells, and the relative luminescence units (RLUs) of each well is determined. CellTiter-Glo added to 32 µL of medium without cells is used to obtain a background value. The Percent viability of each sample is determined as follows:

(RLU sample−RLU background/RLU untreated cells−RLU background)×100=% viability.

Viability effects in additional ER+ ovarian cancer cell lines, including A1847, SKOV3, SW626, A2780, can be profiled in assays similar to Example 38.

Example 39

Ovarian Cancer Cell ER-α in Cell Western Assay

BG-1 cells are diluted in RPMI containining 10% charcoal-stripped FBS and 20 mM HEPES. 16 microliters of the cell suspension is added to each well of a poly-D-lysine 384 well plate, and the cells are incubated overnight. The following day an eleven point, serial semi log dilution of each compound is added to the cells in 16 µL at a final concentration ranging from 0.3-0.000003 µM. At 4 or 24 hr post compound addition, the cells are fixed (10% formalin in PBS) for 20 minutes. Following fixation the cells are permeablized in PBS 0.1% Triton and blocked with LICOR blocking buffer (50 µl/well, 90'). The wells are then incubated overnight at 4° C. with SP1 rabbit monoclonal Ab (Thermo Scientific) diluted 1:1000 in LICOR blocking buffer/0.1% Tween-20. Wells treated with blocking buffer with Tween but no antibody are used as a background control. All wells are washed with 0.1% Tween-20/PBS and then incubated in goat anti-mouse IRDye™ 800 CW (LI-COR Inc.; 1:10000) and DRAQ5 DNA dye (1:2000 for 2 mM stock) diluted in LICOR blocking buffer containing 0.1% Tween-20 and 0.01% SDS for 60 minutes. Cells are then washed (50 µl/well, 5' each) in 0.1% Tween-20/PBS. Plates are scanned on a LICOR Odyssey infrared imaging system. Integrated intensities in the 800 nm channel and 700 nm channel are measured to determine levels of ER and DNA respectively. Percent ER levels are determined as follows:

(Integrated intensity 800 nm sample/integrated intensity 700 nm sample)/(Integrated intensity 800 nm untreated cells/integrated intensity 700 nm untreated cells)×100=% ER levels.

Effects on steady state levels of ER-α in additional ER+ ovarian cancer cell lines, including A1847, SKOV3, SW626, A2780, can be profiled in assays similar to Example 39.

Other cancer cell lines contemplated for testing compounds described herein include: ER-positive endometrial cell lines (Ishikawa, ECC1, HEC-1, EnCa-101) and ER-positive cervical cell lines (Caski, HeLa, SiHa).

Example 40

PEO Cell Viability Assays

PEO-1, PEO-4 and PEO-6 ovarian cancer cell lines were adjusted to a concentration of 20,000 cells per mL in RPMI containing 10% FBS. 16 microliters of the cell suspension (320 cells) was added to each well of a 384 well plate, and the cells were incubated overnight to allow the cells to adhere. The following day a 10 point, serial 1:5 dilution of each compound was added to the cells in 16 µL at a final concentration ranging from 1-0.0000005 µM. After 7 days' compound exposure, 16 µL of CellTiter-GLo (Promega, Madison Wis.) was added to the cells the the relative luminescence units (RLUs) of each well was determined. CellTiter-Glo added to 32 µL of medium without cells was used to obtain a background value. The Percent viability of each sample was determined as follows:

(RLU sample−RLU background/RLU untreated cells−RLU background)×100=% viability.

Example 41

PEO ER Western Analysis

Cells were plated in RPMI 5% CSS for 48 hours, then treated with compound for 4 or 24 hours. Cells were lysed in modified radioimmunoprecipitation buffer (mRIPA; 10 mM Tris, 150 mM NaCl, 1% (v/v) NP-40, 0.5% deoxycholate, 0.1% SDS, 5 mM EDTA, pH 7.4) containing Halt Protease & Phosphatase Single-Use Inhibitor Cocktail (Thermo Scientific, Cat. No. 78442). Total protein of the clarified lysates was quantitated by Lowry Assay (Biorad DC protein assay). NuPAGE® LDS Sample Buffer and Sample Reducing Agent were added to the lysates and heated to 70° C. for 10 mins. 15 ug of total cell protein was separated electrophoretically in a NuPAGE 4-12% Bis Tris Gel in MOPS SDS running buffer, then transferred to a nitrocellulose membrane in transfer buffer using an XCell II blot module. Membranes were incubated in Blocking Buffer (LI-COR, Lincoln, Nebr.) for 30 minutes at room temperature, followed by 60 minute incubations with a rabbit antibody against ER alpha (SP-1, Thermo Fisher Scientific, Cat. No. RM-9101), ER beta (Cell Signaling Technology, Cat. No. 5513), or mouse antibody against alpha tubulin (Sigma, Cat. No. T6199). Following incubation with an IRDye® Conjugated Goat Anti Mouse or Anti Rabbit IgG (LI-COR), protein bands were quantified using an Odyssey® Infrared Imaging System. Graphing of data to determine ER levels was performed using Graphpad PRISM® software. % ER levels were calculated as follows:

$$\% \ ER = \left( \frac{\text{fluorescence } ER \text{ band of sample-}bkgrd/\text{fluorescence Tubulin band of sample-}bkgrd}{\text{fluorescence } ER \text{ band of untreated cells-}bkgrd/\text{fluorescence Tubulin of untreated cells-}bkgrd} \right)$$

Example 42

Breast Cancer Model; Xenograft Assay (MCF-7)

Time release pellets containing 0.72 mg 17β Estradiol were subcutaneously implanted into nu/nu mice. MCF-7 cells were grown in RPMI containing 10% FBS at 5% $CO_2$, 37° C. Cells were spun down and re-suspended in 50% RPMI (serum free) and 50% Matrigel at $1\times10^7$ cells/mL. MCF-7 cells were subcutaneously injected (100 µL/animal) on the right flank 2-3 days post pellet implantation. Tumor volume (length×width$^2$/2) was monitored bi-weekly. When tumors reached an average volume of ~200 mm$^3$ animals were randomized and treatment was started. Animals were treated with Vehicle or Compound daily for 4 weeks. Tumor volume and body weight were monitored bi-weekly throughout the study. At the conclusion of the treatment period, plasma and tumor samples were taken for pharmacokinetic and pharmacodynamic analyses, respectively.

Example 43

Breast Cancer Model; Xenograft Assay (MCF-7 Derivative)

Female nu/nu mice (with supplemental 17-β Estradiol pellets; 0.72 mg; 60 day slow release) bearing MCF-7 tumors (mean tumor volume 200 mm$^3$) were treated with Tamoxifen (citrate) by oral gavage. Tumor volume (length×width$^2$/2) and body weight were monitored twice weekly. Following a significant anti-tumor response in which tumor volume remained static, evident tumor growth was first observed at approximately 100 days of treatment. At 120 days of treatment, tamoxifen dose was increased. Rapidly growing tumors were deemed tamoxifen resistant and selected for in vivo passage into new host animals. Tumor Fragments (~100 mm$^3$/animal) from the tamoxifen resistant tumors were subcutaneously implanted into the right flank of female nu/nu mice (with 17-β Estradiol pellets (0.72 mg; 60 day slow release)). Passaged tumors were maintained under constant Tamoxifen selection, and Tumor volume (length×width$^2$/2) was monitored weekly. When tumor volume reached ~150-250 mm$^3$, animals were randomized into treatment groups (mean tumor volume 200 mm$^3$) and tamoxifen treatment was terminated (except for a tamoxifen control arm). Animals were treated with Vehicle or Compound daily for 4 weeks. Tumor volume and body weight were monitored twice weekly for the duration of the study. At the conclusion of the treatment period; plasma and tumor samples were taken for pharmacokinetic and pharmacodynamic analyses, respectively.

TABLE 3

| Example | Number of Tumors Smaller at t = 27 days than at Start of study (t = 0 days) | | | |
|---|---|---|---|---|
| | Vehicle | 10mpk* | 30mpk* | 100mpk* |
| 3 | 0/8 | 2/8 | 3/8 | 5/8 |
| (S)-3-(3-Hydroxyphenyl)-4-methyl-2-(4-((S)-2-((R)-3-methylpyrrolidin-1-yl)propoxy)phenyl)-2H-chromen-6-ol | 0/8 | 0/8 | 1/8 | 1/8 |

*Oral dose administered to animals each day

Example 44

Ovarian Cancer Model; Xenograft Assay (BG-1)

Time release pellets (0.72 mg 17-β Estradiol/60 days) are subcutaneously implanted into female nu/nu mice. BG-1 cells are grown in DMEM Ham's F-12 50/50 containing 10% FBS, 10 mM Sodium Pyruvate, 10 mM Non-Essential Amino Acids at 5% $CO_2$, 37° C. Prior to injection, cells are trypsinized and suspended in 50% DMEM Ham's F-12 (serum free) and 50% Matrigel at $5\times10^7$ cells/mL. BG-1 cells are subcutaneously injected (100 μL/animal) on the right flank 2-3 days post pellet implantation. Tumor volume (length×width$^2$/2) is monitored bi-weekly. When tumors reach an average volume of ~250 mm$^3$ animals are randomized and treatment started. Animals are treated with Vehicle or Compound daily. Tumor volume and body weight are monitored bi-weekly throughout the study. At the conclusion of the treatment period; plasma and tumor samples are taken for pharmacokinetic and pharmacodynamic analyses, respectively.

Example 45

Endometrial Cancer Model; Xenograft Assay (ECC-1)

ECC-1 cells were grown in DMEM (phenol red, 4.5 g/L glucose and L-glutamine) containing 10% FBS, 1% Non-Essential Amino Acids and 100 units Penicillin/Streptomycin at 10% $CO_2$, 37° C. Cells were spun down and resuspended in 50% DMEM (serum free) and 50% Matrigel (BD, high concentration) at $5\times10^7$ cells/mL. Time release pellets (0.72 mg 17-(3 Estradiol/60 days) were subcutaneously implanted into female nu/nu mice. ECC-1 cells were subcutaneously injected (100 μL/animal) on the right flank 2-3 days post pellet implantation. Tumor volume was monitored and when tumors reached a suitable size for transplant they were excised. Excised tumors were cut into small pieces (~100 mm$^3$) and serially transplanted (10G trocar, right flank) into female nu/nu containing estradiol pellets (0.72 mg 17-β Estradiol/60 days) for 2-3 days. Tumor volume (length×width×width/2) was monitored and when palpable tumors were observed, animals were randomized and treatment was started. Animals were treated with Vehicle or Compound daily for 4 weeks or until tumor volume reached 2000 mm$^3$ (whichever came first). Tumor volume and body weight were monitored bi-weekly throughout the study. At the conclusion of the treatment period; plasma and tumor samples were taken for pharmacokinetic and pharmacodynamic analyses, respectively.

Example 46

Immature Uterine Wet Weight-Antagonist Mode

Female immature CD-IGS rats (21 days old upon arrival) were treated for three days. Animals were dosed daily for three days. Vehicle or test compound was administered orally by gavage followed 15 minutes later by an oral dose of 0.1 mg/kg Ethynyl Estradiol. On the fourth day 24 hours after dose, plasma was collected for pharmacokinetic analysis. Immediately following plasma collection, the animals were euthanized and the uterus was removed and weighed.

Example 47

Immature Uterine Wet Weight-Agonist Mode

Female immature CD-IGS rats (21 days old upon arrival) were treated for three days. Animals were dosed daily for three days. Vehicle or test compound was administered orally by gavage. On the fourth day 24 hours after dose, plasma was collected for pharmacokinetic analysis. Immediately following plasma collection, the animals were euthanized and the uterus was removed and weighed.

Example 48

Adult Uterine Wet Weight-10 Day

Female CD-IGS rats (69 days old, Charles River Laboratories) were purchased and split into groups. Group 1 was ovariectomized at the vendor (Charles River Laboratories) at 60 days of age and the study was started 2 weeks after surgery, while groups 2-8 were intact. Vehicle or test compound was administered orally for 10 days. Two hours after the $10^{th}$ and final dose, cardiac punctures were performed and serum was collected for pharmacokinetic and estradiol analyses. Immediately following serum collection, the animals were euthanized and the uterus and ovaries were removed and weighed. Uteri and ovaries from 2 animals per group were fixed in 10% neutral buffered formalin and sent out to be paraffin embedded, sectioned and stained for H&E (SDPath). Stained tissues were analyzed in house and then sent out to be read by a board certified pathologist. Uteri and ovaries from 4 animals per group were flash frozen in liquid $N_2$ for transcriptional analysis, examining a select set of genes modulated by the estrogen receptor.

Example 49

Breast Cancer Clinical Trial

Purpose:
The purposes of this study are to assess the efficacy of a compound of Formula (I), (II), or (III), or a pharmaceutically acceptable salt thereof, as first- or second-line treatment of estrogen receptor (ER) positive metastatic breast cancer, collect information on any side effects the compound may cause, and evaluate the pharmacokinetic properties of the compound.

Intervention:

Patients are administered 1-50 mg/kg of a compound of Formula (I), (II), or (III), or a pharmaceutically acceptable salt thereof, per day or twice a day.

Outcome Measures:

Primary Outcome Measures: tumor response and/or disease control.

Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description:

Patients will be given a compound of Formula (I), (II), or (III), or a pharmaceutically acceptable salt thereof, orally once or twice a day. Prior to each dosing cycle, a physical exam, blood work and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility:

Female subjects that are 18 years and older.

Inclusion Criteria:

Histologically or cytologically confirmed diagnosis of invasive breast cancer, stage IV disease; at least one measurable target lesion as defined by RECIST that has not been previously treated with local therapy; post-menopausal status; ER positive breast cancer; HER2-negative breast cancer; up to one prior hormonal therapy for advanced or metastatic disease; ECOG performance status 0-1; life expectancy>12 weeks; adequate liver and bone marrow function: AST<2.5×ULN; Bilirubin<1.5×ULN; ANC>1,500/ul; platelet count>100,000/ul; normal PT and PTT; at least 2 weeks since prior radiation and recovered from treatment-related toxicity.

Exclusion Criteria:

HER2-positive breast cancer; prior chemotherapy regimen for metastatic disease; history of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 50

Endometrial Carcinoma Clinical Trial

Purpose:

The purposes of this study are to assess the efficacy of a compound of Formula (I), (II), or (III), or a pharmaceutically acceptable salt thereof, in the treatment of advanced or metastatic endometrial carcinoma, collect information on any side effects the compound may cause, and evaluate the pharmacokinetic properties of the compound.

Intervention:

Patients are administered 1-50 mg/kg of a compound of Formula (I), (II), or (III), or a pharmaceutically acceptable salt thereof, per day or twice a day.

Outcome Measures:

Primary Outcome Measures: tumor response and/or disease control Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description:

Patients will be given a compound of Formula (I), (II), or (III), or a pharmaceutically acceptable salt thereof, orally once or twice a day. Prior to each dosing cycle, a physical exam, blood work and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility:

Female subjects that are 18 years and older.

Inclusion Criteria:

Histologically or cytologically confirmed diagnosis of advanced or metastatic endometrial carcinoma; at least one measurable target lesion as defined by RECIST that has not been previously treated with local therapy; hormone receptor positive endometrial carcinoma; ECOG performance status 0-1; life expectancy>12 weeks; adequate liver and bone marrow function: AST<2.5×ULN; Bilirubin<1.5×ULN; ANC>1,500/ul; platelet count>100,000/ul; normal PT and PTT; at least 2 weeks since prior radiation and recovered from prior surgery or treatment-related toxicity.

Exclusion Criteria:

History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 51

Ovarian Cancer Clinical Trial

Purpose:

The purposes of this study are to assess the efficacy of a compound of Formula (I), (II), or (III), or a pharmaceutically acceptable salt thereof, in the treatment of advanced ovarian cancer, collect information on any side effects the compound may cause, and evaluate the pharmacokinetic properties of the compound.

Intervention:

Patients are administered 1-50 mg/kg of a compound of Formula (I), (II), or (III), or a pharmaceutically acceptable salt thereof, per day or twice a day.

Outcome Measures:

Primary Outcome Measures: tumor response and/or disease control

Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description:

Patients will be given a compound of Formula (I), (II), or (III), or a pharmaceutically acceptable salt thereof, orally once or twice a day. Prior to each dosing cycle, a physical exam, blood work (including tumor markers, e.g., CA-125) and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility:
Female subjects that are 18 years and older.
Inclusion Criteria:
Histologically or cytologically confirmed diagnosis of advanced ovarian cancer; at least one measurable target lesion as defined by RECIST that has not been previously treated with local therapy; ER positive ovarian cancer; ECOG performance status 0-1; life expectancy>12 weeks; adequate liver and bone marrow function: AST<2.5×ULN; Bilirubin<1.5×ULN; ANC>1,500/ul; platelet count>100,000/ul; normal PT and PTT; at least 2 weeks since prior radiation and recovered from prior surgery or treatment-related toxicity.
Exclusion Criteria:
History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 52

ER-Positive NSCLC Clinical Trial

Purpose:
The purposes of this study are to assess the efficacy of a compound of Formula (I), (II), or (III), or a pharmaceutically acceptable salt thereof, as single agent or in combination in the treatment of advanced or metastatic estrogen receptor (ER) positive non-small cell lung cancer (NSCLC), collect information on any side effects the compound may cause as single agent or in combination, and evaluate the pharmacokinetic properties of the compound as single agent or in combination.
Intervention:
Patients are administered 1-50 mg/kg of a compound of Formula (I), (II), or (III), or a pharmaceutically acceptable salt thereof, per day or twice a day as single agent or in combination.
Outcome Measures:
Primary Outcome Measures: tumor response and/or disease control. Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.
Detailed Description:
Patients will be given a compound of Formula (I), (II), or (III), or a pharmaceutically acceptable salt thereof, orally once or twice a day as single agent or in combination. Prior to each dosing cycle, a physical exam, blood work and assessment of any side effects will be performed. Every 12 weeks the patient's cancer will be re-evaluated with either a CT scan or MRI to determine whether the treatment is working. Participation in this study will last until disease progression or unacceptable toxicity.
Eligibility:
Male and female subjects that are 18 years and older.
Inclusion Criteria:
Histologically or cytologically confirmed diagnosis of advanced or metastatic ER-positive NSCLC; at least one measurable target lesion as defined by RECIST that has not been previously treated with local therapy; ECOG performance status 0-1; life expectancy>12 weeks; adequate liver and bone marrow function: AST<2.5×ULN; Bilirubin<1.5× ULN; ANC>1,500/ul; platelet count>100,000/ul; normal PT and PTT; at least 2 weeks since prior radiation and recovered from prior surgery or treatment-related toxicity.
Exclusion Criteria:
History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 53

Endometriosis Clinical Trial

Purpose:
The purposes of this study are to assess the efficacy of a compound of Formula (I), (II), or (III), or a pharmaceutically acceptable salt thereof, as single agent or in combination in the treatment of patients with symptomatic/severe endometriosis, collect information on any side effects the compound may cause as single agent or in combination, and evaluate the pharmacokinetic properties of the compound as single agent or in combination.
Intervention:
Patients are administered 1-50 mg/kg of a compound of Formula (I), (II), or (III), or a pharmaceutically acceptable salt thereof, per day or twice a day as single agent or in combination.
Outcome Measures:
The outcome measures of this study are symptoms improvement and/or pain relief and shrinkage of endometrial tissue.
Detailed Description:
Patients will be given a compound of Formula (I), (II), or (III), or a pharmaceutically acceptable salt thereof, orally once or twice a day as single agent or in combination. Prior to each dosing cycle, a physical exam, blood work and assessment of any side effects will be performed.
Eligibility:
Female subjects that are 18 years and older.
Inclusion Criteria:
Diagnosis of symptomatic endometriosis; pre- or perimenopausal status; ECOG performance status 0-1; adequate liver and bone marrow function: AST<2.5×ULN; Bilirubin<1.5×ULN; ANC>1,500/ul; platelet count>100,000/ul; normal PT and PTT; at least 2 weeks since prior surgery or treatment-related toxicity.
Exclusion Criteria:
Pregnancy or lactating; history of other malignancy within the last 5 years, not including curatively-treated carcinoma in situ of the cervix or non-melanoma skin cancer; concurrent investigational drug treatment; uncontrolled infection; active cardiac disease; aerious medical or psychiatric illness.

Example 54

Uterine Leiomyoma Clinical Trial

Purpose:
The purposes of this study are to assess the efficacy of a compound of Formula (I), (II), or (III), or a pharmaceutically acceptable salt thereof, as single agent or in combination in the treatment of patients with symptomatic uterine leiomyoma, collect information on any side effects the compound may cause as single agent or in combination, and evaluate the pharmacokinetic properties of the compound as single agent or in combination.

Intervention:

Patients are administered 1-50 mg/kg of a compound of Formula (I), (II), or (III), or a pharmaceutically acceptable salt thereof, per day or twice a day as single agent or in combination.

Outcome Measures:

The outcome measures of this study are symptoms improvement and/or pain relief and shrinkage of leiomyomas.

Detailed Description:

Patients will be given a compound of Formula (I), (II), or (III), or a pharmaceutically acceptable salt thereof, orally once or twice a day as single agent or in combination. Prior to each dosing cycle, a physical exam, blood work and assessment of any side effects will be performed.

Eligibility:

Female subjects that are 18 years and older.

Inclusion Criteria:

Diagnosis of symptomatic uterine leiomyoma; pre- or peri-menopausal status; ECOG performance status 0-1; adequate liver and bone marrow function: AST<2.5×ULN; Bilirubin<1.5×ULN; ANC>1,500/ul; platelet count>100,000/ul; normal PT and PTT; at least 2 weeks since prior surgery or treatment-related toxicity.

Exclusion Criteria:

Pregnancy or lactating; history of other malignancy within the last 5 years, not including curatively-treated carcinoma in situ of the cervix or non-melanoma skin cancer; concurrent investigational drug treatment; uncontrolled infection; active cardiac disease; serious medical or psychiatric illness.

Example 55

Parenteral Pharmaceutical Composition

To prepare a parenteral pharmaceutical composition suitable for administration by injection (subcutaneous, intravenous), 100 mg of a water-soluble compound of Formula (I), (II), or (III), or pharmaceutically acceptable salt thereof, is dissolved in sterile water and then mixed with 10 mL of 0.9% sterile saline. The mixture is incorporated into a dosage unit form suitable for administration by injection In another embodiment, the following ingredients are mixed to form an injectable formulation: 1.2 g of a compound of Formula (I), (II), or (III), or a pharmaceutically acceptable salt thereof, 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example 56

Oral Solution

To prepare a pharmaceutical composition for oral delivery, an aqueous 20% propylene glycol solution is prepared. To this is added a sufficient amount of a compound of Formula (I), (II), or (III), or a pharmaceutically acceptable salt thereof, to provide a 20 mg/mL solution.

Example 57

Oral Capsule

To prepare a pharmaceutical composition for oral delivery, 10-1500 mg of a compound of Formula (I), (II), or (III), or a pharmaceutically acceptable salt thereof, is mixed with starch. The mixture is incorporated into an oral dosage unit such as a hard gelatin capsule, which is suitable for oral administration.

In another embodiment, 10-1500 mg of a compound of Formula (I), (II), or (III), or a pharmaceutically acceptable salt thereof, is placed into Size 4 capsule, or size 1 capsule (hypromellose or hard gelatin) and the capsule is closed.

Example 58

Oral Tablet

A tablet is prepared by mixing 48% by weight of a compound of Formula (I), (II), or (III), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

Example 59

Topical Gel Composition

To prepare a pharmaceutical topical gel composition, a compound of Formula (I), (II), or (III), or a pharmaceutically acceptable salt thereof, is mixed with hydroxypropyl cellulose, propylene glycol, isopropyl myristate and purified alcohol USP. The resulting gel mixture is then incorporated into containers, such as tubes, which are suitable for topical administration.

The examples and embodiments described herein are for illustrative purposes only and various modifications or changes suggested to persons skilled in the art are to be included within the spirit and purview of this application and scope of the appended claims.

What is claimed is:

1. A compound that has the following structure of Formula (III):

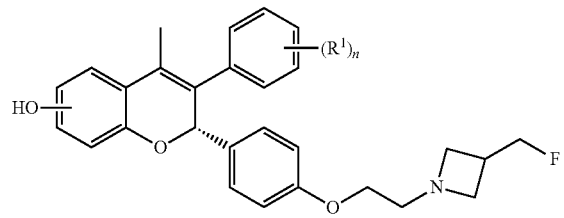

Formula (III)

wherein,
each $R^1$ is independently selected from the group consisting of halogen, —CN, —SO$_2$R$^2$, —OR$^2$, C$_1$-C$_4$ alkyl, and C$_1$-C$_4$ fluoroalkyl;

each R² is independently selected from the group consisting of $C_1$-$C_4$ alkyl, and $C_1$-$C_4$ fluoroalkyl; and n is 1, 2, or 3;

or a pharmaceutically acceptable salt, solvate or prodrug thereof.

2. The compound of claim 1, wherein each $R^1$ is independently selected from the group consisting of F, Cl, —CN, —$CF_3$, —$OCH_3$, and —$OCF_3$.

3. The compound of claim 1, wherein the compound of Formula (III) has one of the following structures:

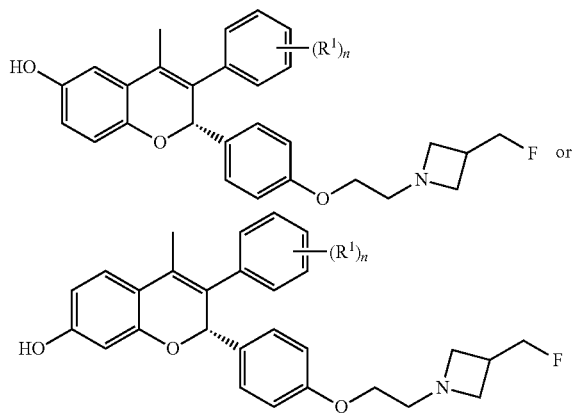

wherein n is 1.

4. The compound of claim 3, wherein the compound of Formula (III) has one of the following structures:

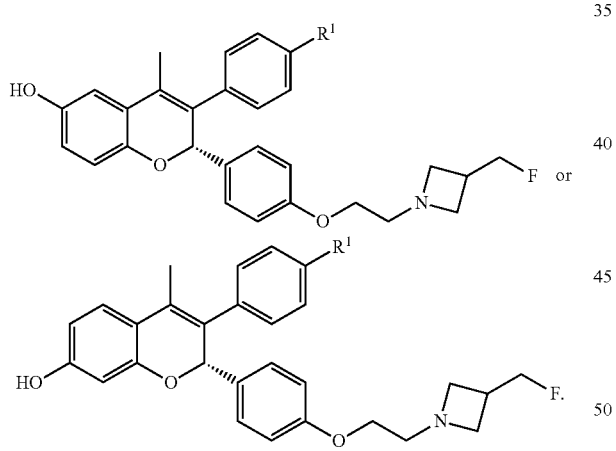

5. The compound of claim 4, wherein $R^1$ is F or CN.

6. The compound of claim 1, wherein the compound of Formula (III) has the following structure:

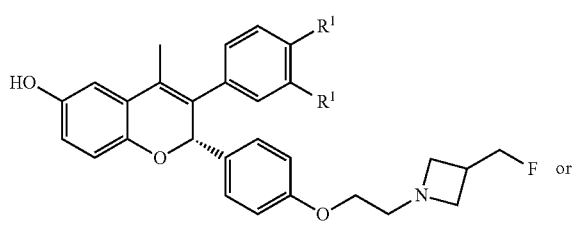

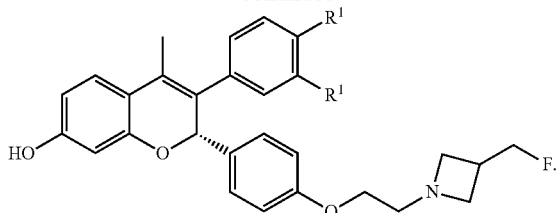

7. The compound of claim 1, wherein the compound of Formula (III) has the following structure:

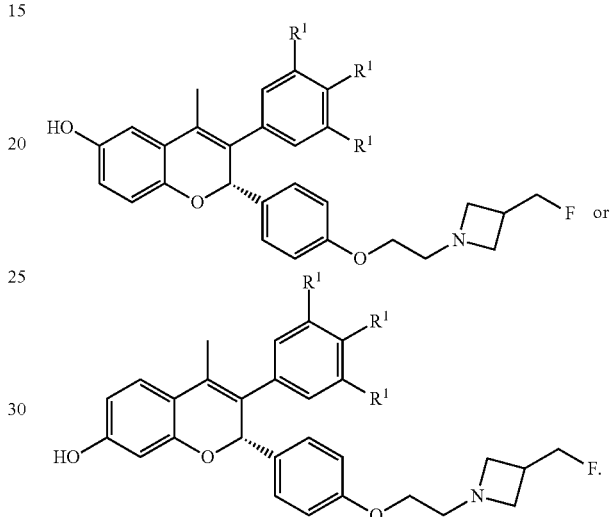

8. The compound of claim 1, selected from:
(S)-2-(4-(2-(3-(Fluoromethyl)azetidin-1-yl)ethoxy)phenyl)-3-(4-fluorophenyl)-4-methyl-2H-chromen-6-ol;
(S)-3-(4-Chlorophenyl)-2-(4-(2-(3-(fluoromethyl)azetidin-1-yl)ethoxy)phenyl)-4-methyl-2H-chromen-6-ol;
(S)-4-(2-(4-(2-(3-(Fluoromethyl)azetidin-1-yl)ethoxy)phenyl)-6-hydroxy-4-methyl-2H-chromen-3-yl)benzonitrile;
(S)-3-(3,4-Difluorophenyl)-2-(4-(2-(3-(fluoromethyl)azetidin-1-yl)ethoxy)phenyl)-4-methyl-2H-chromen-6-ol;
(S)-3-(3-Chloro-4-fluorophenyl)-2-(4-(2-(3-(fluoromethyl)azetidin-1-yl)ethoxy)phenyl)-4-methyl-2H-chromen-6-ol;
3-(4-Chloro-3-fluorophenyl)-2-(4-(2-(3-(fluoromethyl)azetidin-1-yl)ethoxy)phenyl)-4-methyl-2H-chromen-6-ol;
(S)-3-(4-Chloro-3-fluorophenyl)-2-(4-(2-(3-(fluoromethyl)azetidin-1-yl)ethoxy)phenyl)-4-methyl-2H-chromen-6-ol;
(S)-2-(4-(2-(3-(Fluoromethyl)azetidin-1-yl)ethoxy)phenyl)-4-methyl-3-(3,4,5-trifluorophenyl)-2H-chromen-6-ol;
(S)-2-(4-(2-(3-(Fluoromethyl)azetidin-1-yl)ethoxy)phenyl)-4-methyl-3-(4-(trifluoromethyl)phenyl)-2H-chromen-6-ol;
(S)-2-(4-(2-(3-(Fluoromethyl)azetidin-1-yl)ethoxy)phenyl)-3-(4-fluorophenyl)-4-methyl-2H-chromen-7-ol; and
(S)-3-(4-Chlorophenyl)-2-(4-(2-(3-(fluoromethyl)azetidin-1-yl)ethoxy)phenyl)-4-methyl-2H-chromen-7-ol.

9. A pharmaceutically acceptable salt of a compound that has a structure as defined in claim 1.

10. The pharmaceutically acceptable salt of claim 9, wherein the pharmaceutically acceptable salt of the compound is a hydrochloric acid salt, a hydrobromic acid salt, a sulfuric acid salt, a phosphoric acid salt, a metaphosphoric acid salt, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a L-malic acid salt, a maleic acid salt, an oxalic acid salt, a fumaric acid salt, a trifluoroacetic acid salt, a tartaric acid salt, a L-tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, or a valproic acid salt.

11. A pharmaceutical composition comprising a compound or a pharmaceutically acceptable salt of claim 1, and one or more pharmaceutically acceptable inactive ingredients selected from carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, and preservatives.

12. The pharmaceutical composition of claim 11, wherein the pharmaceutical composition is formulated for intravenous injection, subcutaneous injection, oral administration, or topical administration.

13. The pharmaceutical composition of claim 11, wherein the pharmaceutical composition is a tablet, a pill, a capsule, a liquid, a suspension, a gel, a dispersion, a solution, an emulsion, an ointment, or a lotion.

14. A kit for therapeutically treating an ER-related disease or condition, comprising:
   a) a pharmaceutical composition of claim 11; and
   b) instructions for use
   wherein the ER-related disease or condition is breast cancer.

* * * * *